United States Patent
Glunz et al.

(10) Patent No.: US 9,221,767 B2
(45) Date of Patent: Dec. 29, 2015

(54) SUBSTITUTED PHTHALAZINONES AS ROCK INHIBITORS

(71) Applicant: BRISTOL-MYERS SQUIBB COMPANY, Princeton, NJ (US)

(72) Inventors: Peter W. Glunz, Yardley, PA (US); Yan Zou, Jamison, PA (US); Mimi L. Quan, Yardley, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 14/157,564

(22) Filed: Jan. 17, 2014

(65) Prior Publication Data

US 2014/0206686 A1     Jul. 24, 2014

Related U.S. Application Data

(60) Provisional application No. 61/754,007, filed on Jan. 18, 2013.

(51) Int. Cl.

| | | |
|---|---|---|
| *A61K 31/502* | (2006.01) | |
| *C07D 237/32* | (2006.01) | |
| *C07D 401/10* | (2006.01) | |
| *C07D 401/12* | (2006.01) | |
| *C07D 403/10* | (2006.01) | |
| *C07D 403/12* | (2006.01) | |
| *C07D 405/12* | (2006.01) | |
| *C07D 413/12* | (2006.01) | |
| *C07D 417/12* | (2006.01) | |
| *C07D 417/14* | (2006.01) | |
| *C07D 513/04* | (2006.01) | |
| *C07D 217/24* | (2006.01) | |
| *C07D 413/10* | (2006.01) | |
| *C07D 417/10* | (2006.01) | |
| *C07D 471/04* | (2006.01) | |
| *C07D 487/04* | (2006.01) | |
| *C07D 491/048* | (2006.01) | |

(52) U.S. Cl.
CPC .......... *C07D 237/32* (2013.01); *C07D 217/24* (2013.01); *C07D 401/10* (2013.01); *C07D 401/12* (2013.01); *C07D 403/10* (2013.01); *C07D 403/12* (2013.01); *C07D 405/12* (2013.01); *C07D 413/10* (2013.01); *C07D 413/12* (2013.01); *C07D 417/10* (2013.01); *C07D 417/12* (2013.01); *C07D 417/14* (2013.01); *C07D 471/04* (2013.01); *C07D 487/04* (2013.01); *C07D 491/048* (2013.01); *C07D 513/04* (2013.01)

(58) Field of Classification Search
CPC .............................. A61K 31/502; C07D 237/32
USPC .................. 514/248; 544/237, 238, 322, 386;
546/146, 245, 304; 548/128, 161, 190,
548/217, 235, 247, 307.4, 492, 530;
549/362
See application file for complete search history.

(56) References Cited

U.S. PATENT DOCUMENTS

2012/0122842 A1     5/2012     Curtin et al.

FOREIGN PATENT DOCUMENTS

| CN | 102180909 A | 9/2011 |
|---|---|---|
| CN | 103242647 A | 8/2013 |
| DE | 25 31 776 A1 | 2/1977 |
| DE | 198 04 085 A1 | 8/1999 |
| EP | 0 475 527 A2 | 3/1992 |
| EP | 0 481 383 A1 | 4/1992 |
| EP | 0 634 402 A1 | 1/1995 |
| JP | 2000-72675 A | 3/2000 |
| WO | WO 98/38168 | 9/1998 |
| WO | WO 99/40072 | 8/1999 |
| WO | WO 00/44726 | 8/2000 |
| WO | WO 00/50419 | 8/2000 |
| WO | WO 02/36576 | 5/2002 |

(Continued)

OTHER PUBLICATIONS

Kiselyov, et al. Chemical Biology & Drug Design, 68(5), 2006, 250-255.*
CAS Registry No. 401646-88-6, Entered STN: Mar. 18, 2002.
CAS Registry No. 674337-79-2, Entered STN: Apr. 12, 2004.
CAS Registry No. 692279-56-4, Entered STN: Jun. 13, 2004.
CAS Registry No. 700349-58-2, Entered STN: Jun. 28, 2004.
CAS Registry No. 939750-00-2, Entered STN: Jun. 28, 2007.
CAS Registry No. 1180660-61-0, Entered STN: Sep. 4, 2009.
Mei, Q. et al., "Highly efficient red indium(III) complexes based on phthalazine derivatives for organic light-emitting diodes", Dyes and Pigments, vol. 97, pp. 43-51 (2013).
Reaxys® PubChem Report generated Dec. 23, 2013.

*Primary Examiner* — Douglas M Willis
(74) *Attorney, Agent, or Firm* — Hong Liu

(57) ABSTRACT

The present invention provides compounds of Formula (I):

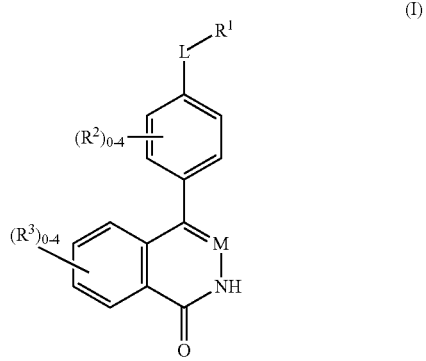

or stereoisomers, tautomers, or pharmaceutically acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

10 Claims, No Drawings

(56) References Cited

FOREIGN PATENT DOCUMENTS

| WO | WO 03/068750 | 8/2003 |
| WO | WO 2004/024694 | 3/2004 |
| WO | WO 2005/097750 | 10/2005 |
| WO | WO 2006/036981 | 4/2006 |
| WO | WO 2006/124874 | * 11/2006 |
| WO | WO 2008/086014 | 7/2008 |
| WO | WO 2009/064422 | 5/2009 |
| WO | WO 2011/019400 | 2/2011 |
| WO | WO 2012/072033 | 6/2012 |

* cited by examiner

SUBSTITUTED PHTHALAZINONES AS ROCK INHIBITORS

FIELD OF THE INVENTION

The present invention relates generally to novel phthalazinone and isoquinolinone compounds, and their analogues thereof, which are inhibitors of Rho kinases, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (T. Ishizaki et al., EMBO J., 1996, 15, 1885-1893). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as actin organization, cell adhesion, cell migration, and cytokinesis (K. Riento and A. J. Ridley, Nat Rev Mol Cell Biol, 2003, 4, 446-56). It is also directly involved in regulating smooth muscle contraction (A. P. Somlyo, Nature, 1997, 389, 908-911). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example angiotensin II (T. Yamakawa et al., Hypertension, 2000, 35, 313-318), urotension II (V. Sauzeau et al., Circ. Res., 2001, 88, 1102-1104), endothelin-1 (P. Tangkijvanich et al., Hepatology, 2001, 33, 74-80), serotonin (H. Shimokawa, Jpn. Circ. J., 2000, 64, 1-12), norepinephrine (M. C. Martinez, et al., Am. J. Physiol., 2000, 279, H1228-H1238) and platelet-derived growth factor (PDGF) (H. Kishi et al., J. Biochem., 2000, 128, 719-722). Many of these factors are implicated in the pathogenesis of cardiovascular disease.

Additional studies in the literature, some using the known ROCK inhibitors fasudil (T. Asano et al., J. Pharmacol. Exp. Ther., 1987, 241, 1033-1040) or Y-27632 (M. Uehata et al., Nature, 1997, 389, 990-994) further illustrate the link between ROCK and cardiovascular disease. For example, ROCK expression and activity have been shown to be elevated in spontaneously hypertensive rats, suggesting a link to the development of hypertension in these animals (Y. Mukai et al., FASEB J., 2001, 15, 1062-1064). The ROCK inhibitor Y-27632 (M. Uehata et al., Nature, ibid) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Y. Eto et al., Am. J. Physiol. Heart Circ. Physiol., 2000, 278, H1744-H1750). In a similar model, ROCK inhibitor Y-27632 also inhibited neointimal formation in rats (N. Sawada et al., Circulation, 2000, 101, 2030-2033). In a porcine model of IL-1 beta-induced coronary stenosis, long term treatment with the ROCK inhibitor fasudil was shown to progressively reduce coronary stenosis, as well as promote a regression of coronary constrictive remodeling (H. Shimokawa et al., Cardiovascular Res., 2001, 51, 169-177).

Additional investigations suggest that a ROCK inhibitor would be useful in treating other cardiovascular diseases. For example, in a rat stroke model, fasudil was shown to reduce both the infarct size and neurologic deficit (Y. Toshima, Stroke, 2000, 31, 2245-2250). The ROCK inhibitor Y-27632 was shown to improve ventricular hypertrophy, fibrosis and function in a model of congestive heart failure in Dahl salt-sensitive rats (N. Kobayashi et al. Cardiovascular Res., 2002, 55, 757-767).

Other animal or clinical studies have implicated ROCK in additional diseases including coronary vasospasm (H. Shimokawa et al., Cardiovasc. Res., 1999, 43, 1029-1039), cerebral vasospasm (M. Sato et al., Circ. Res., 2000, 87, 195-200), ischemia/reperfusion injury (T. Yada et al., J. Am. Coll. Cardiol., 2505, 45, 599-607), pulmonary hypertension (Y. Fukumoto et al., Heart, 2005, 91, 391-392), angina (H. Shimokawa et al., J. Cardiovasc. Pharmacol., 2002, 39, 319-327), renal disease (S. Satoh et al., Eur. J. Pharmacol., 2002, 455, 169-174) and erectile dysfunction (N. F. Gonzalez-Cadavid and J. Rajifer, Endocrine, 2004, 23, 167-176).

In another study, it has been demonstrated that inhibition of the RhoA/ROCK signaling pathway allows formation of multiple competing lamellipodia that disrupt the productive migration of monocytes (R. A. Worthylake et al. The Journal of Biol. Chem., 2003, 278, 13578-13584). It has also been reported that small molecule inhibitors of Rho Kinase are capable of inhibiting MCP-1 mediated chemotaxis in vitro (H. Iijima, Biorganic and Medicinal Chemistry, 2007, 15, 1022-1033). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (H. Shimokawa et al., Arterioscler. Thromb. Vasc. Biol., 2005, 25, 1767-1775). Furthermore, Rho-kinase has been indicated as a drug target for the treatment of various other diseases, including airway inflammation and hyperresponsiveness (P. J. Henry et al., Pulm Pharmacol Ther., 2005, 18, 67-74), cancer (R. Rattan et al., J Neurosci. Res., 2006, 83, 243-55. D. Lepley et al., Cancer Res., 2005, 65, 3788-95), fibrotic diseases (C. Jiang, et. al., Int. J. Mol. Sci., 2012, 13, 8293-8307; L. Zhou, et. al., Am. J. Nephrol., 2011, 34, 468-475), as well as neurological disorders, such as spinal-cord injury, Alzheimer disease, multiple sclerosis, stroke and neuropathic pain (B. K. Mueller et al., Nat Rev Drug Disc, 2005, 4, 387-398; X. Sun et. al., J. Neuroimmunology, 2006, 180, 126-134).

There remains an unmet medical need for new drugs to treat cardiovascular disease. In the 2012 update of Heart Disease and Stroke Statistics from the American Heart Association (Circulation, 2012, 125, e2-e220), it was reported that cardiovascular disease accounted for 32.8% of all deaths in the US, with coronary heart disease accounting for ~1 in 6 deaths overall in the US. Contributing to these numbers, it was found that ~33.5% of the adult US population was hypertensive, and it was estimated that in 2010 ~6.6 million US adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

Although there are many reports of ROCK inhibitors under investigation (see, for example, U.S. 20120122842 A1, U.S. 20100041645 A1, U.S. 20080161297 A1, and E. Hu and D. Lee, Expert Opin. Ther. Targets, 2005, 9, 715-736), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel phthalazinone and isoquinolinone compounds, their analogues, including stereoisomers, tautomers, pharmaceutically acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

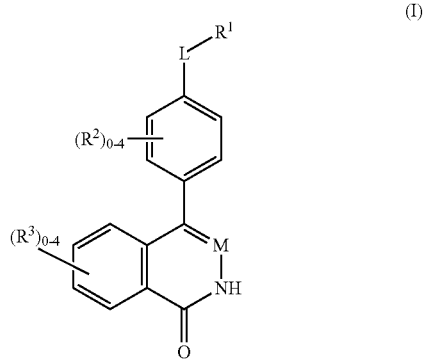

or stereoisomers, tautomers, pharmaceutically acceptable salts, solvates, or prodrugs thereof, wherein:

M is selected from N and $CR^{10}$;

L is selected from $C_{1-2}$ alkylene substituted with 1-2 $R^4$, wherein at least one carbon atom and the groups attached thereto are replaced by O, $NR^6$, and C(O);

$R^1$ is selected from $OC_{1-4}$ alkyl, $NR^5R^5$, $C_{3-10}$ carbocycle and 4- to 12-membered heterocycle comprising carbon atoms and 1-4 heteroatoms selected from N, $NR^8$, O, and $S(O)_p$; wherein said alkyl, carbocycle, and heterocycle are substituted with 1-4 $R^7$;

$R^2$, at each occurrence, is independently selected from halogen, $C_{1-6}$ alkyl, $C_{1-4}$ alkoxy, $C_{1-4}$ alkylthio, $C_{1-4}$ haloalkyl, —OH, —$CH_2OH$, —$OCH_2F$, —$OCHF_2$, —$OCF_3$, CN, —$NH_2$, —NH($C_{1-4}$ alkyl), —N($C_{1-4}$ alkyl)$_2$, —$CO_2H$, —$CH_2CO_2H$, —$CO_2(C_{1-4}$ alkyl), —CO($C_{1-4}$ alkyl), —$CH_2NH_2$, —$CONH_2$, —CONH($C_{1-4}$ alkyl), —CON($C_{1-4}$ alkyl)$_2$, —$OCH_2CO_2H$, —NHCO($C_{1-4}$ alkyl), —$NHCO_2$($C_{1-4}$ alkyl), —$NHSO_2$($C_{1-4}$ alkyl), —$SO_2NH_2$, —C(=NH)$NH_2$, carbocycle, and heterocycle, wherein said alkyl, alkoxy, alkylthio, haloalkyl, carbocycle, and heterocycle are substituted with 0-4 $R^9$;

$R^3$, at each occurrence, is independently selected from halogen, $C_{1-6}$ alkyl, $C_{1-4}$ alkoxy, $C_{1-4}$ alkylthio, $C_{1-4}$ haloalkyl, —$CH_2OH$, —$OCH_2F$, —$OCHF_2$, —$OCF_3$, CN, —$NH_2$, —NH($C_{1-4}$ alkyl), —N($C_{1-4}$ alkyl)$_2$, —$CO_2H$, —$CH_2CO_2H$, —$CO_2(C_{1-4}$ alkyl), —CO($C_{1-4}$ alkyl), —$CH_2NH_2$, —$CONH_2$, —CONH($C_{1-4}$ alkyl), —CON($C_{1-4}$ alkyl)$_2$, —$OCH_2CO_2H$, —NHCO($C_{1-4}$ alkyl), —$NHCO_2$($C_{1-4}$ alkyl), —$NHSO_2$($C_{1-4}$ alkyl), —$SO_2NH_2$, —C(=NH)

NH₂, carbocycle, and heterocycle, wherein said alkyl, alkoxy, alkylthio, haloalkyl, carbocycle, and heterocycle are substituted with 0-4 $R^9$;

$R^4$, at each occurrence, is independently selected from H, halogen, OH, NH₂, CH₂NH₂, $C_{1-4}$ haloalkyl, OCH₂F, OCHF₂, OCF₃, —NH($C_{1-4}$ alkyl), —N($C_{1-4}$ alkyl)₂, $C_{1-4}$ alkoxy, CH₂OH, CH₂O($C_{1-4}$ alkyl), CH₂CO₂H, CH₂CO₂($C_{1-4}$ alkyl), $C_{1-4}$ alkyl, carbocycle, and heterocycle, wherein said alkyl, alkoxy, haloalkyl, carbocycle, and heterocycle are substituted with 0-4 $R^9$;

$R^5$, at each occurrence, is independently selected from H, $C_{1-4}$ alkyl, —$(CR^6R^6)_n$—$C_{3-10}$ carbocycle and —$(CR^6R^6)_n$- 4-10 membered heterocycle comprising carbon atoms and 1-4 heteroatoms selected from N, $NR^8$, O, and $S(O)_p$, wherein said alkyl, carbocycle and heterocycle are substituted with 1-4 $R^7$;

alternatively, $R^5$ and $R^5$ are taken together with the nitrogen atom to which they are attached to form 4- to 10-membered heterocycle substituted with 1-4 $R^7$;

$R^6$, at each occurrence, is independently selected from H and $C_{1-4}$ alkyl;

$R^7$, at each occurrence, is independently selected from H, =O, halogen, $C_{1-4}$ alkyl, $C_{1-4}$ alkoxy, CN, OH, CF₃, —(CH₂)ₙ—CO₂H, —(CH₂)ₙ—CO₂($C_{1-4}$ alkyl), —(CH₂)ₙ—$NR^8R^8$, —NHCO($C_{1-4}$ alkyl), —NHCOCF₃, —NHCO₂($C_{1-4}$ alkyl), —NHCO₂(CH₂)₂O($C_{1-4}$ alkyl), —NHCO₂(CH₂)₃O($C_{1-4}$ alkyl), —NHCO₂(CH₂)₂OH, —NHCO₂(CH₂)₂NH₂, —NHCO₂(CH₂)₂N($C_{1-4}$ alkyl)₂, —NHCO₂CH₂CO₂H, —CH₂NHCO₂($C_{1-4}$ alkyl), —NHC(O)NH₂, —NHC(O)NH($C_{1-4}$ alkyl), —NHC(O)N($C_{1-4}$ alkyl)₂, —NHSO₂($C_{1-4}$ alkyl), —SO₂NH₂, —SO₂NH($C_{1-4}$ alkyl), —SO₂N($C_{1-4}$ alkyl)₂, —SO₂NH(CH₂)₂OH, —SO₂NH(CH₂)₂O($C_{1-4}$ alkyl), —CONH₂, —CONH($C_{1-4}$ alkyl), —CON($C_{1-4}$ alkyl)₂, —CH₂CONH₂, —(CH₂)ₙ-carbocycle, —O(CH₂)ₙ-carbocycle, —O(CH₂)ₙ-heterocycle, and —(CH₂)ₙ-heterocycle comprising carbon atoms and 1-4 heteroatoms selected from N, $NR^8$, O, and $S(O)_p$, wherein said alkyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, C(O)carbocycle, C(O)heterocycle, C(O)$NR^5R^5$, C(O)O-alkyl, C(O)O-carbocycle, C(O)O-heterocycle, SO₂alkyl, SO₂carbocycle, SO₂heterocycle, SO₂$NR^5R^5$, —(CH₂)ₙ-carbocycle, and —(CH₂)ₙ-heterocycle, wherein said alkyl, carbocycle, and heterocycle are substituted with 0-4 $R^9$;

alternatively, $R^8$ and $R^8$ are taken together with the nitrogen atom to which they are attached to form 4- to 10-membered heterocycle substituted with 0-4 $R^9$;

$R^9$, at each occurrence, is independently selected from halogen, OH, NO₂, CHF₂, CF₃, $C_{1-4}$ alkyl, $C_{1-4}$ alkoxy, CH₂OH, CO₂H, CO₂($C_{1-4}$ alkyl), CONH₂, —(CH₂)ₙ$NR^aR^a$, —(CH₂)ₙ$CONR^aR^a$, —O(CH₂)ₙheterocycle, —O(CH₂)₍₂₋₄₎$NR^aR^a$, —$(CR^{10}R^{10})_n$-4-10 membered heterocycle, wherein said alkyl, alkoxyl, and heterocycle are substituted with 0-4 $R^b$;

$R^{10}$ is selected from H and $C_{1-4}$ alkyl;

$R^a$, at each occurrence, is independently selected from H, $C_{1-4}$ alkyl, —(CH₂)ₙOH, CO($C_{1-4}$ alkyl), COCF₃, CO₂($C_{1-4}$ alkyl), —CONH₂, —CONH—$C_{1-4}$ alkylene-CO₂($C_{1-4}$ alkyl), $C_{1-4}$ alkylene-CO₂($C_{1-4}$ alkyl), $R^c$, CO₂$R^c$, and CONHR$^c$; alternatively, $R^a$ and $R^a$ are taken together with the nitrogen atom to which they are attached to form 4- to 10-membered heterocycle, wherein said alkyl, alkylene, and heterocycle are substituted with 0-4 $R^b$;

$R^b$, at each occurrence, is independently selected from =O, halo, $C_{1-4}$ alkyl, $C_{1-4}$ alkoxy, OCF₃, NH₂, NO₂, N($C_{1-4}$ alkyl)₂, CO($C_{1-4}$ alkyl), CO($C_{1-4}$ haloalkyl), CO₂($C_{1-4}$ alkyl), CONH₂, —CONH($C_{1-4}$ alkyl), —CON($C_{1-4}$ alkyl)₂, —CONH—$C_{1-4}$ alkylene-O($C_{1-4}$ alkyl), —CONH—$C_{1-4}$ alkylene-N($C_{1-4}$ alkyl)₂, —CONH—$C_{1-4}$ alkylene-N($C_{1-4}$ alkyl)₂, —CONH—$C_{1-4}$ alkylene-O—P(O)(OH)₂, —NHCO₂($C_{1-4}$ alkyl), —$R^c$, CO$R^c$, CO₂$R^c$, and CONHR$^c$;

$R^c$, at each occurrence, is independently selected from —(CH₂)ₙ—$C_{3-6}$ cycloalkyl, —(CH₂)ₙ-phenyl, and —(CH₂)ₙ-5- to 6-membered heterocycle containing carbon atoms and 1-4 heteroatoms selected from the group consisting of: N, NH, N($C_{1-4}$ alkyl), O, and $S(O)_p$; wherein each ring moiety is substituted with 0-2 $R^d$;

$R^d$, at each occurrence, is independently selected from =O, halo, —OH, $C_{1-4}$ alkyl, NH₂, NH($C_{1-4}$ alkyl), N($C_{1-4}$ alkyl)₂, $C_{1-4}$ alkoxy, and —NHCO($C_{1-4}$ alkyl), and heterocycle containing carbon atoms and 1-4 heteroatoms selected from the group consisting of: N, NH, N($C_{1-4}$ alkyl), O, and $S(O)_p$;

n, at each occurrence, is independently selected from 0, 1, 2, 3, and 4;

p, at each occurrence, is independently selected from 0, 1, and 2;

provided (1) when L is NHC(O), $R^1$ is other than

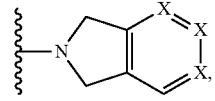

wherein X is N or a substituted or unsubstituted carbon atom;

(2) when L is NH, $R^1$ is other than

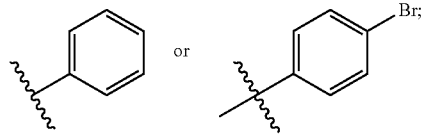 [SMILES: *c1ccccc1 ; *c1ccc(Br)cc1]

(3) when L is O, $R^1$ is other than

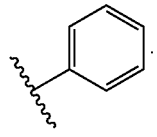

In another aspect, the present invention provides compounds of Formula (I) or stereoisomers, tautomers, pharmaceutically acceptable salts, solvates, or prodrugs thereof, wherein:

L is selected from —$CR^4R^4C(O)$—, —OC(O)—, —$NR^6C(O)$—, and —$NR^6$—;

$R^4$, at each occurrence, is independently selected from H and $C_{1-4}$ alkyl; and $R^7$, at each occurrence, is independently selected from H, =O, halogen, $C_{1-4}$ alkyl, $C_{1-4}$ alkoxy, CN, OH, CF₃, —(CH₂)ₙ—CO₂H, —(CH₂)ₙ—CO₂($C_{1-4}$ alkyl), —(CH₂)ₙ—$NR^8R^8$, —NHCO($C_{1-4}$ alkyl), —NHCOCF₃, —NHCO₂($C_{1-4}$ alkyl), —NHCO₂(CH₂)₂OH, —NHC(O)NH₂, —NHC(O)NH($C_{1-4}$ alkyl), —NHC(O)N($C_{1-4}$ alkyl)₂, —NHSO₂($C_{1-4}$ alkyl), —SO₂NH₂, —SO₂NH($C_{1-4}$ alkyl), —SO₂N (C$_{1-4}$ alkyl)$_2$, —CONH$_2$, —CONH(C$_{1-4}$ alkyl), —CON(C$_{1-4}$ alkyl)$_2$, —CH$_2$CONH$_2$, —(CH$_2$)$_n$-carbocycle, —O(CH$_2$)$_n$-carbocycle, —O(CH$_2$)$_n$-heterocycle, and —(CH$_2$)$_n$-heterocycle comprising carbon atoms and 1-4 heteroatoms selected from N, NR$^8$, O, and S(O)$_p$ wherein said alkyl, alkoxyl, carbocycle, and heterocycle are substituted with 0-4 R$^9$;

other variables are as defined in Formula (I) above.

In another aspect, the present invention provides compounds of Formula (II):

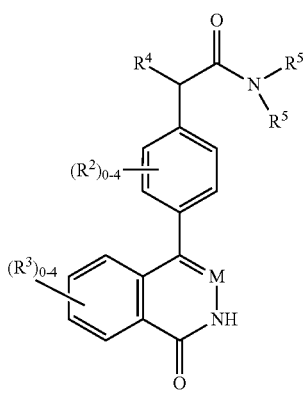

(II)

or stereoisomers, tautomers, pharmaceutically acceptable salts, solvates, or prodrugs thereof, wherein:

M is selected from N and CR$^{10}$;

R$^5$, at each occurrence, is independently selected from H, C$_{1-4}$ alkyl, —(CR$^6$R$^6$)$_n$—C$_{3-10}$ carbocycle, and —(CR$^6$R$^6$)$_n$-4-10 membered heterocycle comprising carbon atoms and 1-4 heteroatoms selected from N, NR$^8$, O, and S(O)$_p$, wherein said alkyl, carbocycle, and heterocycle are substituted with 1-4 R$^7$;

alternatively, R$^5$ and R$^5$ are taken together with the nitrogen atom to which they are attached to form 4- to 10-membered heterocycle substituted with 1-4 R$^7$;

R$^7$, at each occurrence, is independently selected from H, =O, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHC(O)NH$_2$, —NHC(O)NH(C$_{1-4}$ alkyl), —NHC(O)N(C$_{1-4}$ alkyl)$_2$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —CONH$_2$, —CONH(C$_{1-4}$ alkyl), —CON(C$_{1-4}$ alkyl)$_2$, —CH$_2$CONH$_2$—(CH$_2$)$_n$-carbocycle, —O(CH$_2$)$_n$-carbocycle, —O(CH$_2$)$_n$-heterocycle, and —(CH$_2$)$_n$-heterocycle comprising carbon atoms and 1-4 heteroatoms selected from N, NR$^8$, O, and S(O)$_p$, wherein said alkyl, alkoxyl, carbocycle, and heterocycle are substituted with 0-4 R$^9$;

R$^8$, at each occurrence, is independently selected from H, C$_{1-4}$ alkyl, C(O)C$_{1-4}$alkyl, C(O)carbocycle, C(O)heterocycle, C(O)NR$^5$R$^5$, C(O)O-alkyl, C(O)O-carbocycle, C(O)O-heterocycle, SO$_2$alkyl, SO$_2$carbocycle, SO$_2$heterocycle, SO$_2$NR$^5$R$^5$, —(CH$_2$)$_n$-carbocycle, and —(CH$_2$)$_n$-heterocycle, wherein said alkyl, carbocycle, and heterocycle are substituted with 0-4 R$^9$;

R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —O(CH$_2$)$_n$heterocycle, —O(CH$_2$)$_{(2-4)}$NR$^a$R$^a$, —(CR$^{10}$R$^{10}$)$_n$-4-10 membered heterocycle, wherein said alkyl, alkoxyl, and heterocycle are substituted with 0-4 R$^b$;

R$^{10}$ is selected from H and C$_{1-4}$ alkyl;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form 4- to 10-membered heterocycle, wherein said alkyl, alkylene, and heterocycle are substituted with 0-4 R$^b$;

R$^b$, at each occurrence, is independently selected from =O, halo, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N(C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halo, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and heterocycle containing carbon atoms and 1-4 heteroatoms selected from the group consisting of: N, NH, N(C$_{1-4}$ alkyl), O, and S(O)$_p$;

n, at each occurrence, is independently selected from 0, 1, 2, 3, and 4;

p, at each occurrence, is independently selected from 0, 1, and 2;

other variables are as defined in Formula (I) above.

In another aspect, the present invention provides compounds of Formula (II) or stereoisomers, tautomers, pharmaceutically acceptable salts, solvates, or prodrugs thereof, wherein:

R$^5$ is selected from H, C$_{1-4}$ alkyl, —(CH$_2$)$_n$—C$_{3-6}$ cycloalkyl, —(CH$_2$)$_n$-aryl, —(CH$_2$)$_n$-4-10 membered heterocycle selected from

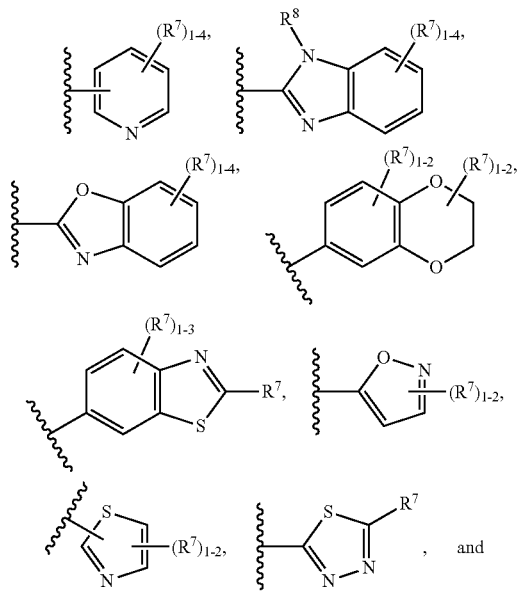

-continued

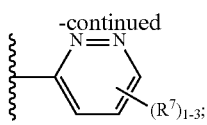

other variables are as defined in Formula (I) above.

In another aspect, the present invention provides compounds of Formula (II) or stereoisomers, tautomers, pharmaceutically acceptable salts, solvates, or prodrugs thereof, wherein:

$R^5$ and $R^5$ are taken together with the nitrogen atom to which they are attached to form a heterocycle selected from

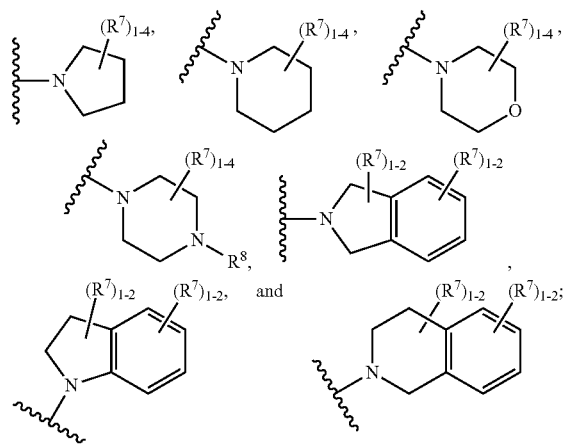

other variables are as defined in Formula (I) above.

In another aspect, the present invention provides compounds of Formula (III):

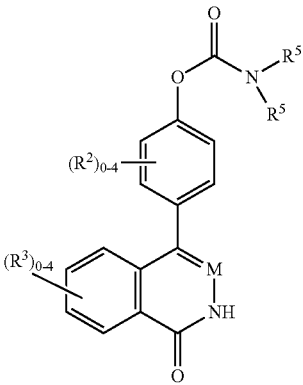

(III)

or stereoisomers, tautomers, pharmaceutically acceptable salts, solvates, or prodrugs thereof, wherein:

M is selected from N and $CR^{10}$;

$R^5$, at each occurrence, is independently selected from H, $C_{1-4}$ alkyl, —$(CR^6R^6)_n$—$C_{3-10}$ carbocycle, and —$(CR^6R^6)_n$- 4-10 membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form 4- to 10-membered heterocycle substituted with 1-4 $R^7$;

$R^6$, at each occurrence, is independently selected from H and $C_{1-4}$ alkyl;

$R^7$, at each occurrence, is independently selected from H, =O, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2(C_{1-4}$ alkyl), —$NHC(O)NH_2$, —$NHC(O)NH(C_{1-4}$ alkyl), —$NHC(O)N(C_{1-4}$ alkyl)$_2$, —$NHSO_2(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$CONH_2$, —$CONH(C_{1-4}$ alkyl), —$CON(C_{1-4}$ alkyl)$_2$, —$CH_2CONH_2$, —$(CH_2)_n$-carbocycle, —$O(CH_2)_n$-carbocycle, —$O(CH_2)_n$-heterocycle, and —$(CH_2)_n$-heterocycle, wherein said alkyl, alkoxyl, carbocycle, and heterocycle substituted with 0-4 $R^9$;

$R^8$, at each occurrence, is independently selected from H, $C_{1-4}$ alkyl, $C(O)C_{1-4}$alkyl, $C(O)$carbocycle, $C(O)$heterocycle, $C(O)NR^5R^5$, $C(O)O$-alkyl, $C(O)O$-carbocycle, $C(O)O$-heterocycle, $SO_2$alkyl, $SO_2$carbocycle, $SO_2$heterocycle, $SO_2NR^5R^5$, —$(CH_2)_n$-carbocycle, and —$(CH_2)_n$-heterocycle, wherein said alkyl, carbocycle, and heterocycle are substituted with 0-4 $R^9$;

$R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, —$(CH_2)_nNR^aR^a$, —$(CH_2)_nCONR^aR^a$, —$O(CH_2)_n$heterocycle, —$O(CH_2)_{(2-4)}NR^aR^a$, —$(CR^{10}R^{10})_n$-4-10 membered heterocycle, wherein said alkyl, alkoxyl, and heterocycle are substituted with 0-4 $R^b$;

n, at each occurrence, is independently selected from 0, 1, 2, 3, and 4; and p, at each occurrence, is independently selected from 0, 1, and 2;

other variables are as defined in Formula (I) above.

In another aspect, the present invention provides compounds of Formula (I) or stereoisomers, tautomers, pharmaceutically acceptable salts, solvates, or prodrugs thereof, wherein:

L is —$NR^6$—;

$R^1$ is selected from $C_{3-10}$ carbocycle and 5- to 10-membered heterocycle substituted with 1-4 $R^7$;

$R^5$, at each occurrence, is independently selected from H, $C_{1-4}$ alkyl, —$(CR^6R^6)_n$—$C_{3-10}$ carbocycle, and —$(CR^6R^6)_n$- 4-10 membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form 4- to 10-membered heterocycle substituted with 1-4 $R^7$;

$R^6$, at each occurrence, is independently selected from H and $C_{1-4}$ alkyl;

$R^7$, at each occurrence, is independently selected from H, =O, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$CH_2NH_2$, —$NHCO(C_{1-4}$ alkyl), —$NHCOCF_3$, —$NHCO_2(C_{1-4}$ alkyl), —$NHC(O)NH_2$, —$NHC(O)NH(C_{1-4}$ alkyl), —$NHC(O)N(C_{1-4}$ alkyl)$_2$, —$NHSO_2(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$CONH_2$, —$CONH(C_{1-4}$ alkyl), —$CON(C_{1-4}$ alkyl)$_2$, —$CH_2CONH_2$, —$(CH_2)_n$-carbocycle, —$O(CH_2)_n$-carbocycle, —$O(CH_2)_n$-heterocycle, and —$(CH_2)_n$-heterocycle, wherein said alkyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, $C(O)$carbocycle, $C(O)$heterocycle, $C(O)NR^5R^5$, $C(O)O$-alkyl, $C(O)O$-carbocycle, $C(O)$ O-heterocycle, SO$_2$alkyl, SO$_2$carbocycle, SO$_2$heterocycle, SO$_2$NR$^5$R$^5$, —(CH$_2$)$_n$-carbocycle, and —(CH$_2$)$_n$-heterocycle, wherein said alkyl, carbocycle, and heterocycle are substituted with 0-4 R$^9$;

R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —O(CH$_2$)$_n$heterocycle, —O(CH$_2$)$_{(2-4)}$NR$^a$R$^a$, —(CR$^{10}$R$^{10}$)$_n$-4-10 membered heterocycle, wherein said alkyl, alkoxyl, and heterocycle are substituted with 0-4 R$^b$;

n, at each occurrence, is independently selected from 0, 1, 2, 3, and 4;

p, at each occurrence, is independently selected from 0, 1, and 2;

other variables are as defined in Formula (I) above.

In another aspect, the present invention provides compounds of Formula (I) or stereoisomers, tautomers, pharmaceutically acceptable salts, solvates, or prodrugs thereof, wherein:

L is —NR$^6$—; and
R$^1$ is selected from

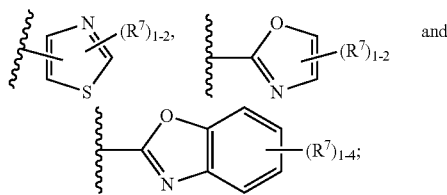

other variables are as defined in Formula (I) above.

In still another aspect, the present invention provides compounds of Formula (IV):

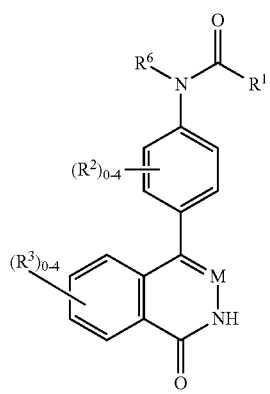

(IV)

or stereoisomers, tautomers, pharmaceutically acceptable salts, solvates, or prodrugs thereof, wherein:

R$^1$ is selected from NR$^5$R$^5$, C$_{3-10}$ carbocycle, and 5- to 10-membered heterocycle, wherein said carbocycle and heterocycle are substituted with 1-4 R$^7$;

R$^5$, at each occurrence, is independently selected from H, C$_{1-4}$ alkyl, —(CR$^6$R$^6$)$_n$—C$_{3-10}$ carbocycle, and —(CR$^6$R$^6$)$_n$-4-10 membered heterocycle comprising carbon atoms and 1-4 heteroatoms selected from N, NR$^8$, O, and S(O)$_p$, wherein said alkyl, carbocycle, and heterocycle are substituted with 1-4 R$^7$;

alternatively, R$^5$ and R$^5$ are taken together with the nitrogen atom to which they are attached to form 4- to 10-membered heterocycle substituted with 1-4 R$^7$;

R$^6$, at each occurrence, is independently selected from H and C$_{1-4}$ alkyl;

R$^7$, at each occurrence, is independently selected from H, =O, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHC(O)NH$_2$, —NHC(O)NH(C$_{1-4}$ alkyl), —NHC(O)N(C$_{1-4}$ alkyl)$_2$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —CONH$_2$, —CONH(C$_{1-4}$ alkyl), —CON(C$_{1-4}$ alkyl)$_2$, —CH$_2$CONH$_2$, —(CH$_2$)$_n$-carbocycle, —O(CH$_2$)$_n$-carbocycle, —O(CH$_2$)$_n$-heterocycle, and —(CH$_2$)$_n$-heterocycle, wherein said alkyl, alkoxyl, carbocycle, and heterocycle are substituted with 0-4 R$^9$;

R$^8$, at each occurrence, is independently selected from H, C$_{1-4}$ alkyl, C(O)C$_{1-4}$alkyl, C(O)carbocycle, C(O)heterocycle, C(O)NR$^5$R$^5$, C(O)O-alkyl, C(O)O-carbocycle, C(O)O-heterocycle, SO$_2$alkyl, SO$_2$carbocycle, SO$_2$heterocycle, SO$_2$NR$^5$R$^5$, —(CH$_2$)$_n$-carbocycle, and —(CH$_2$)$_n$-heterocycle, wherein said alkyl, carbocycle, and heterocycle are substituted with 0-4 R$^9$;

R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —O(CH$_2$)$_n$heterocycle, —O(CH$_2$)$_{(2-4)}$NR$^a$R$^a$, —(CR$^{10}$R$^{10}$)$_n$-4-10 membered heterocycle, wherein said alkyl, alkoxyl, and heterocycle are substituted with 0-4 R$^b$;

n, at each occurrence, is independently selected from 0, 1, 2, 3, and 4;

p, at each occurrence, is independently selected from 0, 1, and 2;

other variables are as defined in Formula (I) above.

In still another aspect, the present invention provides compounds of Formula (IV), or stereoisomers, tautomers, pharmaceutically acceptable salts, solvates, or prodrugs thereof, wherein:

R$^1$ is selected from

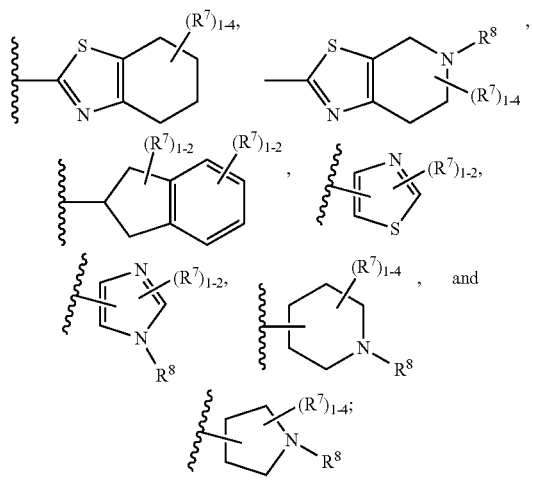

R$^7$, at each occurrence, is independently selected from H, =O, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$ —NR⁸R⁸, —CH₂NH₂, —NHCO(C₁₋₄ alkyl), —NHCOCF₃, —NHCO₂(C₁₋₄ alkyl), —NHC(O)N(C₁₋₄ alkyl)₂, —NHC(O)NH₂, —NHC(O)NH(C₁₋₄ alkyl), —NHSO₂(C₁₋₄ alkyl), —SO₂NH₂, —SO₂NH(C₁₋₄ alkyl), —SO₂N(C₁₋₄ alkyl)₂, —SO₂NH(CH₂)₂OH, —SO₂NH(CH₂)₂O(C₁₋₄ alkyl), —CONH₂, —CONH(C₁₋₄ alkyl), —CON(C₁₋₄ alkyl)₂, —CH₂CONH₂, —(CH₂)ₙ-carbocycle, —O(CH₂)ₙ-carbocycle, —O(CH₂)ₙ-heterocycle, and —(CH₂)ₙ-heterocycle comprising carbon atoms and 1-4 heteroatoms selected from N, NR⁸, O, and S(O)ₚ, wherein said alkyl, alkoxyl, carbocycle, and heterocycle are substituted with 0-4 R⁹;

R⁸, at each occurrence, is independently selected from H, C₁₋₄ alkyl, C(O)C₁₋₄alkyl, C(O)carbocycle, C(O)heterocycle, C(O)NR⁵R⁵, C(O)O-alkyl, C(O)O-carbocycle, C(O)O-heterocycle, SO₂alkyl, SO₂carbocycle, SO₂heterocycle, SO₂NR⁵R⁵, —(CH₂)ₙ-carbocycle, and —(CH₂)ₙ-heterocycle, wherein said alkyl, carbocycle, and heterocycle are substituted with 0-4 R⁹; and R⁹, at each occurrence, is independently selected from halogen, OH, NO₂, CHF₂, CF₃, C₁₋₄ alkyl, C₁₋₄ alkoxy, CH₂OH, CO₂H, CO₂(C₁₋₄ alkyl), CONH₂, —(CH₂)ₙNRᵃRᵃ, —(CH₂)ₙCONRᵃRᵃ, —O(CH₂)ₙheterocycle, —O(CH₂)₍₂₋₄₎NRᵃRᵃ, —(CR¹⁰R¹⁰)ₙ-4-10 membered heterocycle, wherein said alkyl, alkoxyl, and heterocycle are substituted with 0-4 R^b;

other variables are as defined in Formula (I) above.

In still another aspect, the present invention provides compounds of Formula (IV), or stereoisomers, tautomers, pharmaceutically acceptable salts, solvates, or prodrugs thereof, wherein:

R¹ is NR⁵R⁵;

R⁵, at each occurrence, is independently selected from H, C₁₋₄ alkyl, —(CR⁶R⁶)ₙ—C₃₋₁₀ carbocycle, and —(CR⁶R⁶)ₙ-4-10 membered heterocycle comprising carbon atoms and 1-4 heteroatoms selected from N, NR⁸, O, and S(O)ₚ, wherein said alkyl, carbocycle, and heterocycle are substituted with 1-4 R⁷;

alternatively, R⁵ and R⁵ are taken together with the nitrogen atom to which they are attached to form 4- to 10-membered heterocycle substituted with 1-4 R⁷;

R⁶, at each occurrence, is independently selected from H and C₁₋₄ alkyl;

R⁷, at each occurrence, is independently selected from H, =O, halogen, C₁₋₄ alkyl, C₁₋₄ alkoxy, CN, OH, CF₃, —(CH₂)ₙ—CO₂H, —(CH₂)ₙ—CO₂(C₁₋₄ alkyl), —(CH₂)ₙ—NR⁸R⁸, —NHCO(C₁₋₄ alkyl), —NHCOCF₃, —NHCO₂(C₁₋₄ alkyl), —NHC(O)NH₂, —NHC(O)NH(C₁₋₄ alkyl), —NHC(O)N(C₁₋₄ alkyl)₂, —NHSO₂(C₁₋₄ alkyl), —SO₂NH₂, —SO₂NH(C₁₋₄ alkyl), —SO₂N(C₁₋₄ alkyl)₂, —SO₂NH(CH₂)₂OH, —SO₂NH(CH₂)₂O(C₁₋₄ alkyl), —CONH₂, —CONH(C₁₋₄ alkyl), —CON(C₁₋₄ alkyl)₂, —CH₂CONH₂, —(CH₂)ₙ-carbocycle, —O(CH₂)ₙ-carbocycle, —O(CH₂)ₙ-heterocycle, and —(CH₂)ₙ-heterocycle comprising carbon atoms and 1-4 heteroatoms selected from N, NR⁸, O, and S(O)ₚ, wherein said alkyl, alkoxyl, carbocycle, and heterocycle are substituted with 0-4 R⁹;

R⁸, at each occurrence, is independently selected from H, C₁₋₄ alkyl, C(O)C₁₋₄alkyl, C(O)carbocycle, C(O)heterocycle, C(O)NR⁵R⁵, C(O)O-alkyl, C(O)O-carbocycle, C(O)O-heterocycle, SO₂alkyl, SO₂carbocycle, SO₂heterocycle, SO₂NR⁵R⁵, —(CH₂)ₙ-carbocycle, and —(CH₂)ₙ-heterocycle, wherein said alkyl, carbocycle, and heterocycle are substituted with 0-4 R⁹; and R⁹, at each occurrence, is independently selected from halogen, OH, NO₂, CHF₂, CF₃, C₁₋₄ alkyl, C₁₋₄ alkoxy, CH₂OH, CO₂H, CO₂(C₁₋₄ alkyl), CONH₂, —(CH₂)ₙNRᵃRᵃ, —(CH₂)ₙCONRᵃRᵃ, —O(CH₂)ₙheterocycle, —O(CH₂)₍₂₋₄₎NRᵃRᵃ, —(CR¹⁰R¹⁰)ₙ-4-10 membered heterocycle, wherein said alkyl, alkoxyl, and heterocycle are substituted with 0-4 R^b;

other variables are as defined in Formula (I) above.

In another aspect, the present invention provides compounds of Formula (V):

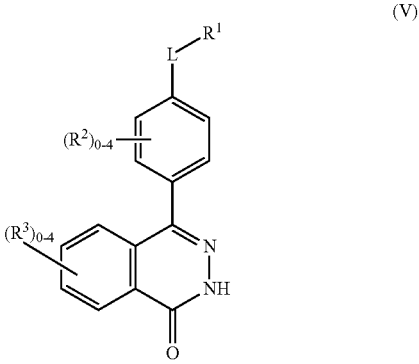

(V)

or stereoisomers, tautomers, pharmaceutically acceptable salts, solvates, or prodrugs thereof, wherein:

L is selected from C₁₋₂ alkylene substituted with 1-2 R⁴, wherein at least one carbon atom and the groups attached thereto are replaced by O, NR⁶, and C(O);

R¹ is selected from OC₁₋₄ alkyl, NR⁵R⁵, C₃₋₁₀ carbocycle and 4- to 12-membered heterocycle comprising carbon atoms and 1-4 heteroatoms selected from N, NR⁸, O, and S(O)ₚ; wherein said alkyl, carbocycle, and heterocycle are substituted with 1-4 R⁷;

R², at each occurrence, is independently selected from halogen, C₁₋₆ alkyl, C₁₋₄ alkoxy, C₁₋₄ alkylthio, C₁₋₄ haloalkyl, —OH, —CH₂OH, —OCH₂F, —OCHF₂, —OCF₃, CN, —NH₂, —NH(C₁₋₄ alkyl), —N(C₁₋₄ alkyl)₂, —CO₂H, —CH₂CO₂H, —CO₂(C₁₋₄ alkyl), —CO(C₁₋₄ alkyl), —CH₂NH₂, —CONH₂, —CONH(C₁₋₄ alkyl), —CON(C₁₋₄ alkyl)₂, —OCH₂CO₂H, —NHCO(C₁₋₄ alkyl), —NHCO₂(C₁₋₄ alkyl), —NHSO₂(C₁₋₄ alkyl), —SO₂NH₂, —C(=NH)NH₂, carbocycle, and heterocycle, wherein said alkyl, alkoxy, alkylthio, haloalkyl, carbocycle, and heterocycle are substituted with 0-4 R⁹;

R³, at each occurrence, is independently selected from halogen, C₁₋₆ alkyl, C₁₋₄ alkoxy, C₁₋₄ alkylthio, C₁₋₄ haloalkyl, —CH₂OH, —OCH₂F, —OCHF₂, —OCF₃, CN, —NH₂, —NH(C₁₋₄ alkyl), —N(C₁₋₄ alkyl)₂, —CO₂H, —CH₂CO₂H, —CO₂(C₁₋₄ alkyl), —CO(C₁₋₄ alkyl), —CH₂NH₂, —CONH₂, —CONH(C₁₋₄ alkyl), —CON(C₁₋₄ alkyl)₂, —OCH₂CO₂H, —NHCO(C₁₋₄ alkyl), —NHCO₂(C₁₋₄ alkyl), —NHSO₂(C₁₋₄ alkyl), —SO₂NH₂, —C(=NH)NH₂, carbocycle, and heterocycle, wherein said alkyl, alkoxy, alkylthio, haloalkyl, carbocycle, and heterocycle are substituted with 0-4 R⁹;

R⁴, at each occurrence, is independently selected from H, halogen, OH, NH₂, CH₂NH₂, C₁₋₄ haloalkyl, OCH₂F, OCHF₂, OCF₃, —NH(C₁₋₄ alkyl), —N(C₁₋₄ alkyl)₂, C₁₋₄ alkoxy, CH₂OH, CH₂O(C₁₋₄ alkyl), CH₂CO₂H, CH₂CO₂(C₁₋₄ alkyl), C₁₋₄ alkyl, carbocycle, and heterocycle, wherein said haloalkyl, alkyl, alkoxy, carbocycle and heterocycle are substituted with 0-4 R⁹;

R⁵, at each occurrence, is independently selected from H, C₁₋₄ alkyl, —(CR⁶R⁶)ₙ—C₃₋₁₀ carbocycle and —(CR⁶R⁶)ₙ-4-10 membered heterocycle comprising carbon atoms and 1-4 heteroatoms selected from N, $NR^8$, O, and $S(O)_p$, wherein said alkyl, carbocycle and heterocycle are substituted with 1-4 $R^7$;

alternatively, $R^5$ and $R^5$ are taken together with the nitrogen atom to which they are attached to form 4- to 10-membered heterocycle substituted with 1-4 $R^7$;

$R^6$, at each occurrence, is independently selected from H and $C_{1-4}$ alkyl;

$R^7$, at each occurrence, is independently selected from H, =O, halogen, $C_{1-4}$ alkyl, $C_{1-4}$ alkoxy, CN, OH, $CF_3$, $-(CH_2)_n-CO_2H$, $-(CH_2)_n-CO_2(C_{1-4}$ alkyl), $-(CH_2)_n-NR^8R^8$, $-NHCO(C_{1-4}$ alkyl), $-NHCOCF_3$, $-NHCO_2(C_{1-4}$ alkyl), $-NHCO_2(CH_2)_2O(C_{1-4}$ alkyl), $-NHCO_2(CH_2)_3O(C_{1-4}$ alkyl), $-NHCO_2(CH_2)_2OH$, $-NHCO_2(CH_2)_2NH_2$, $-NHCO_2(CH_2)_2N(C_{1-4}$ alkyl)$_2$, $-NHCO_2CH_2CO_2H$, $-CH_2NHCO_2(C_{1-4}$ alkyl), $-NHC(O)NH_2$, $-NHC(O)NH(C_{1-4}$ alkyl), $-NHC(O)N(C_{1-4}$ alkyl)$_2$, $-NHSO_2(C_{1-4}$ alkyl), $-SO_2NH_2$, $-SO_2NH(C_{1-4}$ alkyl), $-SO_2N(C_{1-4}$ alkyl)$_2$, $-SO_2NH(CH_2)_2OH$, $-SO_2NH(CH_2)_2O(C_{1-4}$ alkyl), $-CONH_2$, $-CONH(C_{1-4}$ alkyl), $-CON(C_{1-4}$ alkyl)$_2$, $-CH_2CONH_2$, $-(CH_2)_n$-carbocycle, $-O(CH_2)_n$-carbocycle, $-O(CH_2)_n$-heterocycle, and $-(CH_2)_n$-heterocycle comprising carbon atoms and 1-4 heteroatoms selected from N, $NR^8$, O, and $S(O)_p$, wherein said alkyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, $C(O)$carbocycle, $C(O)$heterocycle, $C(O)NR^5R^5$, $C(O)O$-alkyl, $C(O)O$-carbocycle, $C(O)O$-heterocycle, $SO_2$alkyl, $SO_2$carbocycle, $SO_2$heterocycle, $SO_2NR^5R^5$, $-(CH_2)_n$-carbocycle, and $-(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form 4- to 10-membered heterocycle substituted with 0-4 $R^9$;

$R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, $-(CH_2)_nNR^aR^a$, $-(CH_2)_nCONR^aR^a$, $-O(CH_2)_n$heterocycle, $-O(CH_2)_{(2-4)}NR^aR^a$, $-(CR^{10}R^{10})_n$-4-10 membered heterocycle, wherein said alkyl, alkoxyl, and heterocycle are substituted with 0-4 $R^b$;

$R^{10}$ is selected from H and $C_{1-4}$ alkyl;

$R^a$, at each occurrence, is independently selected from H, $C_{1-4}$ alkyl, $-(CH_2)_nOH$, $CO(C_{1-4}$ alkyl), $COCF_3$, $CO_2(C_{1-4}$ alkyl), $-CONH_2$, $-CONH-C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form 4- to 10-membered heterocycle, wherein said alkyl, alkylene, and heterocycle are substituted with 0-4 $R^b$;

$R^b$, at each occurrence, is independently selected from =O, halo, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, $-CONH(C_{1-4}$ alkyl), $-CON(C_{1-4}$ alkyl)$_2$, $-CONH-C_{1-4}$ alkylene-$O(C_{1-4}$ alkyl), $-CONH-C_{1-4}$ alkylene-$N(C_{1-4}$ alkyl)$_2$, $-CONH-C_{1-4}$ alkylene-$N(C_{1-4}$ alkyl)$_2$, $-C_{1-4}$ alkylene-$O-P(O)(OH)_2$, $-NHCO_2(C_{1-4}$ alkyl), $-R^c$, $COR^c$, $CO_2R^c$, and $CONHR^c$;

$R^c$, at each occurrence, is independently selected from $-(CH_2)_n-C_{3-6}$ cycloalkyl, $-(CH_2)_n$-phenyl, and $-(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halo, -OH, $C_{1-4}$ alkyl, $NH_2$, $NH(C_{1-4}$ alkyl), $N(C_{1-4}$ alkyl)$_2$, $C_{1-4}$ alkoxy, and $-NHCO(C_{1-4}$ alkyl), and heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4;

p, at each occurrence, is independently selected from 0, 1, and 2;

provided (1) when L is NHC(O), $R^1$ is other than

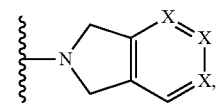

wherein X is N or a substituted or unsubstituted carbon atom;

(2) when L is NH, $R^1$ is other than

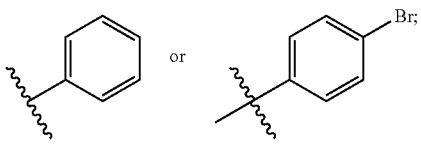 [SMILES: *c1ccccc1 ; *c1ccc(Br)cc1]

(3) when L is O, $R^1$ is other than

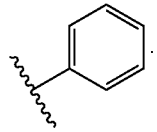

In another aspect, the present invention provides compounds of Formula (V) or stereoisomers, tautomers, pharmaceutically acceptable salts, solvates, or prodrugs thereof, wherein:

L is selected from $-CR^4R^4C(O)-$, $-OC(O)-$, $-NR^6C(O)-$, and $-NR^6-$;

$R^4$, at each occurrence, is independently selected from H and $C_{1-4}$ alkyl; and $R^7$, at each occurrence, is independently selected from H, =O, halogen, $C_{1-4}$ alkyl, $C_{1-4}$ alkoxy, CN, OH, $CF_3$, $-(CH_2)_n-CO_2H$, $-(CH_2)_n-CO_2(C_{1-4}$ alkyl), $-(CH_2)_n-NR^8R^8$, $-NHCO(C_{1-4}$ alkyl), $-NHCOCF_3$, $-NHCO_2(C_{1-4}$ alkyl), $-NHCO_2(CH_2)_2OH$, $-NHC(O)NH_2$, $-NHC(O)NH(C_{1-4}$ alkyl), $-NHC(O)N(C_{1-4}$ alkyl)$_2$, $-NHSO_2(C_{1-4}$ alkyl), $-SO_2NH_2$, $-SO_2NH(C_{1-4}$ alkyl), $-SO_2N(C_{1-4}$ alkyl)$_2$, $-CONH_2$, $-CONH(C_{1-4}$ alkyl), $-CON(C_{1-4}$ alkyl)$_2$, $-CH_2CONH_2$, $-(CH_2)_n$-carbocycle, $-O(CH_2)_n$-carbocycle, $-O(CH_2)_n$-heterocycle, and $-(CH_2)_n$-heterocycle comprising carbon atoms and 1-4 heteroatoms selected from N, $NR^8$, O, and $S(O)_p$, wherein said alkyl, alkoxyl, carbocycle, and heterocycle are substituted with 0-4 $R^9$;

other variables are as defined in Formula (V) above.

In another aspect, the present invention provides compounds of Formula (VI):

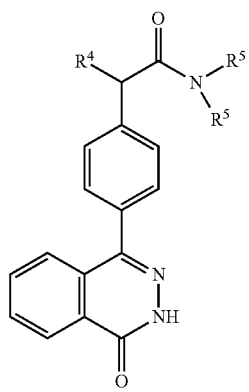

(VI)

or stereoisomers, tautomers, pharmaceutically acceptable salts, solvates, or prodrugs thereof, wherein:

$R^5$, at each occurrence, is independently selected from H, $C_{1-4}$ alkyl, $-(CR^6R^6)_n-C_{3-10}$ carbocycle, and $-(CR^6R^6)_n$-4-10 membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form 4- to 10-membered heterocycle substituted with 1-4 $R^7$;

$R^7$, at each occurrence, is independently selected from H, =O, halogen, $C_{1-4}$ alkyl, $C_{1-4}$ alkoxy, CN, OH, $CF_3$, $-(CH_2)_n-CO_2H$, $-(CH_2)_n-CO_2(C_{1-4}$ alkyl), $-(CH_2)_n-NR^8R^8$, $-NHCO(C_{1-4}$ alkyl), $-NHCOCF_3$, $-NHCO_2(C_{1-4}$ alkyl), $-NHC(O)NH_2$, $-NHC(O)NH(C_{1-4}$ alkyl), $-NHC(O)N(C_{1-4}$ alkyl)$_2$, $-NHSO_2(C_{1-4}$ alkyl), $-SO_2NH_2$, $-SO_2NH(C_{1-4}$ alkyl), $-SO_2N(C_{1-4}$ alkyl)$_2$, $-SO_2NH(CH_2)_2OH$, $-SO_2NH(CH_2)_2O(C_{1-4}$ alkyl), $-CONH_2$, $-CONH(C_{1-4}$ alkyl), $-CON(C_{1-4}$ alkyl)$_2$, $-CH_2CONH_2$ $-(CH_2)_n$-carbocycle, $-O(CH_2)_n$-carbocycle, $-O(CH_2)_n$-heterocycle, and $-(CH_2)_n$-heterocycle comprising carbon atoms and 1-4 heteroatoms selected from N, $NR^8$, O, and $S(O)_p$, wherein said alkyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, $C(O)$carbocycle, $C(O)$heterocycle, $C(O)NR^5R^5$, $C(O)O$-alkyl, $C(O)O$-carbocycle, $C(O)O$-heterocycle, $SO_2$alkyl, $SO_2$carbocycle, $SO_2$heterocycle, $SO_2NR^5R^5$, $-(CH_2)_n$-carbocycle, and $-(CH_2)_n$-heterocycle, wherein said alkyl, carbocycle, and heterocycle are substituted with 0-4 $R^9$;

$R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, $-(CH_2)_nNR^aR^a$, $-(CH_2)_nCONR^aR^a$, $-O(CH_2)_n$heterocycle, $-O(CH_2)_{(2-4)}NR^aR^a$, $-(CR^{10}R^{10})_n$-4-10 membered heterocycle, wherein said alkyl, alkoxyl, and heterocycle are substituted with 0-4 $R^b$;

$R^{10}$ is selected from H and $C_{1-4}$ alkyl;

$R^a$, at each occurrence, is independently selected from H, $C_{1-4}$ alkyl, $-(CH_2)_nOH$, $CO(C_{1-4}$ alkyl), $COCF_3$, $CO_2(C_{1-4}$ alkyl), $-CONH_2$, $-CONH-C_{1-4}$ alkylene-$CO_2(C_{1-4}$ alkyl), $C_{1-4}$ alkylene-$CO_2(C_{1-4}$ alkyl), $R^c$, $CO_2R^c$, and CONHR$^c$; alternatively, $R^a$ and $R^a$ are taken together with the nitrogen atom to which they are attached to form 4- to 10-membered heterocycle, wherein said alkyl, alkylene, and heterocycle are substituted with 0-4 $R^b$;

$R^b$, at each occurrence, is independently selected from =O, halo, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, $-CONH(C_{1-4}$ alkyl), $-CON(C_{1-4}$ alkyl)$_2$, $-CONH-C_{1-4}$ alkylene-$O(C_{1-4}$ alkyl), $-CONH-C_{1-4}$ alkylene-$N(C_{1-4}$ alkyl)$_2$, $-CONH-C_{1-4}$ alkylene-$N(C_{1-4}$ alkyl)$_2$, $-C_{1-4}$ alkylene-$O-P(O)(OH)_2$, $-NHCO_2(C_{1-4}$ alkyl), $-R^c$, $COR^c$, $CO_2R^c$, and CONHR$^c$;

$R^c$, at each occurrence, is independently selected from $-(CH_2)_n-C_{3-6}$ cycloalkyl, $-(CH_2)_n$-phenyl, and $-(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halo, $-OH$, $C_{1-4}$ alkyl, $NH_2$, $NH(C_{1-4}$ alkyl), $N(C_{1-4}$ alkyl)$_2$, $C_{1-4}$ alkoxy, and $-NHCO(C_{1-4}$ alkyl), and heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4;

p, at each occurrence, is independently selected from 0, 1, and 2;

other variables are as defined in Formula (V) above.

In another aspect, the present invention provides compounds of Formula (VI) or stereoisomers, tautomers, pharmaceutically acceptable salts, solvates, or prodrugs thereof, wherein:

$R^5$ is selected from H, $C_{1-4}$ alkyl, $-(CH_2)_n-C_{3-6}$ cycloalkyl, $-(CH_2)_n$-aryl, $-(CH_2)_n$-4-10 membered heterocycle selected from

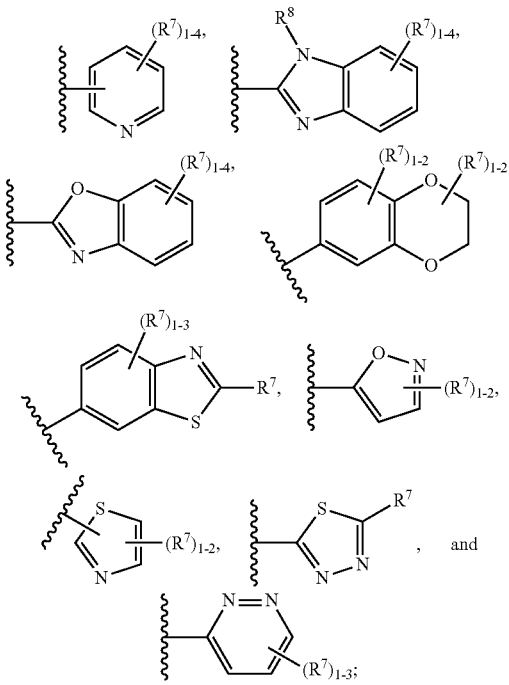

other variables are as defined in Formula (V) above.

In another aspect, the present invention provides compounds of Formula (VI) or stereoisomers, tautomers, pharmaceutically acceptable salts, solvates, or prodrugs thereof, wherein:

R⁵ and R⁵ are taken together with the nitrogen atom to which they are attached to form a heterocycle selected from

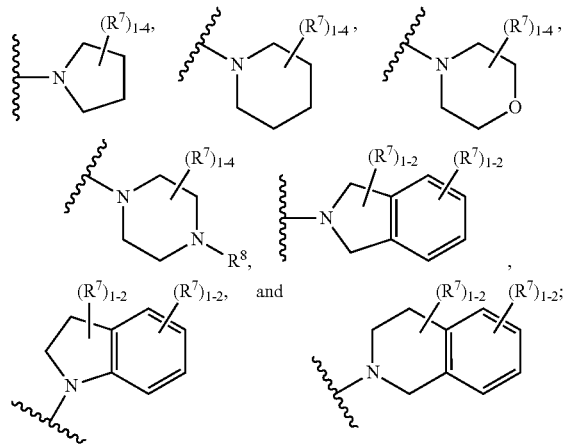

other variables are as defined in Formula (V) above.

In another aspect, the present invention provides compounds of Formula (VII):

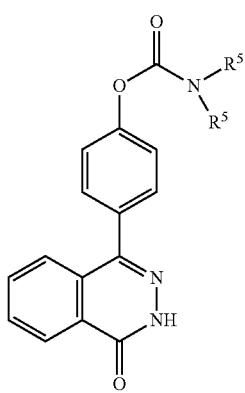

(VII)

or stereoisomers, tautomers, pharmaceutically acceptable salts, solvates, or prodrugs thereof, wherein:

$R^5$, at each occurrence, is independently selected from H, $C_{1-4}$ alkyl, —$(CR^6R^6)_n$—$C_{3-10}$ carbocycle, and —$(CR^6R^6)_n$-4-10 membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form 4- to 10-membered heterocycle substituted with 1-4 $R^7$;

$R^6$, at each occurrence, is independently selected from H and $C_{1-4}$ alkyl;

$R^7$, at each occurrence, is independently selected from H, =O, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —NHCO($C_{1-4}$ alkyl), —$NHCOCF_3$, —$NHCO_2$($C_{1-4}$ alkyl), —$NHC(O)NH_2$, —$NHC(O)NH(C_{1-4}$ alkyl), —$NHC(O)N(C_{1-4}$ alkyl)$_2$, —$NHSO_2(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$CONH_2$, —$CONH(C_{1-4}$ alkyl), —$CON(C_{1-4}$ alkyl)$_2$, —$CH_2CONH_2$, —$(CH_2)_n$-carbocycle, —$O(CH_2)_n$-carbocycle, —$O(CH_2)_n$-heterocycle, and —$(CH_2)_n$-heterocycle, wherein said alkyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, C(O)carbocycle, C(O)heterocycle, $C(O)NR^5R^5$, C(O)O-alkyl, C(O)O-carbocycle, C(O)O-heterocycle, $SO_2$alkyl, $SO_2$carbocycle, $SO_2$heterocycle, $SO_2NR^5R^5$, —$(CH_2)_n$-carbocycle, and —$(CH_2)_n$-heterocycle, wherein said alkyl, carbocycle, and heterocycle are substituted with 0-4 $R^9$;

$R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, —$(CH_2)_nNR^aR^a$, —$(CH_2)_nCONR^aR^a$, —$O(CH_2)_n$heterocycle, —$O(CH_2)_{(2-4)}NR^aR^a$, —$(CR^{10}R^{10})_n$-4-10 membered heterocycle, wherein said alkyl, alkoxyl, and heterocycle are substituted with 0-4 $R^b$;

n, at each occurrence, is independently selected from 0, 1, 2, 3, and 4; and p, at each occurrence, is independently selected from 0, 1, and 2;

other variables are as defined in Formula (V) above.

In another aspect, the present invention provides compounds of Formula (V) or stereoisomers, tautomers, pharmaceutically acceptable salts, solvates, or prodrugs thereof, wherein:

L is —$NR^6$—;

$R^1$ is selected from $C_{3-10}$ carbocycle and 5- to 10-membered heterocycle, wherein said carbocycle and heterocycle are substituted with 1-4 $R^7$;

$R^5$, at each occurrence, is independently selected from H, $C_{1-4}$ alkyl, —$(CR^6R^6)_n$—$C_{3-10}$ carbocycle, and —$(CR^6R^6)_n$-4-10 membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form 4- to 10-membered heterocycle substituted with 1-4 $R^7$;

$R^6$, at each occurrence, is independently selected from H and $C_{1-4}$ alkyl;

$R^7$, at each occurrence, is independently selected from H, =O, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$CH_2NH_2$, —NHCO($C_{1-4}$ alkyl), —$NHCOCF_3$, —$NHCO_2(C_{1-4}$ alkyl), —$NHC(O)NH_2$, —$NHC(O)NH(C_{1-4}$ alkyl), —$NHC(O)N(C_{1-4}$ alkyl)$_2$, —$NHSO_2(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$CONH_2$, —$CONH(C_{1-4}$ alkyl), —$CON(C_{1-4}$ alkyl)$_2$, —$CH_2CONH_2$, —$(CH_2)_n$-carbocycle, —$O(CH_2)_n$-carbocycle, —$O(CH_2)_n$-heterocycle, and —$(CH_2)_n$-heterocycle, wherein said alkyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, C(O)carbocycle, C(O)heterocycle, $C(O)NR^5R^5$, C(O)O-alkyl, C(O)O-carbocycle, C(O)O-heterocycle, $SO_2$alkyl, $SO_2$carbocycle, $SO_2$heterocycle, $SO_2NR^5R^5$, —$(CH_2)_n$-carbocycle, and —$(CH_2)_n$-heterocycle, wherein said alkyl, carbocycle, and heterocycle are substituted with 0-4 $R^9$;

$R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, —$(CH_2)_nNR^aR^a$, —$(CH_2)_nCONR^aR^a$, —$O(CH_2)_n$heterocycle, —$O(CH_2)_{(2-4)}NR^aR^a$, —$(CR^{10}R^{10})_n$-4-10 membered heterocycle, wherein said alkyl, alkoxyl, and heterocycle are substituted with 0-4 $R^b$;

n, at each occurrence, is independently selected from 0, 1, 2, 3, and 4;

p, at each occurrence, is independently selected from 0, 1, and 2;

other variables are as defined in Formula (V) above.

In another aspect, the present invention provides compounds of Formula (V) or stereoisomers, tautomers, pharmaceutically acceptable salts, solvates, or prodrugs thereof, wherein:

L is —NR$^6$—; and

R$^1$ is selected from

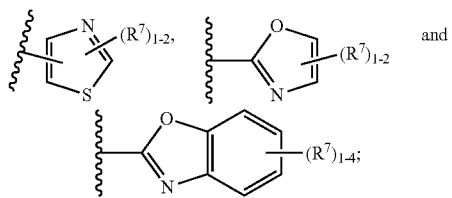

other variables are as defined in Formula (V) above.

In still another aspect, the present invention provides compounds of Formula (VIII):

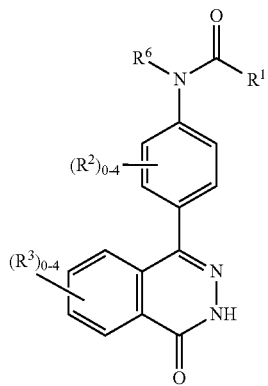

(VIII)

or stereoisomers, tautomers, pharmaceutically acceptable salts, solvates, or prodrugs thereof, wherein:

R$^1$ is selected from NR$^5$R$^5$, C$_{3-10}$ carbocycle, and 5- to 10-membered heterocycle, wherein said carbocycle and heterocycle are substituted with 1-4 R$^7$;

R$^5$, at each occurrence, is independently selected from H, C$_{1-4}$ alkyl, —(CR$^6$R$^6$)$_n$—C$_{3-10}$ carbocycle, and —(CR$^6$R$^6$)$_n$- 4-10 membered heterocycle comprising carbon atoms and 1-4 heteroatoms selected from N, NR$^8$, O, and S(O)$_p$, wherein said alkyl, carbocycle, and heterocycle are substituted with 1-4 R$^7$;

alternatively, R$^5$ and R$^5$ are taken together with the nitrogen atom to which they are attached to form 4- to 10-membered heterocycle substituted with 1-4 R$^7$;

R$^6$, at each occurrence, is independently selected from H and C$_{1-4}$ alkyl;

R$^7$, at each occurrence, is independently selected from H, =O, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHC(O)NH$_2$, —NHC(O)NH(C$_{1-4}$ alkyl), —NHC(O)N(C$_{1-4}$ alkyl)$_2$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —CONH$_2$, —CONH(C$_{1-4}$ alkyl), —CON(C$_{1-4}$ alkyl)$_2$, —CH$_2$CONH$_2$, —(CH$_2$)$_n$-carbocycle, —O(CH$_2$)$_n$-carbocycle, —O(CH$_2$)$_n$-heterocycle, and —(CH$_2$)$_n$-heterocycle, wherein said alkyl, alkoxyl, carbocycle, and heterocycle are substituted with 0-4 R$^9$;

R$^8$, at each occurrence, is independently selected from H, C$_{1-4}$ alkyl, C(O)C$_{1-4}$alkyl, C(O)carbocycle, C(O)heterocycle, C(O)NR$^5$R$^5$, C(O)O-alkyl, C(O)O-carbocycle, C(O)O-heterocycle, SO$_2$alkyl, SO$_2$carbocycle, SO$_2$heterocycle, SO$_2$NR$^5$R$^5$, —(CH$_2$)$_n$-carbocycle, and —(CH$_2$)$_n$-heterocycle, wherein said alkyl, carbocycle, and heterocycle are substituted with 0-4 R$^9$;

R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —O(CH$_2$)$_n$heterocycle, —O(CH$_2$)$_{(2-4)}$NR$^a$R$^a$, —(CR$^{10}$R$^{10}$)$_n$-4-10 membered heterocycle, wherein said alkyl, alkoxyl, and heterocycle are substituted with 0-4 R$^b$;

n, at each occurrence, is independently selected from 0, 1, 2, 3, and 4;

p, at each occurrence, is independently selected from 0, 1, and 2;

other variables are as defined in Formula (V) above.

In still another aspect, the present invention provides compounds of Formula (VIII), or stereoisomers, tautomers, pharmaceutically acceptable salts, solvates, or prodrugs thereof, wherein:

R$^1$ is selected from

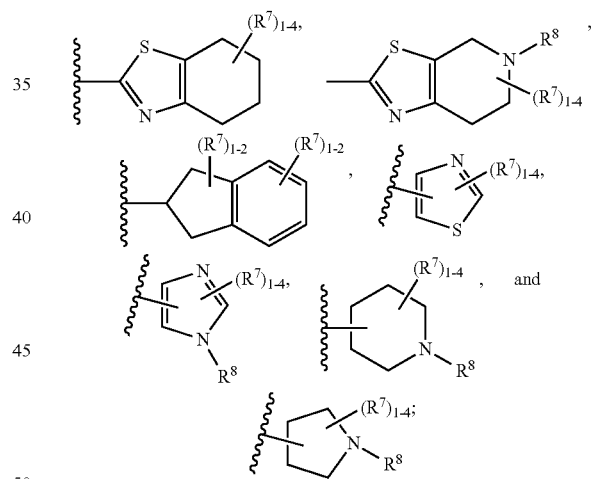

R$^7$, at each occurrence, is independently selected from H, =O, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —CH$_2$NH$_2$, —NHCO(C$_{1-4}$ alkyl), —NHCOCF$_3$, —NHCO$_2$(C$_{1-4}$ alkyl), —NHC(O)NH$_2$, —NHC(O)NH(C$_{1-4}$ alkyl), —NHC(O)N(C$_{1-4}$ alkyl)$_2$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —CONH$_2$, —CONH(C$_{1-4}$ alkyl), —CON(C$_{1-4}$ alkyl)$_2$, —CH$_2$CONH$_2$, —(CH$_2$)$_n$-carbocycle, —O(CH$_2$)$_n$-carbocycle, —O(CH$_2$)$_n$-heterocycle, and —(CH$_2$)$_n$-heterocycle comprising carbon atoms and 1-4 heteroatoms selected from N, NR$^8$, O, and S(O)$_p$, wherein said alkyl, alkoxyl, carbocycle, and heterocycle are substituted with 0-4 R$^9$;

R$^8$, at each occurrence, is independently selected from H, C$_{1-4}$ alkyl, C(O)C$_{1-4}$alkyl, C(O)carbocycle, C(O)heterocycle, C(O)NR$^5$R$^5$, C(O)O-alkyl, C(O)O-carbocycle, C(O)O-heterocycle, SO$_2$alkyl, SO$_2$carbocycle, SO$_2$heterocycle, SO$_2$NR$^5$R$^5$, —(CH$_2$)$_n$-carbocycle, and —(CH$_2$)$_n$-heterocycle, wherein said alkyl, carbocycle, and heterocycle are substituted with 0-4 R$^9$; and R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —O(CH$_2$)$_n$heterocycle, —O(CH$_2$)$_{(2-4)}$NR$^a$R$^a$, —(CR$^{10}$R$^{10}$)$_n$-4-10 membered heterocycle, wherein said alkyl, alkoxyl, and heterocycle are substituted with 0-4 R$^b$;

other variables are as defined in Formula (V) above.

In still another aspect, the present invention provides compounds of Formula (VIII), or stereoisomers, tautomers, pharmaceutically acceptable salts, solvates, or prodrugs thereof, wherein:

R$^1$ is NR$^5$R$^5$;

R$^5$, at each occurrence, is independently selected from H, C$_{1-4}$ alkyl, —(CR$^6$R$^6$)$_n$—C$_{3-10}$ carbocycle, and —(CR$^6$R$^6$)$_n$-4-10 membered heterocycle comprising carbon atoms and 1-4 heteroatoms selected from N, NR$^8$, O, and S(O)$_p$, wherein said alkyl, carbocycle, and heterocycle are substituted with 1-4 R$^7$;

alternatively, R$^5$ and R$^5$ are taken together with the nitrogen atom to which they are attached to form 4- to 10-membered heterocycle substituted with 1-4 R$^7$;

R$^6$, at each occurrence, is independently selected from H and C$_{1-4}$ alkyl;

R$^7$, at each occurrence, is independently selected from H, =O, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHC(O)NH$_2$, —NHC(O)NH(C$_{1-4}$ alkyl), —NHC(O)N(C$_{1-4}$ alkyl)$_2$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —CONH$_2$, —CONH(C$_{1-4}$ alkyl), —CON(C$_{1-4}$ alkyl)$_2$, —CH$_2$CONH$_2$, —(CH$_2$)$_n$-carbocycle, —O(CH$_2$)$_n$-carbocycle, —O(CH$_2$)$_n$-heterocycle, and —(CH$_2$)$_n$-heterocycle comprising carbon atoms and 1-4 heteroatoms selected from N, NR$^8$, O, and S(O)$_p$, wherein said alkyl, alkoxyl, carbocycle, and heterocycle are substituted with 0-4 R$^9$;

R$^8$, at each occurrence, is independently selected from H, C$_{1-4}$ alkyl, C(O)C$_{1-4}$alkyl, C(O)carbocycle, C(O)heterocycle, C(O)NR$^5$R$^5$, C(O)O-alkyl, C(O)O-carbocycle, C(O)O-heterocycle, SO$_2$alkyl, SO$_2$carbocycle, SO$_2$heterocycle, SO$_2$NR$^5$R$^5$, —(CH$_2$)$_n$-carbocycle, and —(CH$_2$)$_n$-heterocycle, wherein said alkyl, carbocycle, and heterocycle are substituted with 0-4 R$^9$; and R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —O(CH$_2$)$_n$heterocycle, —O(CH$_2$)$_{(2-4)}$NR$^a$R$^a$, —(CR$^{10}$R$^{10}$)$_n$-4-10 membered heterocycle, wherein said alkyl, alkoxyl, and heterocycle are substituted with 0-4 R$^b$;

other variables are as defined in Formula (V) above.

In one embodiment, the present invention provides compounds of Formulae (I), (II), (III), and (IV), or stereoisomers, tautomers, pharmaceutically acceptable salts, solvates, or prodrugs thereof, wherein M is N or CR$^{10}$; L is selected from —CR$^4$R$^4$C(O)—, —OC(O)—, —NR$^6$C(O)—, and —NR$^6$—; R$^1$ is selected from OC$_{1-4}$ alkyl, NR$^5$R$^5$, C$_{3-10}$ carbocycle and 4- to 12-membered heterocycle comprising carbon atoms and 1-4 heteroatoms selected from N, NR$^8$, O, and S(O)$_p$; wherein said alkyl, carbocycle and heterocycle are substituted with 1-4 R$^7$.

In one embodiment, the present invention provides compounds of Formulae (I), (II), (III), (IV), (V), (VI), (VII), and (VIII), or stereoisomers, tautomers, pharmaceutically acceptable salts, solvates, or prodrugs thereof, wherein L is selected from —CR$^4$R$^4$C(O)—, —OC(O)—, —NR$^6$C(O)—, and —NR$^6$—; R$^1$ is selected from OC$_{1-4}$ alkyl, NR$^5$R$^5$, C$_{3-10}$ carbocycle and 4- to 12-membered heterocycle comprising carbon atoms and 1-4 heteroatoms selected from N, NR$^8$, O, and S(O)$_p$; wherein said alkyl, carbocycle and heterocycle are substituted with 1-4 R$^7$.

In one embodiment, the present invention provides compounds of Formulae (I), (IV), (V), and (VIII), or stereoisomers, tautomers, pharmaceutically acceptable salts, solvates, or prodrugs thereof, wherein L is selected from —NR$^6$C(O)—, and —NR$^6$—; R$^1$ is 4- to 12-membered heterocycle comprising carbon atoms and 1-4 heteroatoms selected from N, NR$^8$, O, and S(O)$_p$ and substituted with 1-4 R$^7$.

In one embodiment, the present invention provides compounds of Formulae (I), (IV), (V), and (VIII), or stereoisomers, tautomers, pharmaceutically acceptable salts, solvates, or prodrugs thereof, wherein L is selected from —NR$^6$C(O)— or NR$^6$—; R$^1$ is selected from

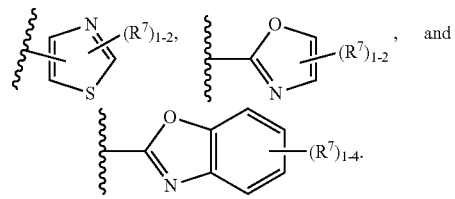

In one embodiment, the present invention provides compounds of Formulae (I), (IV), (V), and (VIII), or stereoisomers, tautomers, pharmaceutically acceptable salts, solvates, or prodrugs thereof, wherein L is selected from —NR$^6$C(O)—, and —NR$^6$—; R$^1$ is C$_{3-10}$ carbocycle substituted with 1-4 R$^7$ substituted with 1-4 R$^7$.

In one embodiment, the present invention provides compounds of Formulae (I), (IV), (V), and (VIII), or stereoisomers, tautomers, pharmaceutically acceptable salts, solvates, or prodrugs thereof, wherein L is selected from —NR$^6$C(O)—, and —NR$^6$—; R$^1$ is C$_{3-6}$ cycloalkyl substituted with 1-4 R$^7$ or aryl substituted with 1-4 R$^7$; R$^7$, at each occurrence, is independently selected from H, =O, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NH$_2$, —NHC(O)NH(C$_{1-4}$ alkyl), —NHC(O)N(C$_{1-4}$ alkyl)$_2$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —CONH$_2$, —CONH(C$_{1-4}$ alkyl), —CON(C$_{1-4}$ alkyl)$_2$, —CH$_2$CONH$_2$, —(CH$_2$)$_n$-carbocycle, —O(CH$_2$)$_n$-carbocycle, —O(CH$_2$)$_n$-heterocycle, and —(CH$_2$)$_n$-heterocycle comprising carbon atoms and 1-4 heteroatoms selected from N, NR$^8$, O, and S(O)$_p$, wherein said alkyl, alkoxyl, carbocycle, and heterocycle are substituted with 0-4 R$^9$.

In one embodiment, the present invention provides compounds of Formulae (I), (IV), (V), and (VIII), or stereoisomers, tautomers, pharmaceutically acceptable salts, solvates, or prodrugs thereof, wherein L is selected from —NR$^6$C(O)—, and —NR$^6$—; R$^1$ is cyclopropyl, cyclobutyl, cyclopentyl, cyclohexyl or phenyl, each substituted with 1-4 $R^7$; $R^7$, at each occurrence, is independently selected from H, =O, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2$ ($C_{1-4}$ alkyl), —$NHCO_2(CH_2)_2O(C_{1-4}$ alkyl), —$NHCO_2$ $(CH_2)_3O(C_{1-4}$ alkyl), —$NHCO_2(CH_2)_2OH$, —$NHCO_2$ $(CH_2)_2$ $NH_2$, —$NHCO_2(CH_2)_2N(C_{1-4}$ alkyl$)_2$, —$NHCO_2CH_2CO_2H$, —$CH_2NHCO_2(C_{1-4}$ alkyl), —NHC(O)$NH_2$, —NHC(O)NH($C_{1-4}$ alkyl), —NHC(O)N($C_{1-4}$ alkyl$)_2$, —$NHSO_2(C_{1-4}$ alkyl), —$SO_2NH_2$, —$SO_2NH(C_{1-4}$ alkyl), —$SO_2N(C_{1-4}$ alkyl$)_2$, —$SO_2NH(CH_2)_2OH$, —$SO_2NH(CH_2)_2O(C_{1-4}$ alkyl), —$CONH_2$, —CONH($C_{1-4}$ alkyl), —CON($C_{1-4}$ alkyl$)_2$, —$CH_2CONH_2$, —$(CH_2)_n$-carbocycle, —$O(CH_2)_n$-carbocycle, —$O(CH_2)_n$-heterocycle, and —$(CH_2)_n$-heterocycle comprising carbon atoms and 1-4 heteroatoms selected from N, $NR^8$, O, and $S(O)_p$, wherein said alkyl, alkoxyl, carbocycle, and heterocycle are substituted with 0-4 $R^9$.

In one embodiment, the present invention provides compounds of Formulae (I), (II), (III), (IV), (V), (VI), (VII), and (VIII), or stereoisomers, tautomers, pharmaceutically acceptable salts, solvates, or prodrugs thereof, wherein L is selected from —$CR^4R^4C(O)$—, —OC(O)—, and —$NR^6C(O)$—; $R^1$ is $NR^5R^5$; $R^5$, at each occurrence, is independently selected from H, $C_{1-4}$ alkyl, —$(CR^6R^6)_n$—$C_{3-10}$ carbocycle, and —$(CR^6R^6)_n$-4-10 membered heterocycle comprising carbon atoms and 1-4 heteroatoms selected from N, $NR^8$, O, and $S(O)_p$, wherein said carbocycle and heterocycle are substituted with 1-4 $R^7$.

In one embodiment, the present invention provides compounds of Formulae (I), (II), (III), (IV), (V), (VI), (VII), and (VIII), or stereoisomers, tautomers, pharmaceutically acceptable salts, solvates, or prodrugs thereof, wherein L is selected from —$CR^4R^4C(O)$—, —OC(O)—, and —$NR^6C(O)$—; $R^1$ is $NR^5R^5$; $R^5$, at each occurrence, is independently selected from H, $C_{1-4}$ alkyl, —$(CH_2)_n$—$C_{3-6}$ cycloalkyl, —$(CH_2)_n$-aryl, —$(CH_2)_n$-4-10 membered heterocycle selected

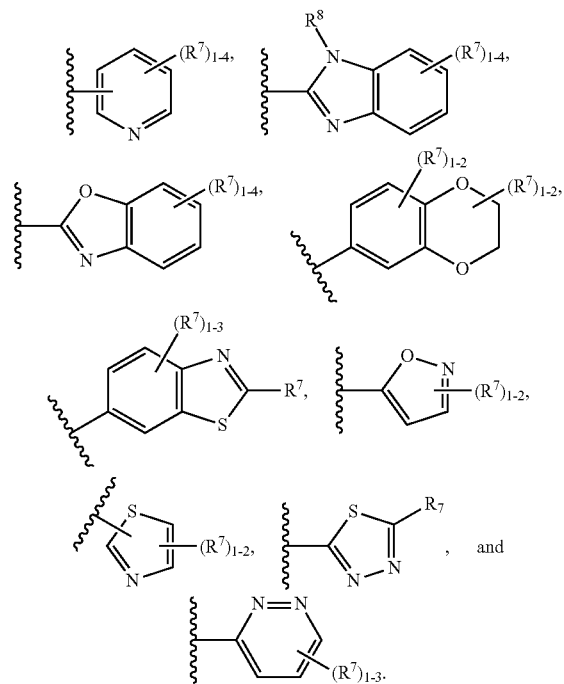

In one embodiment, the present invention provides compounds of Formulae (I), (II), (III), (IV), (V), (VI), (VII), and (VIII), or stereoisomers, tautomers, pharmaceutically acceptable salts, solvates, or prodrugs thereof, wherein L is selected from —$CR^4R^4C(O)$—, —OC(O)—, and —$NR^6C(O)$—; $R^1$ is $NR^5R^5$; $R^5$ and $R^5$ are taken together with the nitrogen atom to which they are attached to form 4- to 10-membered heterocycle comprising carbon atoms and 1-4 heteroatoms selected from N, $NR^8$, O, and $S(O)_p$, wherein said heterocycle is substituted with 1-4 $R^7$.

In one embodiment, the present invention provides compounds of Formulae (I), (II), (III), (IV), (V), (VI), (VII), and (VIII), or stereoisomers, tautomers, pharmaceutically acceptable salts, solvates, or prodrugs thereof, wherein L is selected from —$CR^4R^4C(O)$—, —OC(O)—, and $NR^6C(O)$—; $R^1$ is $NR^5R^5$; $R^5$ and $R^5$ are taken together with the nitrogen atom to which they are attached to form a heterocycle selected from

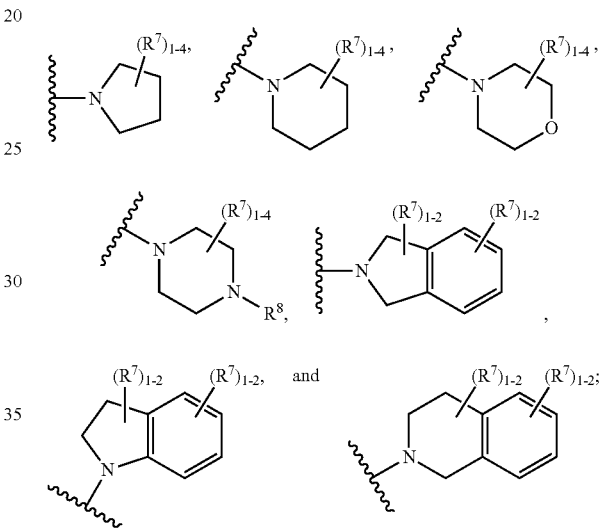

$R^7$, at each occurrence, is independently selected from H, =O, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2$ ($C_{1-4}$ alkyl), —$NHCO_2(CH_2)_2O(C_{1-4}$ alkyl), —$NHCO_2$ $(CH_2)_3O(C_{1-4}$ alkyl), —$NHCO_2(CH_2)_2OH$, —$NHCO_2$ $(CH_2)_2$ $NH_2$, —$NHCO_2(CH_2)_2N(C_{1-4}$ alkyl$)_2$, —$NHCO_2CH_2CO_2H$, —$CH_2NHCO_2(C_{1-4}$ alkyl), —NHC(O)$NH_2$, —NHC(O)NH($C_{1-4}$ alkyl), —NHC(O)N($C_{1-4}$ alkyl$)_2$, —$NHSO_2(C_{1-4}$ alkyl), —$SO_2NH_2$, —$SO_2NH(C_{1-4}$ alkyl), —$SO_2N(C_{1-4}$ alkyl$)_2$, —$SO_2NH(CH_2)_2OH$, —$SO_2NH(CH_2)_2O(C_{1-4}$ alkyl), —$CONH_2$, —CONH($C_{1-4}$ alkyl), —CON($C_{1-4}$ alkyl$)_2$, —$CH_2CONH_2$, —$(CH_2)_n$-carbocycle, —$O(CH_2)_n$-carbocycle, —$O(CH_2)_n$-heterocycle, and —$(CH_2)_n$-heterocycle comprising carbon atoms and 1-4 heteroatoms selected from N, $NR^8$, O, and $S(O)_p$, wherein said alkyl, alkoxyl, carbocycle, and heterocycle are substituted with 0-4 $R^9$.

In one embodiment, the present invention provides compounds of Formulae (I), (II), (III), (IV), (V), (VI), (VII), and (VIII), or stereoisomers, tautomers, pharmaceutically acceptable salts, solvates, or prodrugs thereof, wherein L is selected from —$CR^4R^4C(O)$—, —OC(O)—, —$NR^6C(O)$—, and —$NR^6$—; $R^1$ is selected from

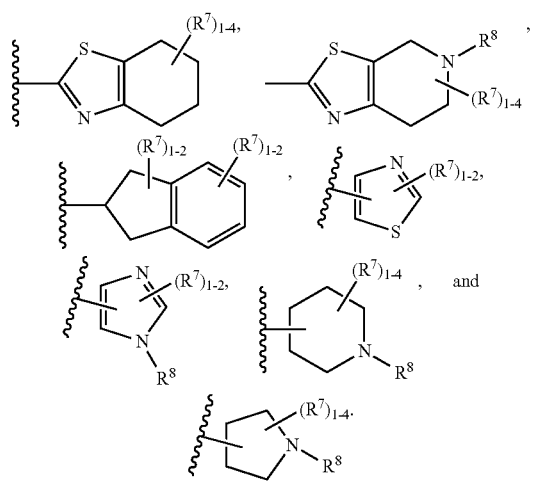

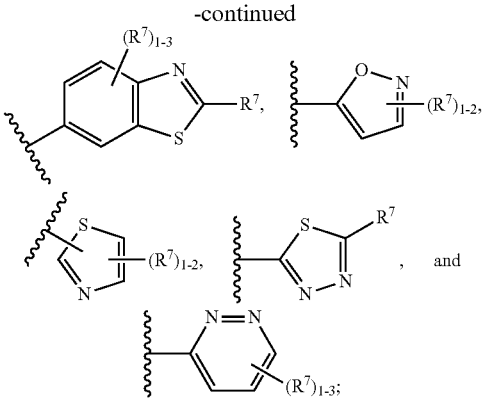

In one embodiment, the present invention provides compounds of Formulae (I), (II), (III), (IV), (V), (VI), (VII), and (VIII), or stereoisomers, tautomers, pharmaceutically acceptable salts, solvates, or prodrugs thereof, wherein L is selected from —$CR^4R^4C(O)$—, —$OC(O)$—, —$NR^6C(O)$—, and —$NR^6$—; $R^1$ is selected from $OC_{1-4}$ alkyl, $NR^5R^5$, $C_{3-10}$ carbocycle and 4- to 12-membered heterocycle comprising carbon atoms and 1-4 heteroatoms selected from N, $NR^8$, O, and $S(O)_p$; wherein said alkyl, carbocycle and heterocycle are substituted with 1-4 $R^7$; $R^5$, at each occurrence, is independently selected from H, $C_{1-4}$ alkyl, —$(CR^6R^6)_n$—$C_{3-10}$ carbocycle, and —$(CR^6R^6)_n$-4-10 membered heterocycle comprising carbon atoms and 1-4 heteroatoms selected from N, $NR^8$, O, and $S(O)_p$, wherein said alkyl, carbocycle and heterocycle are substituted with 1-4 $R^7$; alternatively, $R^5$ and $R^5$ are taken together with the nitrogen atom to which they are attached to form 4- to 10-membered heterocycle substituted with 1-4 $R^7$.

In one embodiment, the present invention provides compounds of Formulae (I), (II), (III), (IV), (V), (VI), (VII), and (VIII), or stereoisomers, tautomers, pharmaceutically acceptable salts, solvates, or prodrugs thereof, wherein L is selected from —$CR^4R^4C(O)$—, —$OC(O)$—, —$NR^6C(O)$—, and —$NR^6$—; $R^1$ is selected from $OC_{1-4}$ alkyl, $C_{3-10}$ carbocycle and 4- to 12-membered heterocycle comprising carbon atoms and 1-4 heteroatoms selected from N, $NR^8$, O, and $S(O)_p$; wherein said carbocycle and heterocycle are substituted with 1-4 $R^7$; $R^5$, at each occurrence, is independently selected from H, $C_{1-4}$ alkyl, —$(CR^6R^6)_n$—$C_{3-10}$ carbocycle substituted with 1-4 $R^7$, and —$(CR^6R^6)_n$-4-10 membered heterocycle selected from

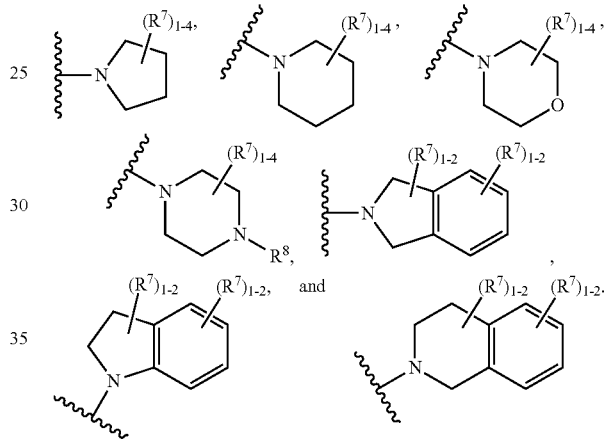

alternatively, $R^5$ and $R^5$ are taken together with the nitrogen atom to which they are attached to form a heterocycle selected from

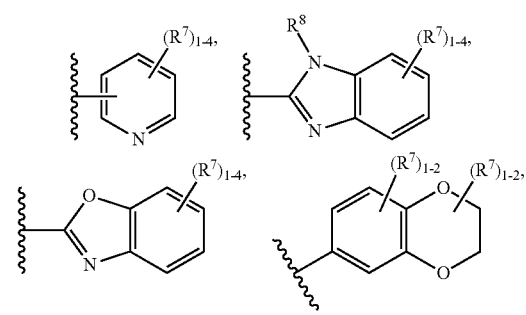

In another aspect, the present invention provides a compound selected from any subset list of compounds exemplified in the present application.

In another embodiment, the compounds of the present invention have ROCK IC50 values ≤10 μM.

In another embodiment, the compounds of the present invention have ROCK IC50 values ≤1 μM.

In another embodiment, the compounds of the present invention have ROCK IC50 values ≤0.1 μM.

In another embodiment, the compounds of the present invention have ROCK IC50 values ≤0.05 μM.

In another embodiment, the compounds of the present invention have ROCK IC50 values ≤0.01 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a patient that has not yet presented with a clinical disease state, whereas secondary prevention is defined as preventing a second occurrence of the same or similar clinical disease state. In another embodiment, the present invention provides a combined preparation of a compound of the present invention and additional therapeutic agent(s) for simultaneous, separate or sequential use in therapy.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

II. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0] bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary* (13th Edition), J. Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me Methyl
Et Ethyl
Pr Propyl
i-Pr Isopropyl
Bu Butyl
i-Bu Isobutyl
t-Bu tert-butyl
Ph Phenyl
Bn Benzyl
Boc tert-butyloxycarbonyl
AcOH or HOAc acetic acid
AlCl$_3$ aluminum chloride
AIBN Azobisisobutyronitrile
BBr$_3$ boron tribromide
BCl$_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz Carbobenzyloxy
CH$_2$Cl$_2$ Dichloromethane
CH$_3$CN or ACN Acetonitrile
CDCl$_3$ deutero-chloroform
CHCl$_3$ Chloroform
mCPBA or m-CPBA meta-chloroperbenzoic acid
Cs$_2$CO$_3$ cesium carbonate
Cu(OAc)$_2$ copper (II) acetate
Cy$_2$NMe N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or diisopropylethylamine
Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I)trifluoromethanesulfonate
Et$_3$N or TEA triethylamine
EtOAc ethyl acetate
Et$_2$O diethyl ether
EtOH Ethanol
GMF glass microfiber filter
Grubbs (II) (1,3-bis(2,4,6-trimethylphenyl)-2-imidazolidinylidene)dichloro(phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex Hexane
HOBt or HOBT 1-hydroxybenzotriazole
H$_2$SO$_4$ sulfuric acid
K$_2$CO$_3$ potassium carbonate
KOAc potassium acetate
K$_3$PO$_4$ potassium phosphate
LAH lithium aluminum hydride
LG leaving group
LiOH lithium hydroxide
MeOH Methanol
MgSO$_4$ magnesium sulfate
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NCS N-chlorosuccinimide
NH$_3$ Ammonia
NH$_4$Cl ammonium chloride
NH$_4$OH ammonium hydroxide
OTf triflate or trifluoromethanesulfonate
Pd$_2$(dba)$_3$ tris(dibenzylideneacetone)dipalladium(0)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride
PG protecting group POCl$_3$ phosphorus oxychloride
i-PrOH or IPA isopropanol
PS polystyrene
SEM-Cl 2-(trimethysilyl)ethoxymethyl chloride
SiO$_2$ silica oxide
SnCl$_2$ tin(II) chloride
TBAI tetra-n-butylammonium iodide
TEA triethylamine
TFA trifluoroacetic acid
THF tetrahydrofuran
TMSCHN$_2$ trimethylsilyldiazomethane
T3P propane phosphonic acid anhydride
TRIS tris(hydroxymethyl)aminomethane The compounds of the present invention can be prepared in a number of ways known to one skilled in the art of organic synthesis.

IV. Biology

In Vitro Assays

The effectiveness of compounds of the present invention as ROCK inhibitors can be determined in a 30 μL assay containing 20 mM HEPES, pH 7.5, 20 mM MgCl$_2$, 0.015% Brij-35, 4 mM DTT, 5 μM ATP and 1.5 μM peptide substrate (FITC-AHA-AKRRRLSSLRA-OH). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LabChip 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the IC$_{50}$; i.e., the concentration of compound required to inhibit 50% of kinase activity."

Representative Examples were tested in the ROCK assay described above and found having ROCK inhibitory activity. A range of ROCK inhibitory activity (IC50 values) of ≤50 μM (50000 nM) was observed. Table A below lists the ROCK IC50 values measured for the following examples.

TABLE A

| Example No. | ROCK1 IC50 (nM) | ROCK2 IC50 (nM) |
|---|---|---|
| 2 | 679 | 30 |
| 10 | 729 | 17 |
| 13 | 16200 | 9733 |
| 19 | 6482 | 5834 |
| 33 | 23 | 1.2 |
| 34 | 11940 | 553 |
| 48 | 670 | 39 |
| 52 | 544 | 225 |
| 58 | 35 | 0.3 |
| 61 | 49 | 2.1 |
| 67 | 175 | 14 |
| 69 | 50000 | 894 |
| 76 | 20 | 1.2 |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by methods available to those skilled in the art of organic chemistry (Maffrand, J. P. et al., *Heterocycles,* 16(1): 35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis,* 4th Edition, Wiley-Interscience (2006)).

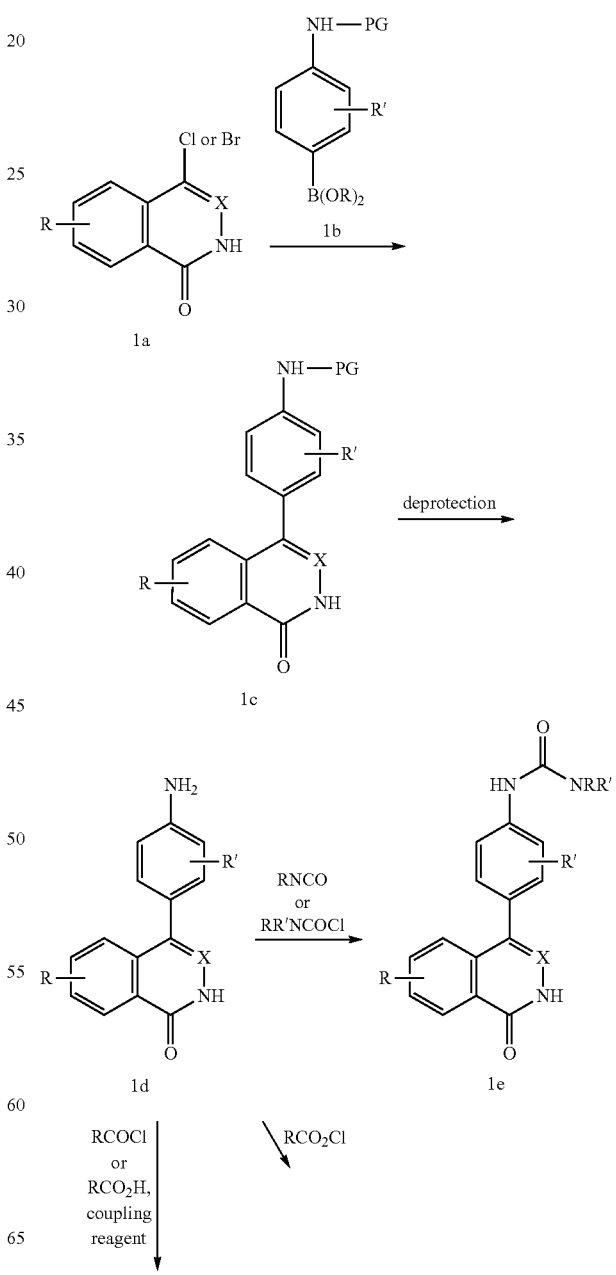

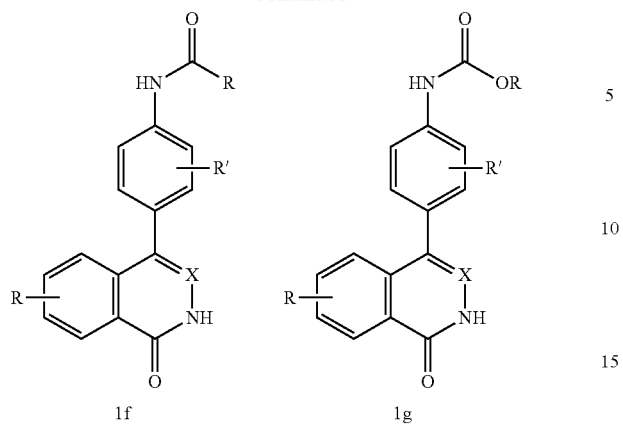

1f          1g

X = CR, N

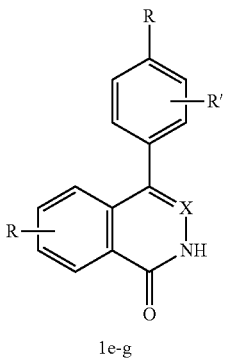

1e-g

X = N, CR

Scheme 1 shows the synthesis of generic compounds 1e, 1f, 1g, from the common intermediate 1d. Suzuki-Miyaura coupling between aryl halide 1a and boronic acid or boronate ester (1b) in the presence of a base such as $K_3PO_4$ and a catalyst such as $Pd(PPh_3)_4$ affords intermediate 1c. Cleavage of the protecting group, such as using TFA or HCl in dioxane when PG=Boc, affords the arylamine intermediate 1d. Intermediate 1d is converted to the urea target 1e by treatment with an isocyanate or a carbamic chloride. Intermediate 1d is converted to the amide target 1f by treatment with an acid chloride in the presence of a base such as pyridine or DIEA. Alternatively, Target 1f is prepared by coupling of intermediate 1d with a carboxylic acid in the presence of a coupling reagent, such as HATU or BOP, and a base such as DIEA. Intermediate 1d is converted to the carbamate target 1g by treatment with a chloroformate in the presence of a base such as DIEA or TEA.

Alternatively, targets 1e-g can be prepared as shown in Scheme 2. Aryl halide 2a (commercially available or prepared by literature methods) is converted to the aryl boronic acid or boronate ester 2b by coupling with bis(pinacolato)diboron in the presence of a base such a potassium acetate and a catalyst such as $PdCl_2(dppf)$ in dioxane or DMSO. Suzuki-Miyaura coupling between aryl halide 1a and boronic acid or boronate ester (2b) in the presence of a base such as $K_3PO_4$ and a catalyst such as $Pd(PPh_3)_4$ affords target compounds 1e-g.

Scheme 3.

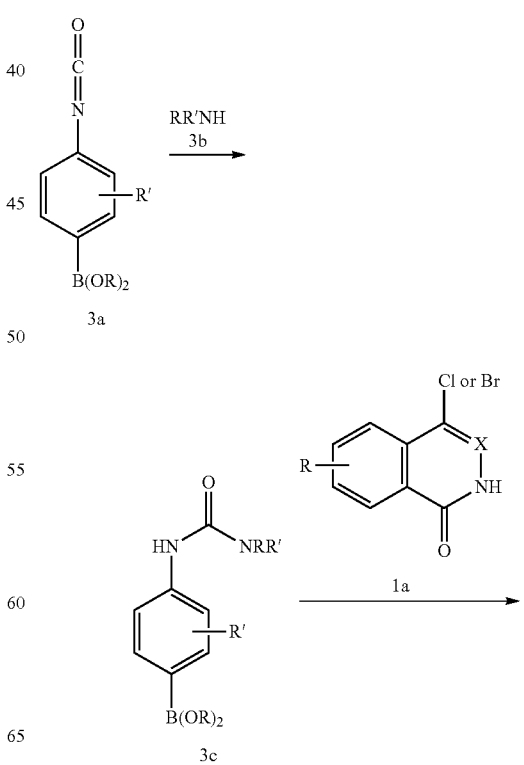

Scheme 2.

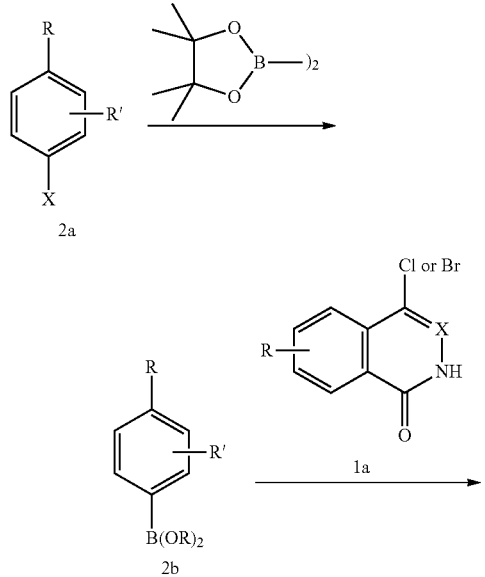

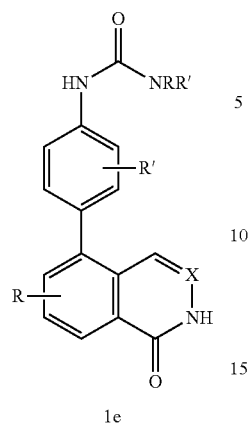

X = N, CR     1e

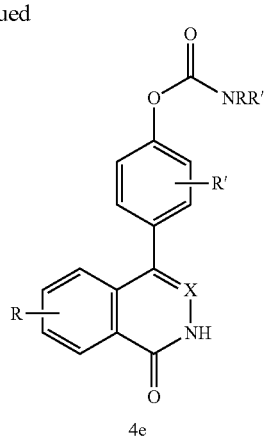

X = N, CR     4e

Alternatively, target 1e can be prepared as shown in Scheme 3 beginning from isocyanate 3a, which is either commercially available or can be prepared from the aniline precursor upon treatment with phosgene (or equivalent) and an appropriate base such as TEA. Intermediate 3a is reacted with amine (3b) to afford urea 3c. Suzuki-Miyaura coupling between aryl halide 1a and boronic acid or boronate ester (3c) in the presence of a base such as $K_3PO_4$ and a catalyst such as $Pd(PPh_3)_4$ affords target compounds 1e.

Scheme 4 shows the synthesis of carbamate target 4e, beginning from chloroformate 4a (either commercially available or prepared by treatment of an appropriate halophenol with phosgene or a phosgene equivalent). Intermediate 4a is reacted with an amine (4b) in the presence of a base such as TEA to afford carbamate 4c. Aryl halide 4c is converted to the aryl boronic acid or boronate ester 4d by coupling with bis(pinacolato)diboron in the presence of a base such a potassium acetate and a catalyst such as $PdCl_2(dppf)$ in dioxane or DMSO. Suzuki-Miyaura coupling between aryl halide 1a and boronic acid or boronate ester (4d) in the presence of a base such as $K_3PO_4$ and a catalyst such as $Pd(PPh_3)_4$ affords target compound 4e.

Scheme 4.

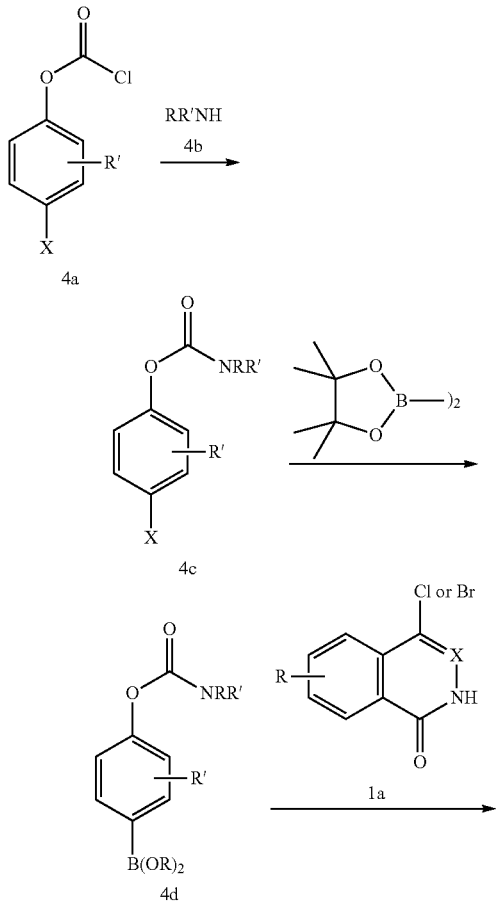

Scheme 5.

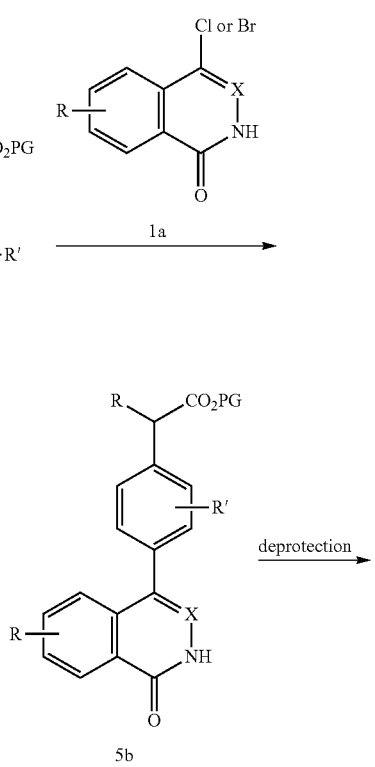

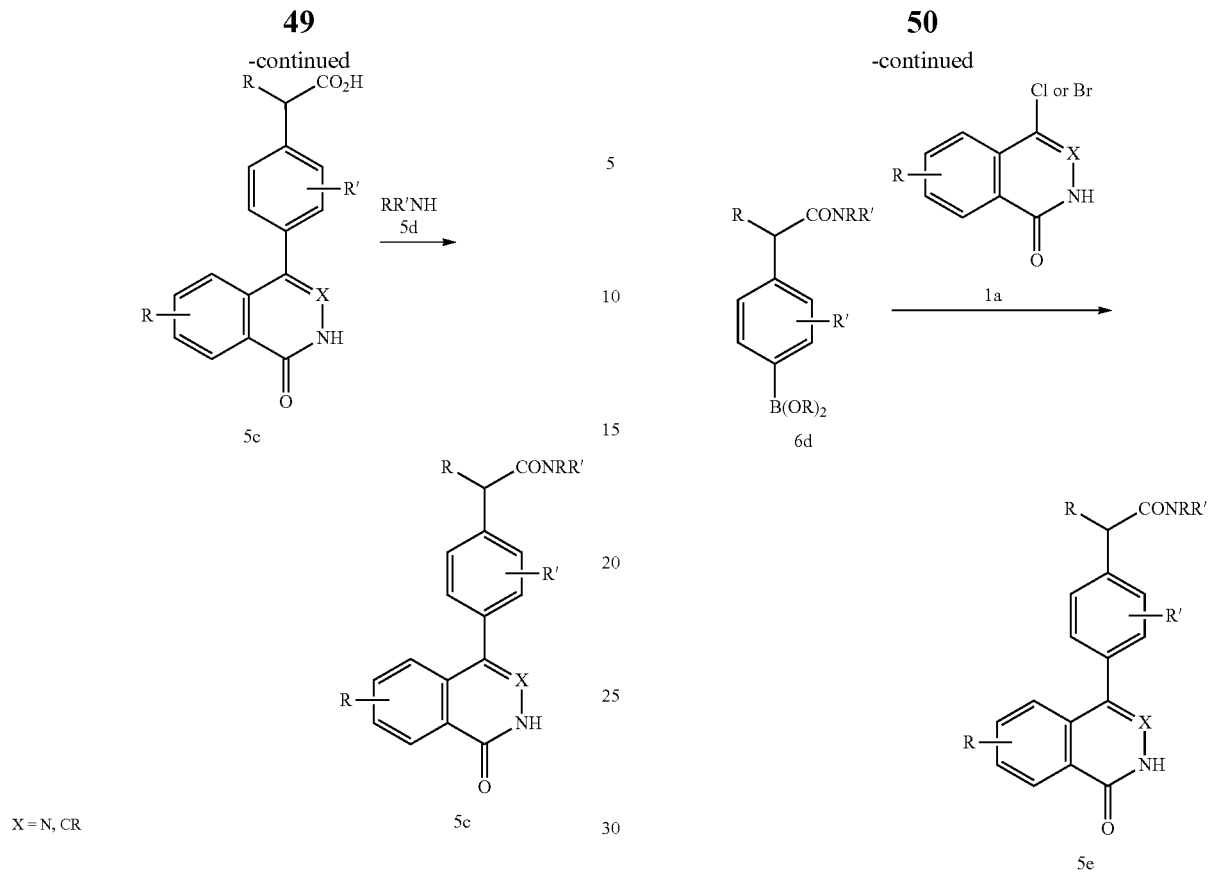

Scheme 5 shows the synthesis of amide target 5e, beginning with boronic acid/ester 5a, which is either commercially available or is prepared from the aryl halide precursor. Suzuki-Miyaura coupling between aryl halide 1a and boronic acid or boronate ester (5a) in the presence of a base such as $K_3PO_4$ and a catalyst such as $Pd(PPh_3)_4$ affords intermediate 5b. Cleavage of the protecting group (PG) by alkaline hydrolysis (or other reagents as appropriate) affords carboxylic acid 5c. Coupling of intermediate 5c with amine 5d in the presence of a coupling reagent, such as HATU or BOP, and a base such as DIEA affords target 5e.

Scheme 6 shows an alternate synthesis to target 5e beginning from acid 6a. Coupling of intermediate 6a with amine 6b in the presence of a coupling reagent, such as HATU or BOP, and a base such as DIEA affords intermediate amide 6c. Aryl halide 6c is converted to the aryl boronic acid or boronate ester 6d by coupling with bis(pinacolato)diboron in the presence of a base such a potassium acetate and a catalyst such as $PdCl_2(dppf)$ in dioxane or DMSO. Suzuki-Miyaura coupling between aryl halide 1a and boronic acid or boronate ester (6d) in the presence of a base such as $K_3PO_4$ and a catalyst such as $Pd(PPh_3)_4$ affords target compound 5e.

Scheme 6.

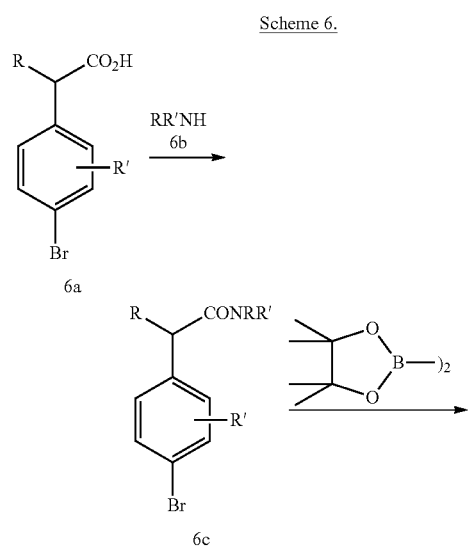

Scheme 7.

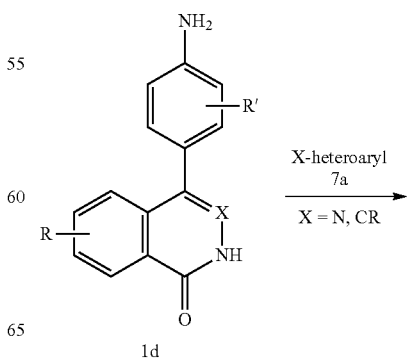

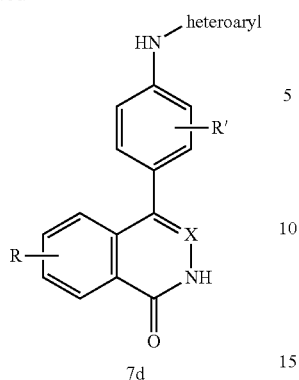

7d

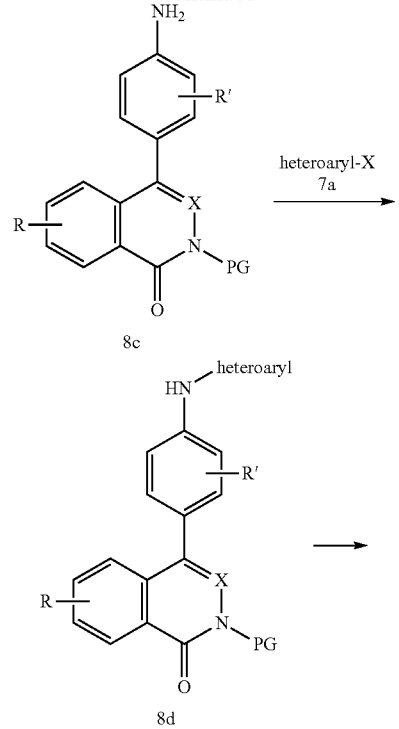

8c

8d

Scheme 7 shows the synthesis of target 7b beginning with intermediate aniline 1d. Aniline 1d is coupled with heteroaryl halide 7a under thermal $S_NAr$ conditions in the presence of a base such as DIEA in a solvent such as DMF to afford 7b. Alternatively, 1d and 7a may be coupled under Buchwald-Hartwig N-arylation conditions using a base such as $Cs_2CO_3$, a catalyst such as $Pd_2(dba)_3$ and an appropriate ligand to afford 7b.

Scheme 8.

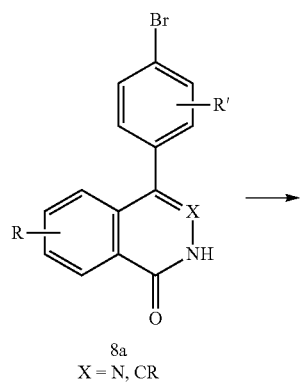

8a
X = N, CR

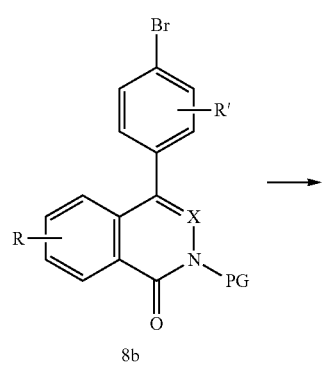

8b

7b

Scheme 8 shows an alternative synthesis of target 7b, beginning from intermediate 8a, which is either commercially available or can be prepared by literature methods. An appropriate protecting group is introduced by treatment with a base such as potassium carbonate and a protecting group reagent such as para-methoxybenzyl chloride to afford 8b. Treatment of aryl bromide 8b with sodium azide, $Cu_2O$ and a ligand such as proline affords aniline 8c. Aniline 8c is coupled with heteroaryl halide 7a under thermal $S_NAr$ conditions in the presence of a base such as DIEA in a solvent such as DMF to afford intermediate 8d. Alternatively, 8c and 7a may be coupled under Buchwald-Hartwig N-arylation conditions using a base such as $Cs_2CO_3$, a catalyst such as $Pd_2(dba)_3$ and an appropriate ligand to afford intermediate 8d. Cleavage of the protecting group under appropriate conditions (TFA in the case of a para-methoxybenzyl protecting group) affords target 7b.

Scheme 9.

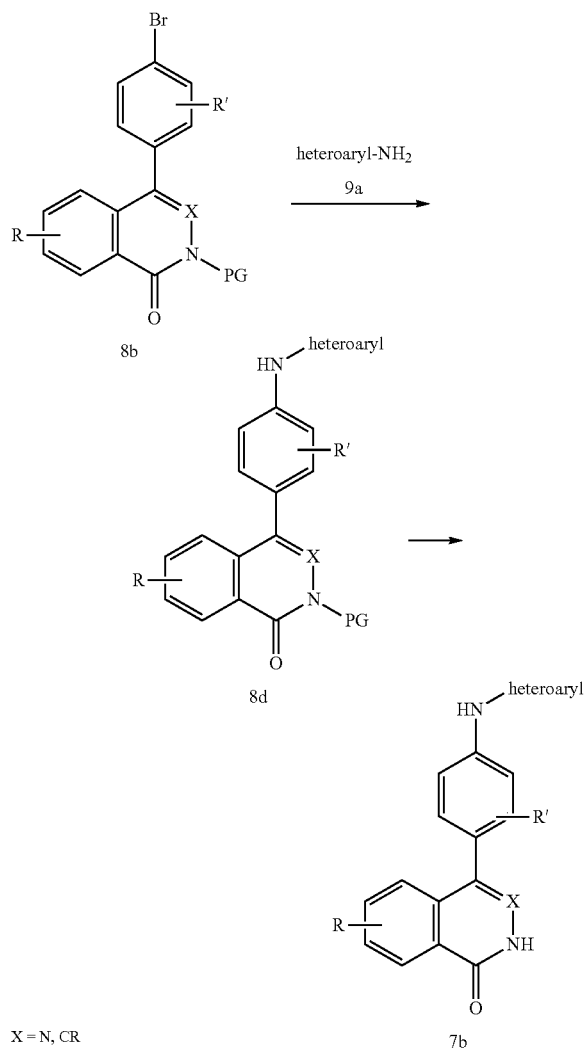

Scheme 9 shows an alternative synthesis of target 7b, starting from aryl bromide 8b. Coupling of intermediate 8b with heteroaryl amine 9a under Buchwald-Hartwig N-arylation conditions using a base such as Cs$_2$CO$_3$, a catalyst such as Pd$_2$(dba)$_3$ and an appropriate ligand affords intermediate 8d. Cleavage of the protecting group under appropriate conditions (TFA in the case of a para-methoxybenzyl protecting group) affords target 7b.

Scheme 10.

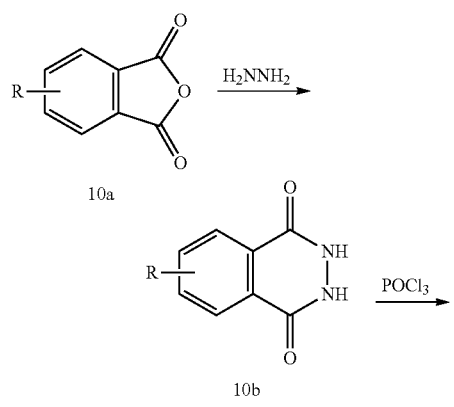

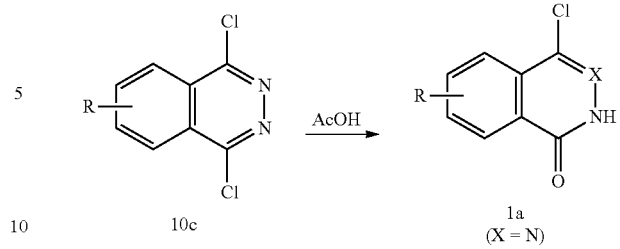

Scheme 10 shows the synthesis of intermediate 1a, where X=N. Furan-2,5-dione 10a can be converted to intermediate 10b by treatment with a reagent such as hydrazine. Intermediate 10b is chlorinated by treatment with a reagent such as POCl$_3$ to afford dichloro intermediate 10c. Partial hydrolysis of 10c with a reagent such as AcOH affords intermediate 1a.

Scheme 11.

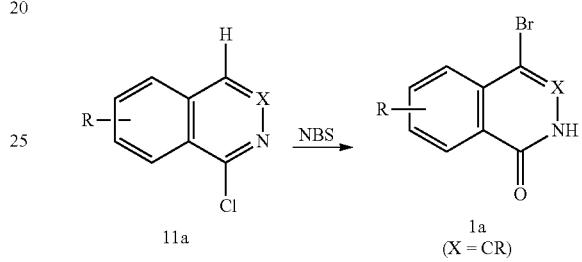

Scheme 11 shows the synthesis of intermediate 1a, where X=CR. Intermediate 11a is brominated with a reagent such as NBS to afford intermediate 1a.

Purification of intermediates and final products was carried out via either normal or reverse phase chromatography. Normal phase chromatography was carried out using prepacked SiO$_2$ cartridges eluting with either gradients of hexanes and EtOAc or DCM and MeOH unless otherwise indicated. Reverse phase preparative HPLC was carried out using C18 columns eluting with gradients of Solvent A (90% H$_2$O, 10% MeOH, 0.1% TFA) and Solvent B (10% H$_2$O, 90% MeOH, 0.1% TFA, UV 220 nm) or with gradients of Solvent A (90% H$_2$O, 10% ACN, 0.1% TFA) and Solvent B (10% H$_2$O, 90% ACN, 0.1% TFA, UV 220 nm) or with gradients of Solvent A (98% H$_2$O, 2% ACN, 0.05% TFA) and Solvent B (98% ACN, 2% H$_2$O, 0.05% TFA, UV 220 nm) (or) Sunfire Prep C18 OBD 5u 30×100 mm, 25 min gradient from 0-100% B. A=H$_2$O/ACN/TFA 90:10:0.1. B=ACN/H$_2$O/TFA 90:10:0.1 (or) Waters XBridge C18, 19×200 mm, 5-µm particles; Guard Column: Waters XBridge C18, 19×10 mm, 5-µm particles; Solvent A: water with 20-mM ammonium acetate; Solvent B: 95:5 acetonitrile:water with 20-mM ammonium acetate; Gradient: 25-65% B over 20 minutes, then a 5-minute hold at 100% B; Flow: 20 mL/min.

Unless otherwise stated, analysis of final products was carried out by reverse phase analytical HPLC.

Method A: Sunfire C18 column (3.5 µm C18, 3.0×150 mm) Gradient elution (1.0 mL/min) from 10-100% Solvent B over 10 min and then 100% Solvent B for 5 mM was used. Solvent A is (95% water, 5% acetonitrile, 0.05% TFA) and Solvent B is (5% water, 95% acetonitrile, 0.05% TFA, UV 254 nm).

Method B: XBridge Phenyl column (3.5 µm C18, 3.0×150 mm) Gradient elution (1.0 mL/min) from 10-100% Solvent B over 10 min and then 100% Solvent B for 5 mM was used. Solvent A is (95% water, 5% acetonitrile, 0.05% TFA) and Solvent B is (5% water, 95% acetonitrile, 0.05% TFA, UV 254 nm).

Method C: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient 0.5 min hold at 0% B, 0-100% B over 4 minutes, then a 0.5-minute hold at 100% B; Flow: 1 mL/min.

Method D: Waters BEH C18, 2.1×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

Method E: Waters BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes; Flow: 1.11 mL/min.

Method F: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes; Flow: 1.11 mL/min.

INTERMEDIATE 1

2-(4-(4-oxo-3,4-dihydrophthalazin-1-yl)phenyl)acetic acid

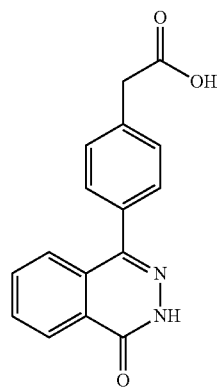 [SMILES: O=C(O)Cc1ccc(-c2n[nH]c(=O)c3ccccc23)cc1]

INTERMEDIATE 1A ethyl 2-(4-(4,4,5,5-tetramethyl-1,3,2-dioxaborolan-2-yl)phenyl)acetate

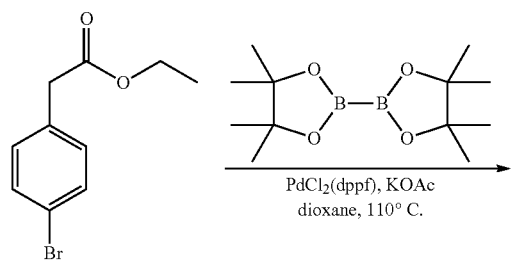

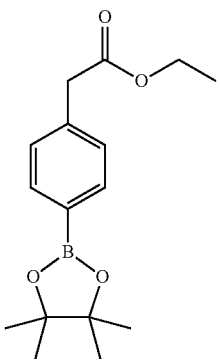

To a vial containing a degassed (3× vacuum/Ar) mixture of ethyl 2-(4-bromophenyl)acetate (1 g, 4.11 mmol), bis(pinacolato)diboron (1.25 g, 4.94 mmol), and potassium acetate (1.21 g, 12.3 mmol) in dioxane (10 mL), was added $PdCl_2$(dppf) $CH_2Cl_2$ adduct (0.090 g, 0.123 mmol). The reaction mixture was degassed, sealed and heated at 110° C. for 16 h. The mixture was diluted with water, then extracted with EtOAc. The organic phase was concentrated and purified via flash chromatography (EtOAc/hexane) to afford 1.1 g (92%) of Intermediate 1A.

MS (ESI) m/z: 291.2 $(M+H)^+$; $^1$H NMR (500 MHz, $CDCl_3$) δ 7.84-7.71 (m, 2H), 7.34-7.28 (m, J=8.0 Hz, 2H), 4.15 (q, J=7.0 Hz, 2H), 3.63 (s, 2H), 1.27 (s, 12H), 1.26-1.22 (m, 3H).

INTERMEDIATE 1B ethyl 2-(4-(4-oxo-3,4-dihydrophthalazin-1-yl)phenyl)acetate

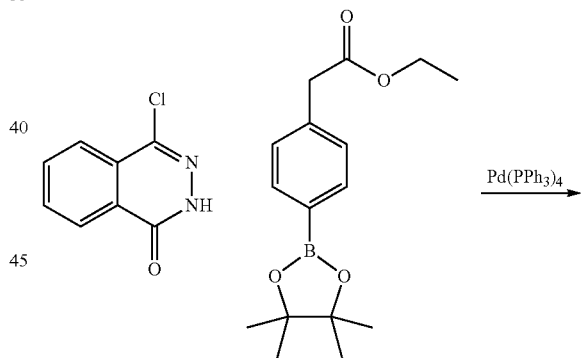

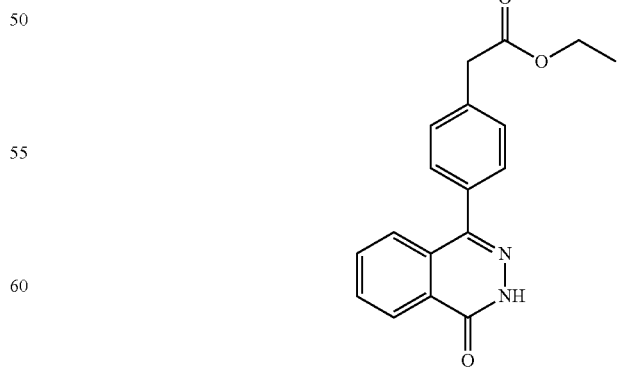

To 4-chlorophthalazin-1(2H)-one (200 mg, 1.11 mmol), Intermediate 1A (386 mg, 1.33 mmol) and $K_3PO_4$ (588 mg, 2.77 mmol), were added dioxane (9 mL) and water (1 mL). The mixture was degassed (evacuated and flushed with Ar (5×)). Pd(PPh₃)₄ (64.0 mg, 0.055 mmol) was added, then the mixture was degassed (2×). The reaction vial was sealed and heated in a microwave reactor at 150° C. for 30 min. The reaction mixture was concentrated and purified via flash chromatography (EtOAc/hexane) to afford 218 mg (46%) of Intermediate 1B.

MS (ESI) m/z: 309.1 (M+H)$^+$; $^1$H NMR (500 MHz, DMSO-d₆) δ 12.84 (s, 1H), 8.46-8.28 (m, 1H), 7.99-7.82 (m, 2H), 7.69 (d, J=7.2 Hz, 1H), 7.59-7.54 (m, 2H), 7.45 (d, J=6.6 Hz, 2H), 4.12 (qd, J=7.1, 1.8 Hz, 2H), 3.79 (s, 2H), 1.22 (td, J=7.0, 1.9 Hz, 3H).

INTERMEDIATE 1

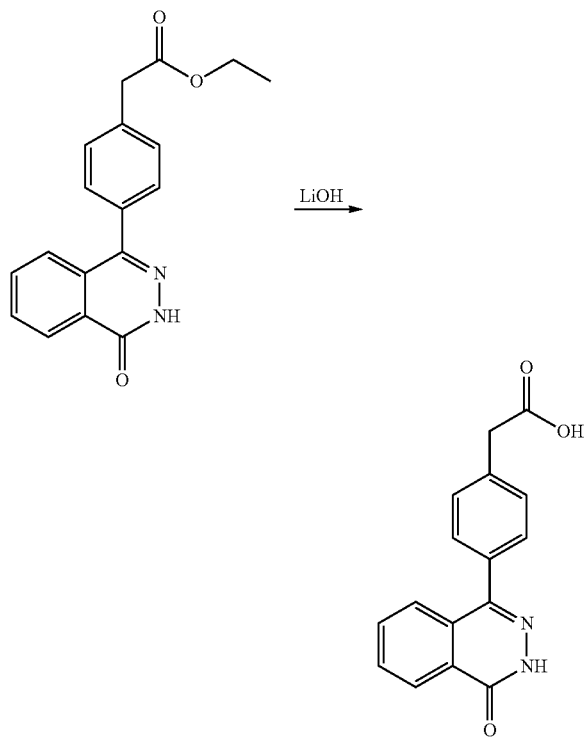

To a solution of Intermediate 1B (210 mg, 0.681 mmol) in MeOH (5 mL) and THF (5 mL), was added 1M aq. lithium hydroxide (3.41 mL, 3.41 mmol). The mixture was stirred rt overnight, then was concentrated. The residue was acidified with TFA, then was dissolved in DMSO/MeOH, and purified preparative HPLC to afford 170 mg (89%) of Intermediate 1.

MS (ESI) m/z: 281.0 (M+H)$^+$; $^1$H NMR (500 MHz, DMSO-d₆) δ 12.83 (s, 1H), 8.42-8.21 (m, 1H), 7.99-7.82 (m, 2H), 7.77-7.62 (m, 1H), 7.59-7.50 (m, 2H), 7.49-7.37 (m, J=8.3 Hz, 2H), 3.69 (s, 2H).

INTERMEDIATE 2

5-((4-methylpiperazin-1-yl)methyl)isoindoline, 3 TFA

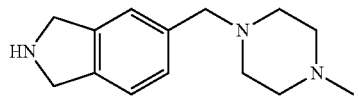 [SMILES: CN1CCN(Cc2ccc3c(c2)CNC3)CC1]

INTERMEDIATE 2A tert-butyl di(prop-2-yn-1-yl)carbamate

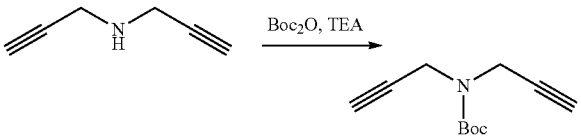

To a solution of 2-Propyn-1-amine and N-2-propynyl- (1.110 mL, 10.74 mmol) in THF (20 mL) at rt, was added BOC₂O (2.58 g, 11.81 mmol). To this mixture was added TEA (0.150 mL, 1.074 mmol). The mixture was stirred at rt for 14 h. The reaction mixture was concentrated to an oil. The oil was partitioned between 0.2 N HCl and EtOAc. The organic phase was washed with H₂O, sat. NaHCO₃ and brine, dried (Na₂SO₄), filtered through a 1" pad of SiO₂ and concentrated to afford 2.40 g (100%) of Intermediate 2A as a yellow oil.

MS (ESI) m/z: 216.1 (M+H)$^+$; $^1$H NMR (400 MHz, CDCl₃) δ 4.17 (br. s., 4H), 2.22 (t, J=2.4 Hz, 2H), 1.48 (s, 9H).

INTERMEDIATE 2B tert-butyl 5-(hydroxymethyl)isoindoline-2-carboxylate

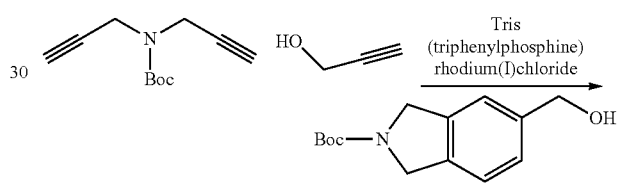

To a degassed (evacuated and flushed with Ar (5×)) solution of prop-2-yn-1-ol (0.961 mL, 16.11 mmol) in toluene (5 mL) at 50° C., were added in 5 portions at 10 minute intervals Intermediate 2A (1.20 g, 5.37 mmol) in degassed toluene (5 mL) and Tris(triphenylphosphine)rhodium(I) chloride (0.124 g, 0.134 mmol). Following the last addition, the brown mixture was stirred at 50° C. for 1.25 h. The reaction mixture was concentrated, then was co-evaporated with CHCl₃ (2×). The crude product was purified by flash chromatography (0 to 100% ethyl acetate/hexanes, eluted at 75% EtOAc) to afford 1.15 g (86% yield) of Intermediate 2B as a white solid.

MS (ESI) m/z: 521.3 (M+H)$^+$; $^1$H NMR (400 MHz, CD₃OD) δ 7.33-7.21 (m, 3H), 4.63 (dd, J=5.6, 3.2 Hz, 4H), 4.60 (s, 2H), 1.52 (s, 9H).

INTERMEDIATE 2C tert-butyl 5-(((methylsulfonyl)oxy)methyl)isoindoline-2-carboxylate

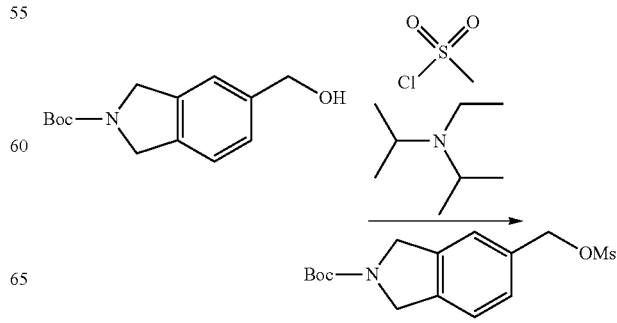

To a solution of Intermediate 2B (500 mg, 2.006 mmol) in DCM (10 mL) at 0° C., were added DIEA (0.420 mL, 2.407 mmol) and Ms-Cl (0.172 mL, 2.206 mmol). The mixture was stirred at 0° C. for 1.5 h. The mixture was diluted with DCM, then was washed with half sat. NH4Cl and brine. The organic phase was dried (Na2SO4) and concentrated to afford 655 mg (100%) of Intermediate 2C as a brown oil. The material was used in the following step without further purification.

MS (ESI) m/z: 272.0 (M−t-Bu+2H)+

INTERMEDIATE 2D tert-butyl 5-((4-methylpiperazin-1-yl)methyl)isoindoline-2-carboxylate

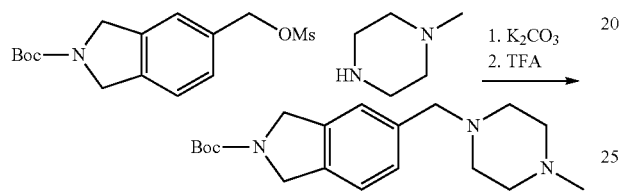

To a solution of Intermediate 2C (657 mg, 2.007 mmol) in acetone (10 mL) at rt, were added K2CO3 (416 mg, 3.01 mmol) and 1-methyl piperazine (0.556 mL, 5.02 mmol). The mixture was stirred at rt for 2.5 h, then 1 h at 50° C. The mixture was concentrated, then was partitioned between EtOAc and H2O. The aqueous phase was extracted with EtOAc (2×). The combined organic phase was dried (Na2SO4) and concentrated to afford Intermediate 2D as a brown oil.

MS (ESI) m/z: 332.2 (M+H)+; 1H NMR (400 MHz, CD3OD) δ 7.30-7.21 (m, 3H), 4.63 (dd, J=5.5, 2.0 Hz, 4H), 3.53 (s, 2H), 2.50 (br. s., 8H), 2.27 (s, 3H), 1.52 (s, 9H)

INTERMEDIATE 2

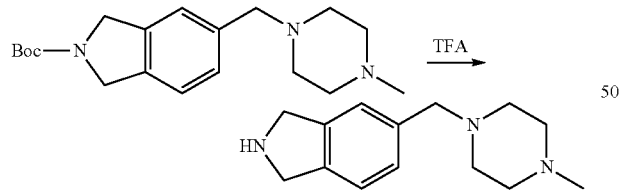

Intermediate 2D was treated with 4N HCl in dioxane (5 mL, 20.00 mmol) and the resultant suspension was stirred for 1 h, then was concentrated. The mixture was redissolved in TFA (10 mL) and was stirred at rt for 20 min. The mixture was concentrated. The brown oil was coevaporated with DCM (2×), ether, MeOH and CH3CN to afford 1.36 g (100% yield, ~85% purity) of Intermediate 2 as a brown semisolid, which was used as is without further purification.

MS (ESI) m/z: 232.2 (M+H)+; 1H NMR (400 MHz, CD3OD) δ 7.49-7.40 (m, 3H), 4.62 (s, 4H), 3.82 (s, 2H), 3.34 (br. s., 4H), 2.89 (s, 3H), 2.90 (br. s, 4H)

INTERMEDIATE 3

4-(4-aminophenyl)phthalazin-1(2H)-one, TFA salt

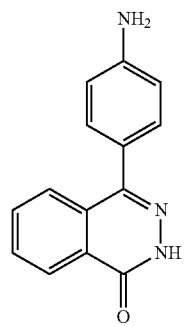 [SMILES: Nc1ccc(-c2n[nH]c(=O)c3ccccc23)cc1]

INTERMEDIATE 3A tert-butyl (4-(4-oxo-3,4-dihydrophthalazin-1-yl)phenyl)carbamate

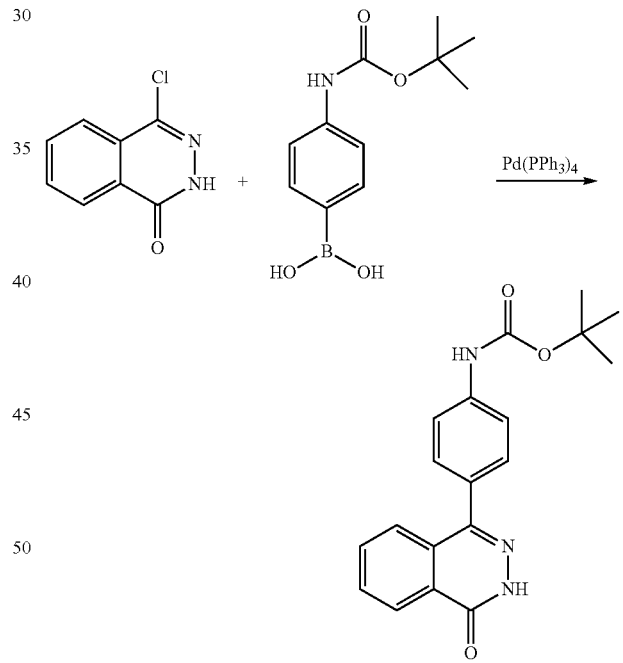

To 4-chlorophthalazin-1(2H)-one (118 mg, 0.653 mmol), (4-((tert-butoxycarbonyl)amino)phenyl)boronic acid (170 mg, 0.719 mmol) and potassium phosphate (347 mg, 1.634 mmol), were added dioxane (9 mL) and water (1 mL). The mixture was degassed (evacuated and flushed with Ar (5×)). Pd(PPh3)4 (37.8 mg, 0.033 mmol) was added, then the mixture was degassed (2×). The reaction vial was sealed and heated in a microwave reactor at 150° C. for 35 min. The reaction mixture was concentrated and purified via flash chromatography to afford 150 mg (68%) of Intermediate 3A.

MS (ESI) m/z: 338.1 (M+H)+.

INTERMEDIATE 3

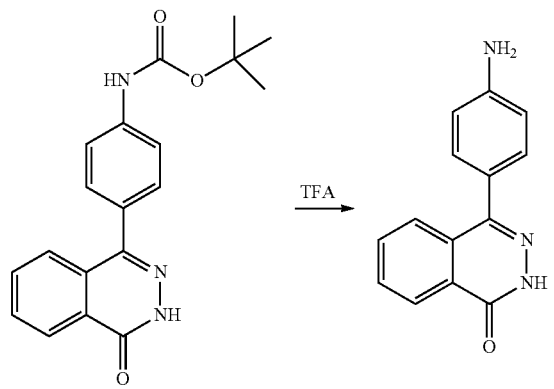 [SMILES: CC(C)(C)OC(=O)Nc1ccc(-c2n[nH]c(=O)c3ccccc23)cc1 ; Nc1ccc(-c2n[nH]c(=O)c3ccccc23)cc1]

To Intermediate 3A (150 mg, 0.445 mmol) in CH$_2$Cl$_2$ (3 mL), was added TFA (2 mL). The mixture was stirred rt for 2 h, then was concentrated. The crude product was purified via flash chromatography, then preparative HPLC to afford 62 mg (59%) of Intermediate 3.

MS (ESI) m/z: 238.1 (M+H)$^+$; $^1$H NMR (500 MHz, CD$_3$OD) δ 8.44 (dt, J=4.7, 2.3 Hz, 1H), 7.97-7.87 (m, 2H), 7.81-7.75 (m, 1H), 7.71-7.61 (m, 2H), 7.41-7.30 (m, 2H)

INTERMEDIATE 4

2-(2-fluoro-4-(4,4,5,5-tetramethyl-1,3,2-dioxaborolan-2-yl)phenyl)-1-(isoindolin-2-yl)ethanone

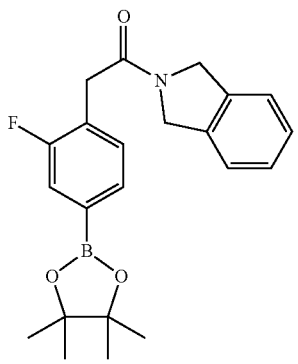 [SMILES: CC1(C)OB(c2ccc(CC(=O)N3Cc4ccccc4C3)c(F)c2)OC1(C)C]

INTERMEDIATE 4A 2-(4-bromo-2-fluorophenyl)-1-(isoindolin-2-yl)ethanone

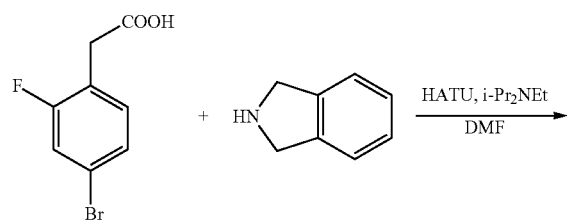

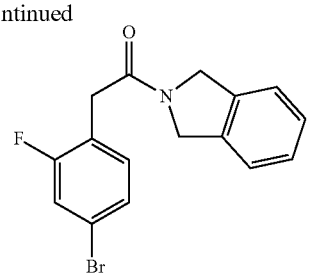

To 2-(4-bromo-2-fluorophenyl)acetic acid (300 mg, 1.287 mmol), isoindoline (0.161 mL, 1.416 mmol), and HATU (587 mg, 1.545 mmol) in DMF (5 mL), was added DIEA (0.450 mL, 2.57 mmol). The mixture was stirred at rt for 1 h. The resultant heterogeneous mixture was diluted with EtOAc, then was washed with H$_2$O, 1N HCl, H$_2$O, sat. NaHCO$_3$ and brine. The organic phase was dried (Na$_2$SO$_4$), filtered and concentrated. The crude product was purified by flash chromatography (gradient from 0 to 100% ethyl acetate/hexanes) to afford 147 mg (34%) of Intermediate 4A as a white solid.

MS (ESI) m/z: 333.9 (M+H)$^+$; $^1$H NMR (400 MHz, CDCl$_3$) δ 7.34-7.30 (m, 3H), 7.30-7.22 (m, 4H), 4.89 (s, 2H), 4.83 (s, 2H), 3.73 (s, 2H)

INTERMEDIATE 4

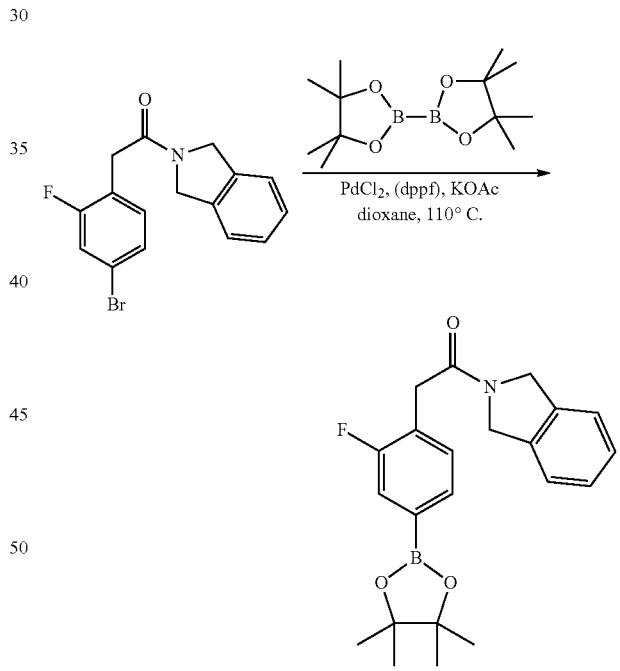

To a mixture of Intermediate 4A (146 mg, 0.437 mmol), bis(pinacolato)diboron (133 mg, 0.524 mmol), and potassium acetate (129 mg, 1.31 mmol) in a reaction vial, was added dioxane (3 mL). The mixture was degassed (evacuated and flushed with Ar (3×)). PdCl$_2$(dppf) CH$_2$Cl$_2$ adduct (9.6 mg, 0.013 mmol) was added, then reaction mixture was degassed (3× vacuum/Ar). The vial was sealed, then was heated at 110° C. for 2 h. The reaction mixture was diluted with EtOAc, then was washed with H$_2$O and brine. The organic phase was dried (Na$_2$SO$_4$) and concentrated. The crude product was purified by flash chromatography (gradient from 0 to 50% ethyl acetate/hexanes) to afford 120 mg (72%) of Intermediate 4 as a yellow solid.

MS (ESI) m/z: 386.1 (M+H)$^+$; $^1$H NMR (400 MHz, CDCl$_3$) δ 7.55 (dd, J=7.5, 0.9 Hz, 1H), 7.50 (d, J=10.1 Hz, 1H), 7.39 (t, J=7.4 Hz, 1H), 7.32-7.22 (m, 4H), 4.84 (s, 4H), 3.80 (s, 2H), 1.33 (s, 12H)

INTERMEDIATE 5

2-(3-fluoro-4-(4,4,5,5-tetramethyl-1,3,2-dioxaborolan-2-yl)phenyl)-1-(isoindolin-2-yl)ethanone

INTERMEDIATE 5A 2-(4-bromo-3-fluorophenyl)-1-(isoindolin-2-yl)ethanone

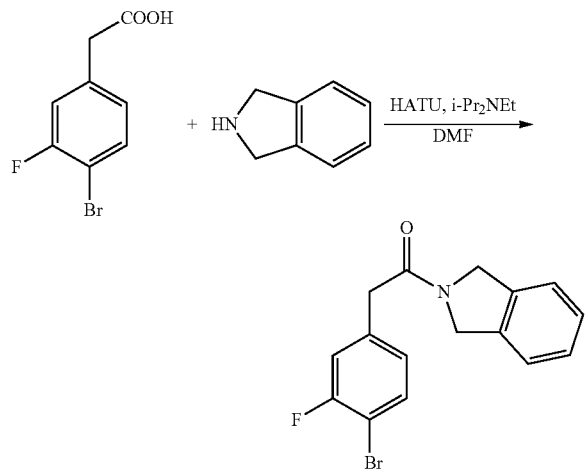

To a mixture of 2-(4-bromo-3-fluorophenyl)acetic acid (300 mg, 1.287 mmol), isoindoline (0.161 mL, 1.416 mmol), and HATU (734 mg, 1.931 mmol) in DMF (5 mL), was add DIEA (0.450 mL, 2.6 mmol). The mixture was stirred rt for 18 h. The reaction mixture was diluted with EtOAc, then was washed with H$_2$O, 1N HCl, H$_2$O, sat. Na$_2$CO$_3$ and brine. The organic phase was dried (Na$_2$SO$_4$), filtered through a 1" pad of SiO$_2$ and concentrated. The crude product was purified by flash chromatography (gradient from 0 to 100% ethyl acetate/hexanes) to afford 379 mg (88%) of Intermediate 5A as an off-white solid. MS (ESI) m/z: 333.9 (M+H)$^+$; $^1$H NMR (400 MHz, CDCl$_3$) δ 7.50 (dd, J=8.0, 7.4 Hz, 1H), 7.33-7.22 (m, 4H), 7.14 (dd, J=9.2, 2.0 Hz, 1H), 7.01 (dd, J=8.5, 1.9 Hz, 1H), 4.83 (s, 4H), 3.72 (s, 2H)

INTERMEDIATE 5

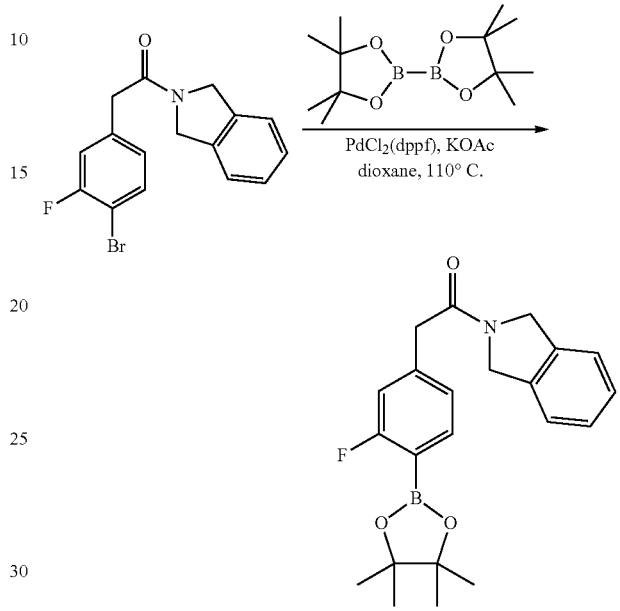

To a mixture of Intermediate 5A (200 mg, 0.598 mmol), bis(pinacolato)diboron (182 mg, 0.718 mmol), and potassium acetate (176 mg, 1.80 mmol) in a reaction vial, was added dioxane (5 mL). The mixture was degassed (evacuated and flushed with Ar (3×)). PdCl$_2$(dppf) CH$_2$Cl$_2$ adduct (13 mg, 0.018 mmol) was added, then the reaction mixture was degassed (3× vacuum/Ar). The vial was sealed, then was heated at 110° C. for 2 h. Additional catalyst (13 mg) was added and the reaction mixture was stirred at 110° C. for 2 more hours. The reaction mixture was cooled to room temperature, then was filtered and concentrated. The crude product was purified by flash chromatography (gradient from 0 to 100% ethyl acetate/hexanes) to afford 208 mg (91%) of Intermediate 5 as a yellow solid.

MS (ESI) m/z: 386.1 (M+H)$^+$; $^1$H NMR (400 MHz, CDCl$_3$) δ 7.71 (t, J=6.9 Hz, 1H), 7.35-7.20 (m, 4H), 7.13 (d, J=7.5 Hz, 1H), 7.04 (d, J=10.1 Hz, 1H), 4.83 (s, 2H), 4.77 (s, 2H), 3.78 (s, 2H), 1.35 (s, 12H).

INTERMEDIATE 6

4-bromoisoquinolin-1(2H)-one

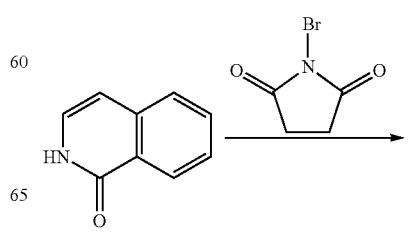

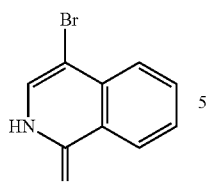

To a solution of isoquinolin-1(2H)-one (105 mg, 0.723 mmol) in DMF (2 mL), was added NBS (142 mg, 0.796 mmol). The mixture was stirred at rt for 2 h, then was concentrated. The crude product was purified via preparative HPLC to afford 110 mg (68%) of Intermediate 6.

MS (ESI) m/z: 223.9 (M+H)$^+$; $^1$H NMR (500 MHz, DMSO-d$_6$) δ 11.57 (br. s., 1H), 8.24 (dd, J=8.0, 0.8 Hz, 1H), 7.88-7.83 (m, 1H), 7.79-7.75 (m, 1H), 7.61 (ddd, J=8.0, 7.1, 1.1 Hz, 1H), 7.55 (s, 1H).

INTERMEDIATE 7

2-(4-bromophenyl)-1-(isoindolin-2-yl)ethanone

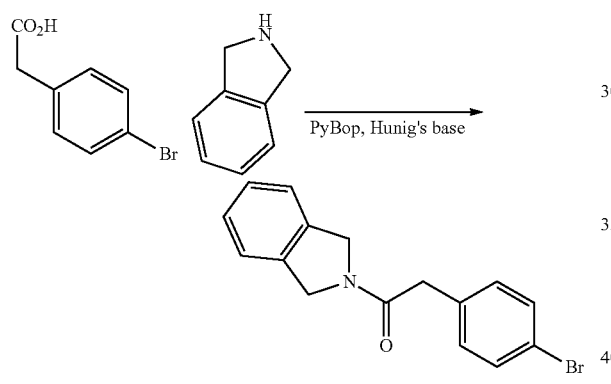

To a mixture of 2-(4-bromophenyl)acetic acid (300 mg, 1.395 mmol), isoindoline (183 mg, 1.535 mmol), and HATU (796 mg, 2.093 mmol) in DMF (5 mL), was add DIEA (0.487 mL, 2.79 mmol). The mixture was stirred at rt overnight. The reaction mixture was quenched with water, then extracted with EtOAc. The organic phase was washed with 10% LiCl, brine, and concentrated. The residue was purified via flash chromatography (EtOAc/hexane) to afford 390 mg (88%) of Intermediate 7.

MS (ESI) m/z: 316.0 (M+H)$^+$.

INTERMEDIATE 8

(4-(2-(isoindolin-2-yl)acetyl)phenyl)boronic acid

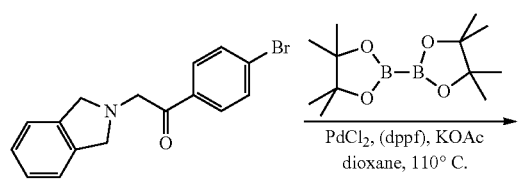

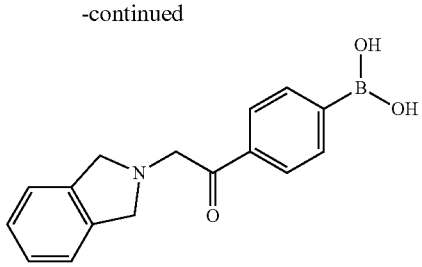

A mixture of Intermediate 7 (30 mg, 0.095 mmol), bis(pinacolato)diboron (24 mg, 0.095 mmol), and potassium acetate (27.9 mg, 0.285 mmol) in dioxane (1 mL) was degassed (3× vacuum/Ar). Then PdCl$_2$(dppf) CH$_2$Cl$_2$ adduct (2.083 mg, 2.85 µmol) was added, the reaction mixture was degassed again (3× vacuum/Ar), sealed in a vial and heated at 110° C. for 2 h. The reaction was purified via preparative HPLC to afford 14 mg (53%) of Intermediate 8.

MS (ESI) m/z: 282.1 (M+H)$^+$.

INTERMEDIATE 9

1-(isoindolin-2-yl)-2-(4-(4,4,5,5-tetramethyl-1,3,2-dioxaborolan-2-yl)phenyl)ethanone

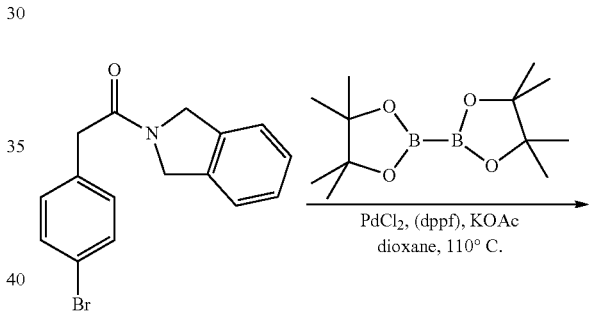

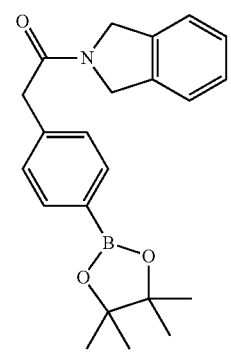

According to a procedure similar to the preparation of Intermediate 8, Intermediate 7 (400 mg, 1.27 mmol) afforded after flash chromatography (0 to 60% EtOAc/hexane gradient) 406 mg (88%) of Intermediate 9.

MS (ESI) m/z: 364.1 (M+H)$^+$; $^1$H NMR (500 MHz, CDCl$_3$) δ 7.82-7.77 (m, J=8.3 Hz, 2H), 7.39-7.33 (m, J=8.0 Hz, 2H), 7.27 (d, J=0.6 Hz, 3H), 7.27-7.24 (m, 1H), 7.20 (d, J=6.6 Hz, 1H), 4.84 (s, 2H), 4.77 (s, 2H), 3.81 (s, 2H), 1.38-1.31 (m, 12H).

INTERMEDIATE 10

N-(4-(4,4,5,5-tetramethyl-1,3,2-dioxaborolan-2-yl)phenyl)indoline-1-carboxamide

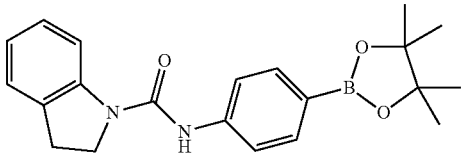 [SMILES: CC1(C)OB(c2ccc(NC(=O)N3CCc4ccccc43)cc2)OC1(C)C]

INTERMEDIATE 10A

N-(4-bromophenyl)indoline-1-carboxamide

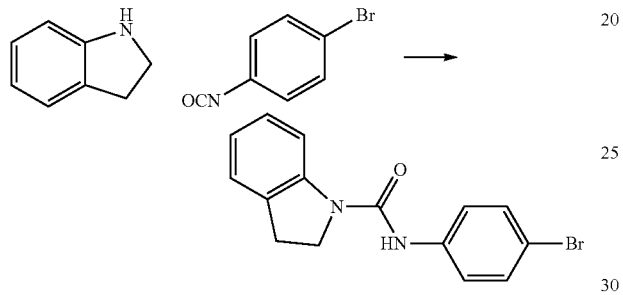

A mixture of 1-bromo-4-isocyanatobenzene (300 mg, 1.515 mmol) and indoline (199 mg, 1.667 mmol) in CH$_2$Cl$_2$ (5 mL) was stirred at rt 1 h. The reaction mixture was diluted with EtOAc (100 mL), then was washed with 1N HCl, sat. Na$_2$CO$_3$, and brine. The organic phase was dried over Na$_2$SO$_4$, then concentrated. The residue was purified by flash chromatography (0-60% EtOAc/hexane gradient) to afford 470 mg (98%) of Intermediate 10A as a yellow foam.

MS (ESI) m/z: 317.0 (M+H)$^+$; $^1$H NMR (500 MHz, CDCl$_3$) δ 7.88 (d, J=8.0 Hz, 1H), 7.49-7.42 (m, 2H), 7.41-7.35 (m, 2H), 7.22-7.17 (m, 2H), 6.99 (td, J=7.4, 1.1 Hz, 1H), 6.47 (br. s., 1H), 4.15-4.05 (m, 2H), 3.25 (t, J=8.5 Hz, 2H)

INTERMEDIATE 10

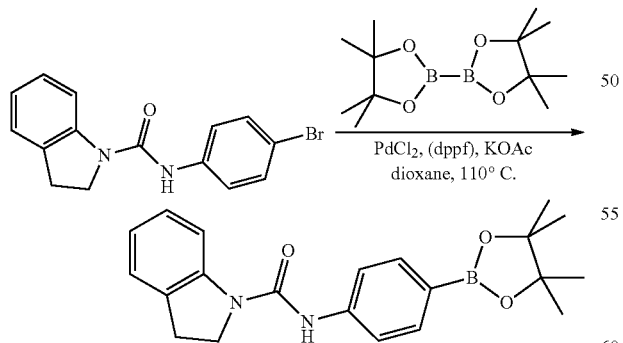

To a mixture of Intermediate 10A (470 mg, 1.482 mmol), bis(pinacolato)diboron (452 mg, 1.778 mmol), and potassium acetate (436 mg, 4.45 mmol) in dioxane (20 mL), was added PdCl$_2$(dppf) CH$_2$Cl$_2$ adduct (32.5 mg, 0.044 mmol). The reaction mixture was degassed (3× vacuum/Ar), sealed in a vial and heated at 110° C. for 3 h. The reaction was quenched with water, extracted with EtOAc (2×30 mL). The combined organic layer was washed with brine, dried (Na$_2$SO$_4$) and concentrated. The residue was purified by flash chromatography (0-60% EtOAc/hexane gradient) to afford 430 mg (80%) of Intermediate 10 as a white solid.

MS (ESI) m/z: 365.1 (M+H)$^+$; $^1$H NMR (500 MHz, CDCl$_3$) δ 7.89 (d, J=8.0 Hz, 1H), 7.81-7.77 (m, J=8.3 Hz, 2H), 7.52-7.48 (m, 2H), 7.23-7.18 (m, 2H), 7.01-6.94 (m, 1H), 6.56 (s, 1H), 4.17-4.04 (m, 2H), 3.25 (t, J=8.5 Hz, 2H), 1.39-1.32 (m, 12H).

INTERMEDIATE 11

2-(4-(4-oxo-3,4-dihydrophthalazin-1-yl)phenyl)propanoic acid

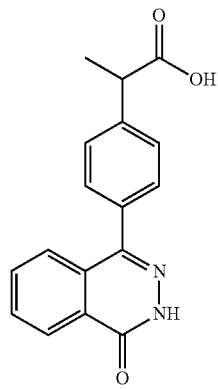 [SMILES: CC(C(=O)O)c1ccc(-c2n[nH]c(=O)c3ccccc23)cc1]

INTERMEDIATE 11A ethyl 2-(4-bromophenyl)propanoate

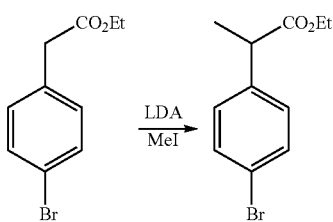

To a solution of ethyl 2-(4-bromophenyl)acetate (150 mg, 0.617 mmol) in THF (3 mL) at −78° C., was added 1.5M LDA (0.514 mL, 0.926 mmol). The mixture was stirred at −78° C. for 20 min, then iodomethane (175 mg, 1.23 mmol) was added. The solution was allowed to warm to rt and stirred overnight. The reaction mixture was concentrated and the residue was purified by flash chromatography (0-20% EtOAc/hexane gradient) to afford 120 mg (76%) of Intermediate 11A as a yellow oil.

MS (ESI) m/z: 257.0 (M+H)$^+$; $^1$H NMR (500 MHz, CDCl$_3$) δ 7.47-7.42 (m, 2H), 7.21-7.16 (m, 2H), 4.12 (dddd, J=17.6, 10.4, 7.1, 3.7 Hz, 2H), 3.67 (q, J=7.3 Hz, 1H), 1.48 (d, J=7.2 Hz, 3H), 1.21 (t, J=7.2 Hz, 3H)

INTERMEDIATE 11B ethyl 2-(4-(4,4,5,5-tetramethyl-1,3,2-dioxaborolan-2-yl)phenyl)propanoate

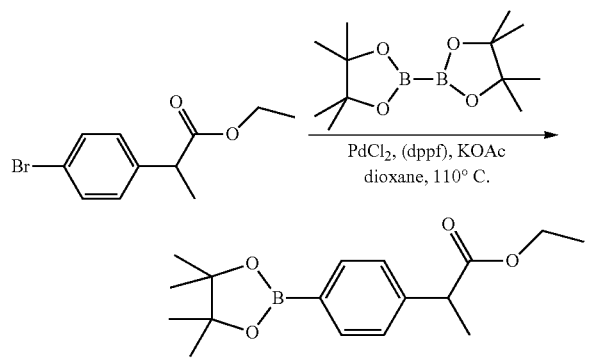

To a mixture of Intermediate 11A (120 mg, 0.467 mmol), bis(pinacolato)diboron (142 mg, 0.56 mmol), and potassium acetate (137 mg, 1.40 mmol) in dioxane (4 mL), was added PdCl$_2$(dppf) CH$_2$Cl$_2$ adduct (10 mg, 0.014 mmol). The reaction mixture was degassed (3× vacuum/Ar), sealed and heated at 110° C. for 16 h. The reaction mixture was concentrated and the residue was purified by flash chromatography (0-30% EtOAc/hexane gradient) to afford 120 mg (85%) of Intermediate 11B as a yellow oil.

MS (ESI) m/z: 327.2 (M+H)$^+$; $^1$H NMR (500 MHz, CDCl$_3$) δ 7.81-7.75 (m, J=8.3 Hz, 2H), 7.35-7.29 (m, J=8.0 Hz, 2H), 4.11 (dddd, J=17.8, 10.6, 7.1, 3.6 Hz, 2H), 3.77-3.66 (m, 1H), 1.49 (d, J=7.2 Hz, 3H), 1.37-1.30 (m, 12H), 1.19 (t, J=7.2 Hz, 3H)

INTERMEDIATE 11C ethyl 2-(4-(4-oxo-3,4-dihydrophthalazin-1-yl)phenyl)propanoate

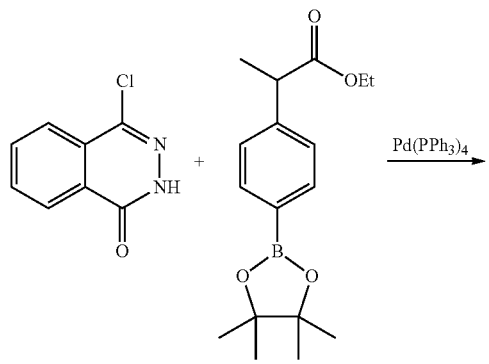

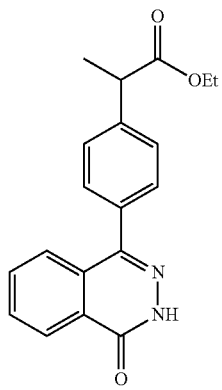

To 4-chlorophthalazin-1(2H)-one (70 mg, 0.388 mmol), Intermediate 11B (118 mg, 0.388 mmol) and potassium phosphate (206 mg, 0.969 mmol), were added dioxane (3 mL) and water (0.333 mL). The mixture was degassed (evacuated and flushed with Ar (5×)). Pd(PPh$_3$)$_4$ (22.40 mg, 0.019 mmol) was added, then the mixture was degassed (2×). The reaction vial was sealed and heated in a microwave reactor at 150° C. for 30 min. The reaction mixture was concentrated and the residue was purified by flash chromatography (0-80% EtOAc/hexane gradient) to afford 100 mg (80%) of Intermediate 11C as a yellow foam.

MS (ESI) m/z: 323.1 (M+H)$^+$; $^1$H NMR (500 MHz, DMSO-d$_6$) δ 12.84 (s, 1H), 8.41-8.31 (m, 1H), 7.98-7.84 (m, 2H), 7.70 (d, J=7.7 Hz, 1H), 7.57 (d, J=8.3 Hz, 2H), 7.47 (d, J=8.0 Hz, 2H), 4.20-4.02 (m, 2H), 3.91 (d, J=6.9 Hz, 1H), 1.46 (d, J=7.2 Hz, 3H), 1.17 (t, J=7.0 Hz, 3H).

Intermediate 11

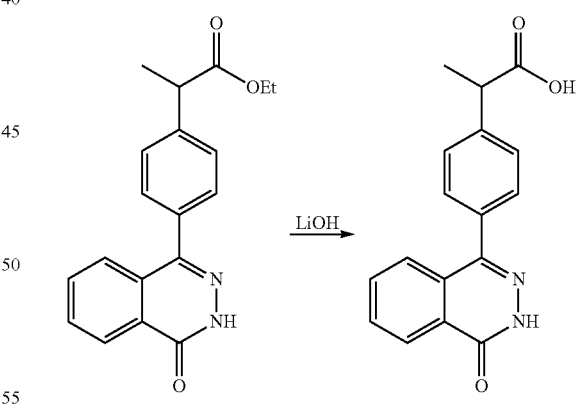

To a solution of Intermediate 11C (100 mg, 0.310 mmol) in THF (3 mL), was added 1M LiOH (0.620 mL, 0.620 mmol). The mixture was stirred at rt for 3 h, then was concentrated. The residue was purified via preparative HPLC to afford 90 mg (99%) of Intermediate 11 as a white solid.

MS (ESI) m/z: 295.1 (M+H)$^+$; $^1$H NMR (500 MHz, DMSO-d$_6$) δ 12.83 (s, 1H), 8.42-8.23 (m, 1H), 7.99-7.82 (m, 2H), 7.78-7.66 (m, 1H), 7.61-7.52 (m, J=8.0 Hz, 2H), 7.50-7.40 (m, J=8.0 Hz, 2H), 3.80 (q, J=7.2 Hz, 1H), 1.44 (d, J=6.9 Hz, 3H).

EXAMPLE 1

4-(4-(2-(isoindolin-2-yl)-2-oxoethyl)phenyl)phthalazin-1(2H)-one

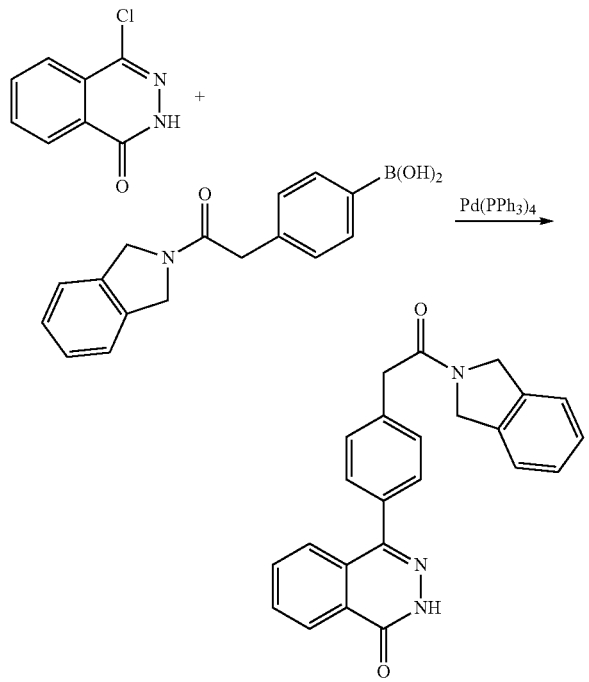

To 4-chlorophthalazin-1(2H)-one (9.9 mg, 0.055 mmol), Intermediate 8 (14 mg, 0.050 mmol) and potassium phosphate (26.4 mg, 0.125 mmol), were added dioxane (3 mL) and water (0.5 mL). The mixture was degassed (evacuated and flushed with Ar (5×)). Pd(PPh$_3$)$_4$ (2.9 mg, 2.5 μmol) was added, then the mixture was degassed (2×). The reaction vial was sealed and heated in a microwave reactor at 150° C. for 25 min. The reaction mixture was concentrated, then was purified by preparative HPLC to afford 4.4 mg (18%) of Example 1.

MS (ESI) m/z: 382.20 (M+H)$^+$; $^1$H NMR (500 MHz, DMSO-d$_6$) δ 12.82 (s, 1H), 8.42-8.29 (m, 1H), 7.96-7.84 (m, 2H), 7.77-7.67 (m, 1H), 7.61-7.52 (m, 2H), 7.52-7.43 (m, 2H), 7.41-7.36 (m, 2H), 7.36-7.27 (m, 2H), 4.98 (s, 2H), 4.70 (s, 2H), 3.89 (s, 2H); Analytical HPLC RT=1.51 min (Method E), 1.52 min (Method F).

EXAMPLE 2

4-(4-(2-(5-fluoroisoindolin-2-yl)-2-oxoethyl)phenyl)phthalazin-1(2H)-one

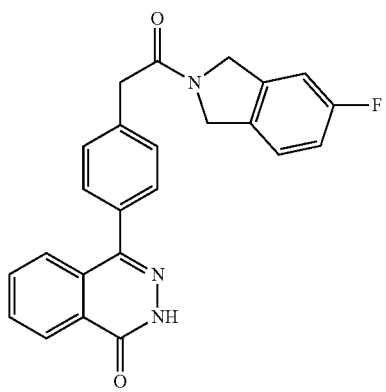 [SMILES: O=C(Cc1ccc(-c2n[nH]c(=O)c3ccccc23)cc1)N1Cc2ccc(F)cc2C1]

According a method similar to the preparation of Example 1, substitution of isoindoline with 5-fluoroisoindoline afforded Example 2.

MS (ESI) m/z: 400.1 (M+H)$^+$; $^1$H NMR (500 MHz, DMSO-d$_6$) δ 12.82 (s, 1H), 8.38-8.31 (m, 1H), 7.93-7.86 (m, 2H), 7.74-7.69 (m, 1H), 7.66-7.36 (m, 5H), 7.23 (d, J=9.1 Hz, 1H), 7.18-7.10 (m, 1H), 4.95 (d, J=16.8 Hz, 2H), 4.68 (d, J=16.8 Hz, 2H), 3.87 (s, 2H); Analytical HPLC RT=1.53 min (Method E), 1.52 min (Method F).

EXAMPLE 3

4-(4-(2-(5-methoxyisoindolin-2-yl)-2-oxoethyl)phenyl)phthalazin-1(2H)-one

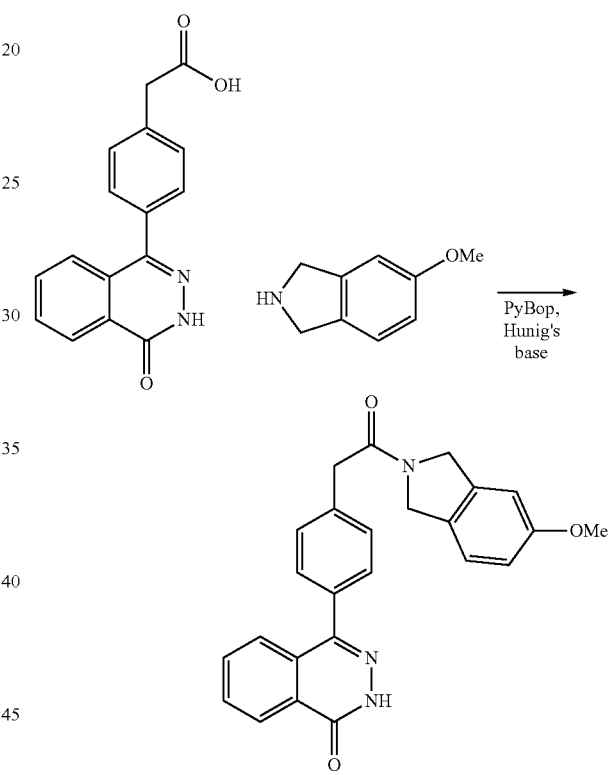

To a solution of Intermediate 1 (25 mg, 0.089 mmol) in DMF (3 mL), was added 5-methoxyisoindoline (20 mg, 0.134 mmol), PyBOP (69.6 mg, 0.134 mmol), and DIEA (0.078 mL, 0.446 mmol). The mixture was stirred at rt for 2 h, then was purified by preparative HPLC to afford 28.1 mg (59%) of Example 3.

MS (ESI) m/z: 412.2 (M+H)$^+$; $^1$H NMR (500 MHz, DMSO-d$_6$) δ 12.82 (s, 1H), 8.36-8.31 (m, 1H), 7.93-7.86 (m, 2H), 7.73-7.68 (m, 1H), 7.55 (d, J=7.7 Hz, 2H), 7.46 (d, J=8.0 Hz, 2H), 7.26 (dd, J=8.3, 4.4 Hz, 1H), 6.95 (d, J=11.6 Hz, 1H), 6.88 (dd, J=8.4, 1.8 Hz, 1H), 4.95-4.86 (m, 2H), 4.69-4.59 (m, 2H), 3.87 (s, 2H), 3.75 (s, 3H); Analytical HPLC RT=1.61 min (Method E), 1.61 min (Method F).

The following examples in Table 1 were made by using the same procedure as shown in Example 3. Intermediate 1 was coupled with the appropriate amine Various coupling reagents could be used other than the one described in Example 3 such as BOP, PyBop, EDC/HOBt or HATU.

TABLE 1

| Example | R | LCMS (M + H)+ | HPLC Method, RT (min.) | 1H NMR |
|---|---|---|---|---|
| 4 | ![1,2,3,4-tetrahydroisoquinolin-2-yl] | 396.1 | E: 1.56<br>F: 1.55 | (500 MHz, DMSO-d6) δ 12.92-12.70 (m, 1H), 8.34 (dd, J = 5.4, 2.1 Hz, 1H), 7.97-7.84 (m, 2H), 7.75-7.56 (m, 1H), 7.56-7.47 (m, 2H), 7.47-7.34 (m, 2H), 7.25-7.05 (m, 4H), 4.77 (s, 1H), 4.66 (s, 1H), 3.97-3.84 (m, 2H), 3.79 (t, J = 5.9 Hz, 1H), 3.72 (t, J = 5.9 Hz, 1H), 2.79 (t, J = 5.9 Hz, 2H) |
| 5 | NH-pyridin-3-yl | 357.1 | E: 0.95<br>F: 1.13 | (500 MHz, DMSO-d6) δ 12.83 (s, 1H), 10.69 (s, 1H), 8.92 (br. s., 1H), 8.41-8.30 (m, 2H), 8.19 (d, J = 8.5 Hz, 1H), 7.94-7.83 (m, 2H), 7.75-7.66 (m, 1H), 7.60-7.55 (m, 2H), 7.55 (d, J = 3.6 Hz, 1H), 7.54-7.50 (m, 2H), 3.83 (s, 2H) |
| 6 | NH-benzyl | 370.1 | E: 1.50<br>F: 1.50 | (500 MHz, DMSO-d6) δ 12.82 (s, 1H), 8.62 (t, J = 5.5 Hz, 1H), 8.34 (dd, J = 6.3, 2.8 Hz, 1H), 7.95-7.83 (m, 2H), 7.78-7.63 (m, 1H), 7.57-7.51 (m, J = 8.0 Hz, 2H), 7.49-7.40 (m, J = 8.0 Hz, 2H), 7.36-7.29 (m, 2H), 7.29-7.22 (m, 3H), 4.31 (d, J = 6.1 Hz, 2H), 3.60 (s, 2H) |
| 7 | NH-pyridin-4-yl | 357.1 | E: 0.98<br>F: 1.13 | (500 MHz, DMSO-d6) δ 12.84 (s, 1H), 11.39 (s, 1H), 8.65 (d, J = 6.3 Hz, 2H), 8.45-8.29 (m, 1H), 7.97 (d, J = 6.6 Hz, 2H), 7.93-7.84 (m, 2H), 7.80-7.65 (m, 1H), 7.63-7.55 (m, J = 8.0 Hz, 2H), 7.55-7.43 (m, J = 8.0 Hz, 2H), 3.93 (s, 2H) |
| 8 | N(Me)-benzyl | 384.1 | E: 1.54<br>F: 1.53 | (500 MHz, DMSO-d6) δ 12.83 (br. s., 1H), 8.41-8.29 (m, 1H), 7.96-7.85 (m, 2H), 7.73-7.63 (m, 1H), 7.60-7.14 (m, 9H), 4.81-4.50 (m, 2H), 3.95-3.82 (m, 2H), 3.10-2.80 (m, 3H) |
| 9 | NH-1H-benzimidazol-2-yl | 396.2 | E: 1.09<br>F: 1.34 | 1H NMR (500 MHz, DMSO-d6) δ 12.83 (s, 1H), 12.03 (br. s., 1H), 8.37-8.29 (m, 1H), 7.93-7.85 (m, 2H), 7.72-7.66 (m, 1H), 7.61-7.53 (m, 4H), 7.47 (dd, J = 5.8, 3.3 Hz, 2H), 7.14 (dd, J = 5.5, 3.0 Hz, 2H), 3.93 (s, 2H) |
| 10 | NH-benzoxazol-2-yl | 397.1 | E: 1.29<br>F: 1.31 | 1H NMR (500 MHz, DMSO-d6) δ 12.82 (s, 1H), 8.34 (dd, J = 6.2, 2.9 Hz, 1H), 7.94-7.83 (m, 2H), 7.76-7.67 (m, 1H), 7.58-7.45 (m, 5H), 7.26-7.20 (m, 1H), 7.20-7.15 (m, 1H), 3.87 (br. s., 2H) |

TABLE 1-continued

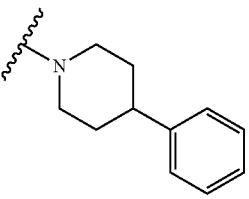 [SMILES: *N1CCC(c2ccccc2)CC1]

| Example | R | LCMS (M + H)+ | HPLC Method, RT (min.) | ¹H NMR |
|---|---|---|---|---|
| 11 | 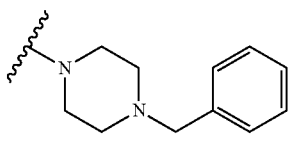 | 424.4 | C: 2.63 D: 3.80 | ¹H NMR (500 MHz, DMSO-d₆) δ 12.84 (br. s., 1H), 8.34 (d, J = 6.1 Hz, 1H), 7.88 (br. s., 2H), 7.68 (d, J = 6.7 Hz, 1H), 7.55 (d, J = 7.9 Hz, 2H), 7.44 (d, J = 7.6 Hz, 2H), 7.32-7.23 (m, 2H), 7.20 (d, J = 6.7 Hz, 3H), 4.58 (d, J = 11.3 Hz, 1H), 4.13 (d, J = 12.8 Hz, 1H), 3.87 (br. s., 2H), 3.13 (t, J = 13.0 Hz, 1H), 2.82-2.71 (m, 1H), 2.66 (t, J = 2.4 Hz, 1H), 1.77 (t, J = 14.5 Hz, 2H), 1.51-1.34 (m, 2H) |
| 12 | 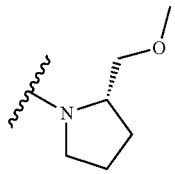 [SMILES: *N1CCC[C@H]1COC] | 439.4 | C: 2.41 D: 3.63 | ¹H NMR (500 MHz, DMSO-d₆) δ 12.84 (br. s., 1H), 8.34 (br. s., 1H), 7.89 (d, J = 3.1 Hz, 2H), 7.69 (d, J = 6.4 Hz, 1H), 7.52 (d, J = 7.3 Hz, 2H), 7.39 (d, J = 7.9 Hz, 2H), 7.35-7.19 (m, 5H), 3.81 (br. s., 2H), 3.57-3.45 (m, 6H), 2.31 (br. s., 4H) |
| 13 | 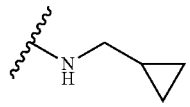 | 378.4 | C: 2.13 D: 3.24 | ¹H NMR (500 MHz, DMSO-d₆) δ 12.84 (br. s., 1H), 8.34 (d, J = 6.1 Hz, 1H), 7.90 (br. s., 2H), 7.70 (d, J = 6.4 Hz, 1H), 7.52 (d, J = 6.1 Hz, 2H), 7.40 (d, J = 7.0 Hz, 2H), 4.08 (br. s., 1H), 3.78-3.68 (m, 2H), 3.23 (br. s., 3H), 2.00-1.76 (m, 5H) |
| 14 | 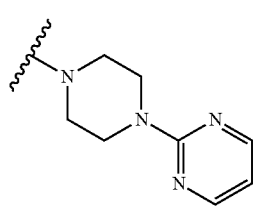 [SMILES: *N1CCN(c2ncccn2)CC1] | 334.3 | C: 1.94 D: 3.05 | ¹H NMR (400 MHz, CD₃OD/CDCl₃ (1:1)) δ 8.43 (dt, J = 4.3, 2.4 Hz, 1H), 7.84-7.64 (m, 3H), 7.55-7.46 (m, 2H), 7.42 (d, J = 8.0 Hz, 2H), 3.59 (s, 2H), 3.05 (d, J = 7.0 Hz, 2H), 0.98-0.81 (m, 1H), 0.50-0.36 (m, 2H), 0.19-0.07 (m, 2H) |
| 15 | | 427.4 | C: 2.10 D: 3.26 | ¹H NMR (500 MHz, DMSO-d₆) δ 12.83 (br. s., 1H), 8.44-8.28 (m, 3H), 7.89 (d, J = 3.7 Hz, 2H), 7.69 (br. s., 1H), 7.54 (d, J = 7.3 Hz, 2H), 7.43 (d, J = 7.6 Hz, 2H), 6.70-6.62 (m, 1H), 3.89 (br. s., 2H), 3.72 (br. s., 4H), 3.65 (br. s., 2H), 3.59 (br. s., 2H) |

TABLE 1-continued

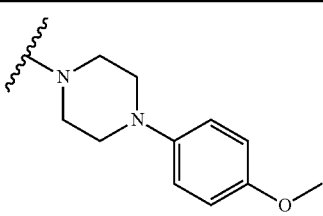

| Example | R | LCMS (M + H)+ | HPLC Method, RT (min.) | 1H NMR |
|---|---|---|---|---|
| 16 | 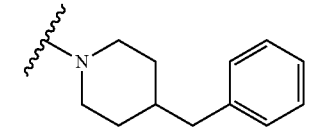 [SMILES: *N1CCC(Cc2ccccc2)CC1] | 455.4 | C: 2.23<br>D: 3.47 | 1H NMR (500 MHz, DMSO-d6) δ 12.83 (br. s., 1H), 8.33 (br. s., 1H), 7.88 (br. s., 2H), 7.68 (br. s., 1H), 7.53 (d, J = 7.9 Hz, 2H), 7.42 (d, J = 7.6 Hz, 2H), 6.95-6.85 (m, 2H), 6.82 (d, J = 8.5 Hz, 2H), 3.88 (br. s., 2H), 3.68 (br. s., 4H), 3.64 (br. s., 2H), 2.96 (br. s., 4H) |
| 17 | 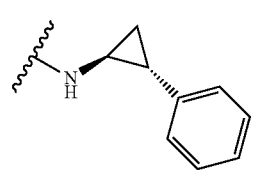 [SMILES: *N[C@H]1C[C@@H]1c1ccccc1] | 438.4 | C: 2.77<br>D: 4.04 | 1H NMR (500 MHz, DMSO-d6) δ 12.84 (br. s., 1H), 8.34 (br. s., 1H), 7.90 (d, J = 3.7 Hz, 2H), 7.69 (d, J = 5.8 Hz, 1H), 7.52 (d, J = 7.9 Hz, 2H), 7.39 (d, J = 7.6 Hz, 2H), 7.30-7.21 (m, 2H), 7.21-7.10 (m, 3H), 4.38 (d, J = 13.1 Hz, 1H), 3.98 (d, J = 11.6 Hz, 1H), 3.80 (br. s., 2H), 2.96 (t, J = 12.4 Hz, 1H), 1.75 (br. s., 1H), 1.56 (br. s., 2H), 0.99 (t, J = 10.2 Hz, 2H) |
| 18 | 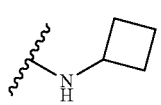 [SMILES: *NC1CCC1] | 396.4 | C: 2.35<br>D: 3.56 | 1H NMR (500 MHz, DMSO-d6) δ 12.84 (br. s., 1H), 8.49 (br. s., 1H), 8.34 (br. s., 1H), 7.90 (d, J = 3.7 Hz, 2H), 7.71 (d, J = 5.5 Hz, 1H), 7.54 (d, J = 7.6 Hz, 2H), 7.44 (d, J = 7.3 Hz, 2H), 7.29-7.21 (m, 2H), 7.19-7.06 (m, 3H), 3.52 (br. s., 2H), 2.85 (br. s., 1H), 1.97 (br. s., 1H), 1.18 (d, J = 5.8 Hz, 2H) |
| 19 | 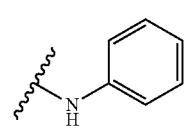 [SMILES: *Nc1ccccc1] | 334.3 | C: 1.95<br>D: 3.11 | 1H NM (500 MHz, DMSO-d6) δ 12.83 (br. s., 1H), 8.40 (d, J = 6.1 Hz, 1H), 8.33 (br. s., 1H), 7.89 (d, J = 3.4 Hz, 2H), 7.69 (d, J = 6.7 Hz, 1H), 7.51 (d, J = 7.6 Hz, 2H), 7.41 (d, J = 7.9 Hz, 2H), 4.25-4.11 (m, 1H), 3.46 (s, 2H), 2.22-2.11 (m, 2H), 1.96-1.83 (m, 2H), 1.70-1.55 (m, 2H) |
| 20 | 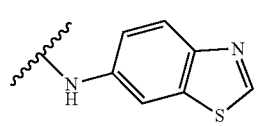 [SMILES: *Nc1ccc2ncsc2c1] | 356.3 | C: 2.21<br>D: 3.36 | 1H NMR (500 MHz, DMSO-d6) δ 12.83 (br. s., 1H), 10.25 (br. s., 1H), 8.33 (br. s., 1H), 7.88 (d, J = 4.0 Hz, 2H), 7.70 (br. s., 1H), 7.62 (d, J = 7.6 Hz, 2H), 7.59-7.46 (m, 4H), 7.34-7.25 (m, 2H), 7.09-6.99 (m, 1H), 3.76 (br. s., 2H) |
| 21 | | 413.4 | C: 1.96<br>D: 3.20 | 1H NMR (500 MHz, DMSO-d6) δ 12.85 (br. s., 1H), 10.65 (br. s., 1H), 9.26 (br. s., 1H), 8.58 (br. s., 1H), 8.33 (br. s., 1H), 8.02 (d, J = 8.9 Hz, 1H), 7.89 (br. s., 2H), 7.71 (br. s., 1H), 7.65 (d, J = 9.5 Hz, 1H), 7.55 (br. s, 4H), 3.82 (br. s., 2H) |

TABLE 1-continued

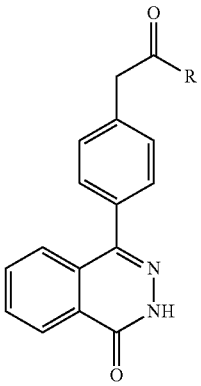

| Example | R | LCMS (M + H)+ | HPLC Method, RT (min.) | 1H NMR |
|---|---|---|---|---|
| 22 | 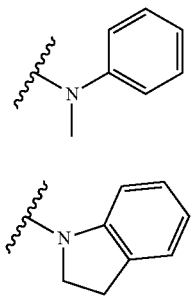 | 370.3 | C: 2.25<br>D: 3.52 | 1H NMR (500 MHz, DMSO-d6) δ 12.83 (br. s., 1H), 8.33 (d, J = 6.7 Hz, 1H), 7.89 (br. s., 2H), 7.73-7.62 (m, J = 7.3 Hz, 1H), 7.54 (d, J = 7.3 Hz, 1H), 7.47 (br. s., 3H), 7.39 (d, J = 7.9 Hz, 4H), 7.20 (br. s., 1H), 3.51 (br. s., 2H), 3.21 (br. s., 3H) |
| 23 | 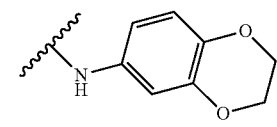 [SMILES: *Nc1ccc2c(c1)OCCO2] | 382.3 | C: 2.48<br>D: 3.67 | 1H NMR (500 MHz, DMSO-d6) δ 12.85 (br. s., 1H), 8.34 (d, J = 7.3 Hz, 1H), 8.08 (d, J = 7.6 Hz, 1H), 7.96-7.84 (m, 2H), 7.72 (d, J = 7.3 Hz, 1H), 7.59-7.51 (m, 2H), 7.47 (d, J = 7.0 Hz, 2H), 7.24 (d, J = 6.4 Hz, 1H), 7.18-7.10 (m, 1H), 7.00 (t, J = 6.6 Hz, 1H), 4.26-4.17 (m, 2H), 3.96 (br. s., 2H), 3.20-3.14 (m, J = 9.2 Hz, 2H) |
| 24 | 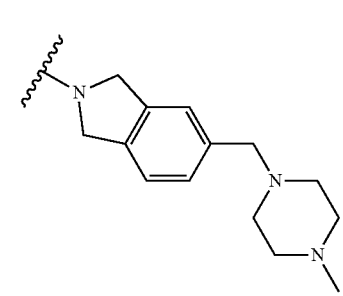 [SMILES: *N1Cc2ccc(CN3CCN(C)CC3)cc2C1] | 414.3 | C: 2.13<br>D: 3.25 | 1H NMR (500 MHz, DMSO-d6) δ 12.84 (br. s., 1H), 10.09 (br. s., 1H), 8.39-8.27 (m, 1H), 7.89 (d, J = 2.4 Hz, 2H), 7.74-7.65 (m, 1H), 7.58-7.51 (m, 2H), 7.49 (d, J = 6.7 Hz, 2H), 7.26 (br. s., 1H), 6.99 (d, J = 6.4 Hz, 1H), 6.78 (d, J = 8.9 Hz, 1H), 4.20 (d, J = 6.4 Hz, 4H), 3.70 (br. s., 2H) |
| 25 | 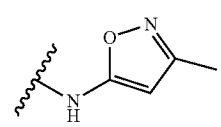 [SMILES: *Nc1cc(C)no1] | 494.3 | E: 0.94<br>F: 1.15 | 1H NMR (500 MHz, DMSO-d6) δ 12.82 (s, 1H), 8.37-8.30 (m, 1H), 7.93-7.86 (m, 2H), 7.71 (d, J = 7.2 Hz, 1H), 7.55 (d, J = 7.7 Hz, 2H), 7.47 (d, J = 7.7 Hz, 2H), 7.33-7.25 (m, 2H), 7.23 (d, J = 7.7 Hz, 1H), 4.95 (d, J = 7.4 Hz, 2H), 4.67 (d, J = 4.7 Hz, 2H), 3.87 (s, 2H), 3.46 (d, J = 3.3 Hz, 2H), 2.36 (br. s., 8H), 2.17 (br. s., 3H) |
| 26 | 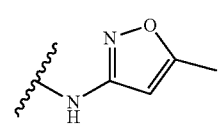 [SMILES: *Nc1cc(C)on1] | 361.2 | C: 2.06<br>D: 3.11 | 1H NMR (500 MHz, DMSO-d6) δ 12.84 (br. s., 1H), 8.33 (br. s., 1H), 7.89 (br. s., 2H), 7.69 (br. s., 1H), 7.56 (d, J = 7.3 Hz, 2H), 7.48 (d, J = 4.9 Hz, 2H), 6.12 (br. s., 1H), 3.82 (br. s., 2H), 2.17 (br. s., 3H) |
| 27 |  | 361.2 | C: 2.06<br>D: 3.08 | 1H NMR (500 MHz, DMSO-d6) δ 12.84 (br. s., 1H), 11.21 (br. s., 1H), 8.33 (br. s., 1H), 7.89 (d, J = 3.1 Hz, 2H), 7.70 (br. s., 1H), 7.55 (d, J = 7.3 Hz, 2H), 7.49 (d, J = 7.0 Hz, 2H), 6.62 (br. s., 1H), 3.78 (br. s., 2H), 2.36 (br. s., 3H) |

TABLE 1-continued

| Example | R | LCMS (M + H)+ | HPLC Method, RT (min.) | 1H NMR |
|---|---|---|---|---|
| 28 | thiazol-2-ylamino | 363.2 | C: 2.07<br>D: 3.13 | 1H NMR (400 MHz, DMSO-d6) δ 12.86 (br. s., 1H), 8.36-8.30 (m, 1H), 7.93-7.86 (m, 2H), 7.73-7.69 (m, 1H), 7.58-7.53 (m, 2H), 7.53-7.48 (m, 2H), 7.42 (d, J = 3.5 Hz, 1H), 7.09 (br. s., 1H), 3.83 (s, 2H) |
| 29 | 1,3,4-thiadiazol-2-ylamino | 364.2 | C: 1.84<br>D: 2.87 | 1H NMR (400 MHz, DMSO-d6) δ 12.85 (s, 1H), 9.11 (s, 1H), 8.37-8.30 (m, 1H), 7.95-7.85 (m, 2H), 7.74-7.68 (m, 1H), 7.59-7.53 (m, 2H), 7.53-7.48 (m, 2H), 3.92 (s, 2H) |
| 30 | 6-chloropyridazin-3-ylamino | 392.2 | C: 2.12<br>D: 3.18 | 1H NMR (400 MHz, DMSO-d6) δ 12.86 (br. s., 1H), 11.67 (br. s., 1H), 8.40 (d, J = 9.5 Hz, 1H), 8.36-8.30 (m, 1H), 7.94-7.85 (m, 3H), 7.74-7.66 (m, 1H), 7.60-7.55 (m, 2H), 7.55-7.49 (m, 2H), 3.92 (s, 2H) |
| 31 | 5-methyl-1,3,4-thiadiazol-2-ylamino | 378.2 | C: 1.81<br>D: 3.07 | 1H NMR (400 MHz, DMSO-d6) δ 12.86 (s, 1H), 12.70 (br. s., 1H), 8.36-8.30 (m, 1H), 7.93-7.85 (m, 2H), 7.75-7.66 (m, 1H), 7.60-7.53 (m, 2H), 7.53-7.46 (m, 2H), 3.92 (s, 2H), 2.60 (s, 3H) |
| 32 | 5-methylindolin-1-yl | 396.1 | A: 9.56<br>B: 9.14 | (500 MHz, DMSO-d6) δ 12.83 (s, 1H), 8.41-8.29 (m, 1H), 7.96 (d, J = 8.3 Hz, 1H), 7.91-7.85 (m, 2H), 7.73-7.68 (m, 1H), 7.62-7.52 (m, J = 8.3 Hz, 2H), 7.48-7.42 (m, J = 8.0 Hz, 2H), 7.05 (s, 1H), 6.95 (d, J = 8.3 Hz, 1H), 4.21 (t, J = 8.5 Hz, 2H), 3.94 (s, 2H), 3.14 (t, J = 8.4 Hz, 2H), 2.25 (s, 3H) |
| 33 | 6-ethoxyindolin-1-yl | 426.1 | A: 9.62<br>B: 9.23 | (500 MHz, DMSO-d6) δ 12.83 (s, 1H), 8.42-8.30 (m, 1H), 7.94-7.84 (m, 2H), 7.80-7.65 (m, 2H), 7.62-7.51 (m, J = 8.0 Hz, 2H), 7.51-7.40 (m, J = 8.3 Hz, 2H), 7.11 (d, J = 8.0 Hz, 1H), 6.56 (dd, J = 8.0, 2.5 Hz, 1H), 4.24 (t, J = 8.3 Hz, 2H), 4.02-3.89 (m, 4H), 3.09 (t, J = 8.3 Hz, 3H), 1.30 (t, J = 7.0 Hz, 3H) |
| 34 | 3,4-dihydroquinolin-1(2H)-yl | 396.1 | E: 1.70<br>F: 1.73 | (500 MHz, DMSO-d6) δ 12.81 (s, 1H), 8.37-8.29 (m, 1H), 7.95-7.87 (m, 2H), 7.66 (d, J = 7.7 Hz, 1H), 7.49 (d, J = 7.7 Hz, 3H), 7.33 (br. s., 2H), 7.19 (d, J = 6.9 Hz, 2H), 7.13 (d, J = 7.2 Hz, 1H), 3.99 (s, 2H), 3.75 (t, J = 6.2 Hz, 2H), 2.66 (br. s., 2H), 1.86 (quin, J = 6.5 Hz, 2H) |

TABLE 1-continued

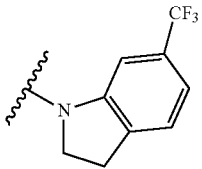 [SMILES: *N1CCc2ccc(C(F)(F)F)cc21]

| Example | R | LCMS (M + H)⁺ | HPLC Method, RT (min.) | ¹H NMR |
|---|---|---|---|---|
| 35 | 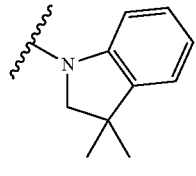 [SMILES: *N1CC(C)(C)c2ccccc21] | 450.2 | E: 1.91<br>F: 1.96 | (500 MHz, DMSO-d₆) δ 12.83 (s, 1H), 8.42-8.30 (m, 2H), 7.98-7.84 (m, 2H), 7.80-7.67 (m, 1H), 7.57 (d, J = 8.0 Hz, 2H), 7.48 (d, J = 8.3 Hz, 3H), 7.37 (d, J = 7.7 Hz, 1H), 4.32 (t, J = 8.5 Hz, 2H), 4.01 (s, 2H), 3.29-3.24 (m, 2H) |
| 39 | 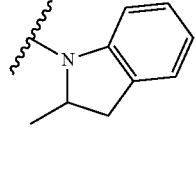 [SMILES: *N1c2ccccc2CC1C] | 410.15 | E: 1.88<br>F: 1.89 | (500 MHz, DMSO-d₆) δ 12.85 (br. s., 1H), 8.38-8.32 (m, 1H), 8.06 (d, J = 8.4 Hz, 1H), 7.93-7.86 (m, 2H), 7.76-7.68 (m, 1H), 7.61-7.53 (m, J = 8.4 Hz, 2H), 7.50-7.44 (m, J = 7.9 Hz, 2H), 7.27 (d, J = 7.4 Hz, 1H), 7.17 (t, J = 7.4 Hz, 1H), 7.08-7.00 (m, 1H), 3.98 (d, J = 8.9 Hz, 4H), 1.31 (s, 6H) |
| 40 | 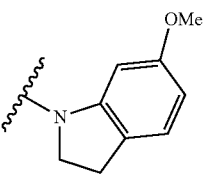 [SMILES: *N1CCc2ccc(OC)cc21] | 396.15 | E: 1.75<br>F: 1.77 | (500 MHz, CD₃OD) δ 8.47-8.41 (m, 1H), 8.10 (d, J = 8.4 Hz, 1H), 7.88-7.77 (m, 3H), 7.63-7.55 (m, 3H), 7.49 (d, J = 7.4 Hz, 2H), 7.25-7.17 (m, 2H), 7.06 (t, J = 7.4 Hz, 1H), 4.05 (d, J = 15.4 Hz, 1H), 3.95 (d, J = 15.9 Hz, 1H), 3.43 (dd, J = 15.6, 8.7 Hz, 1H), 2.72 (d, J = 15.4 Hz, 1H), 1.38 (d, J = 5.9 Hz, 3H), 1.29 (br. s., 1H) |
| 41 |  | 412.0 | A: 8.50<br>B: 7.65 | (500 MHz, DMSO-d₆) δ 12.83 (s, 1H), 8.45-8.27 (m, 1H), 7.94-7.85 (m, 2H), 7.79-7.67 (m, 2H), 7.63-7.53 (m, J = 8.0 Hz, 2H), 7.52-7.43 (m, J = 8.0 Hz, 2H), 7.13 (d, J = 8.3 Hz, 1H), 6.58 (dd, J = 8.3, 2.2 Hz, 1H), 4.25 (t, J = 8.4 Hz, 2H), 3.96 (s, 2H), 3.70 (s, 3H), 3.10 (t, J = 8.4 Hz, 2H) |

EXAMPLE 36

2-(2-fluoro-4-(4,4,5,5-tetramethyl-1,3,2-dioxaborolan-2-yl)phenyl)-1-(isoindolin-2-yl)ethanone

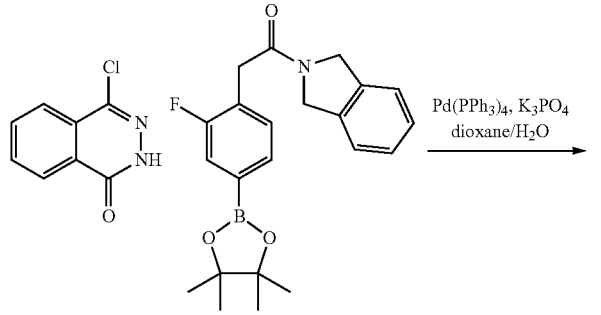

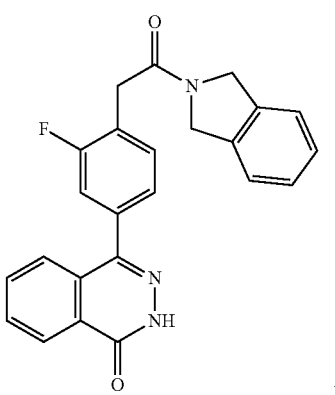

To a vial containing Intermediate 4 (34.8 mg, 0.091 mmol), 4-chlorophthalazin-1(2H)-one (15 mg, 0.083 mmol) and potassium phosphate (44 mg, 0.21 mmol), were added dioxane (0.9 mL) and water (0.1 mL). The mixture was degassed (evacuated and flushed with Ar (3×)). To this mixture was added Pd(Ph₃P)₄ (4.8 mg, 4.2 μmol). The mixture was degassed (3×), then the vial was sealed. The vial was heated in a microwave reactor at 150° C. for 25 min. The mixture was concentrated, then was diluted with 4 mL 1:1 DMSO/MeOH. TFA (0.1 mL) was added, then the suspension was filtered and the solid collected. The solid was washed with H₂O (~5 mL), then MeOH (~5 mL), sucked dry and dried in vacuo to afford 34.8 mg (42%) of Example 36 as a white solid.

MS (ESI) m/z: 400.0 (M+H)⁺; ¹H NMR (500 MHz, DMSO-$d_6$) δ 12.89 (s, 1H), 8.38-8.32 (m, 1H), 7.92 (quind, J=7.1, 1.7 Hz, 2H), 7.76-7.71 (m, 1H), 7.51 (t, J=7.8 Hz, 1H), 7.43 (dd, J=10.5, 1.4 Hz, 1H), 7.41-7.37 (m, 3H), 7.35-7.30 (m, 2H), 5.02 (s, 2H), 4.71 (s, 2H), 3.92 (s, 2H); HPLC RT=7.96 min (Method A), 8.02 min (Method B).

EXAMPLE 37

4-(2-fluoro-4-(2-(isoindolin-2-yl)-2-oxoethyl)phenyl)phthalazin-1(2H)-one

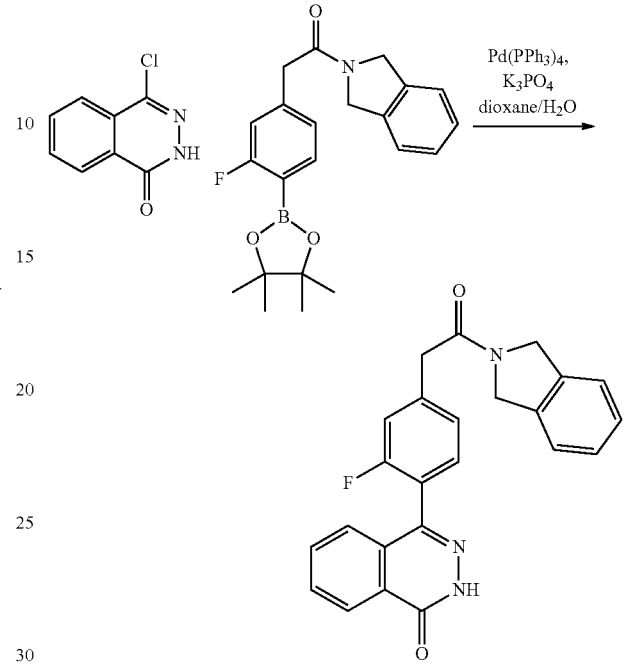

To a vial containing Intermediate 5 (34.8 mg, 0.091 mmol), 4-chlorophthalazin-1(2H)-one (15 mg, 0.083 mmol) and potassium phosphate (44.1 mg, 0.208 mmol), were added dioxane (0.9 mL) and water (0.1 mL). The mixture was degassed (evacuated and flushed with Ar (3×)). To this mixture was added Pd(Ph₃P)₄ (4.8 mg, 4.15 μmol). The mixture was degassed (3×), then the vial was sealed. The vial was heated in a microwave reactor at 150° C. for 25 min. The reaction mixture separated into two phases upon cooling. The organic phase was collected and was purified by preparative HPLC to afford 11.7 mg (35%) of Example 37.

MS (ESI) m/z: 400.2 (M+H)⁺; ¹H NMR (500 MHz, DMSO-$d_6$) δ 12.94 (br. s., 1H), 8.37-8.29 (m, 1H), 7.92-7.86 (m, 2H), 7.65-7.49 (m, 4H), 7.45-7.28 (m, 4H), 4.99 (s, 2H), 4.71 (s, 2H), 3.93 (s, 2H); HPLC RT=1.56 min (Method E), 1.52 min (Method F).

EXAMPLE 38

4-(4-(2-(isoindolin-2-yl)-2-oxoethyl)phenyl)isoquinolin-1(2H)-one

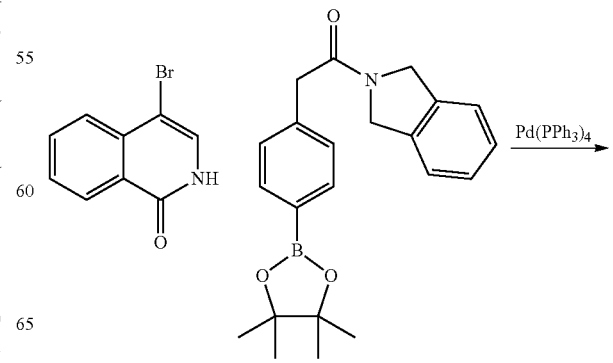

-continued

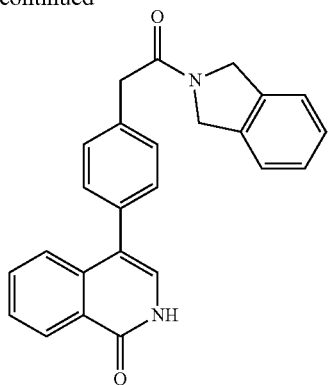

According to the procedure for the preparation of Example 36, coupling of Intermediate 6 (30 mg, 0.13 mmol) and Intermediate 9 (51 mg, 0.14 mmol) afforded 17 mg (33%) of Example 38.

MS (ESI) m/z: 381.1 (M+H)$^+$; $^1$H NMR (500 MHz, DMSO-d$_6$) δ 11.43 (d, J=5.8 Hz, 1H), 8.29 (dd, J=8.1, 1.2 Hz, 1H), 7.69 (td, J=7.7, 1.4 Hz, 1H), 7.61-7.51 (m, 2H), 7.44-7.35 (m, 6H), 7.33-7.28 (m, 2H), 7.08 (s, 1H), 4.97 (s, 2H), 4.69 (s, 2H), 3.84 (s, 2H); HPLC RT=8.20 min (Method A), 7.53 min (Method B).

EXAMPLE 42

4-(4-(1-(indolin-1-yl)-1-oxopropan-2-yl)phenyl)phthalazin-1(2H)-one

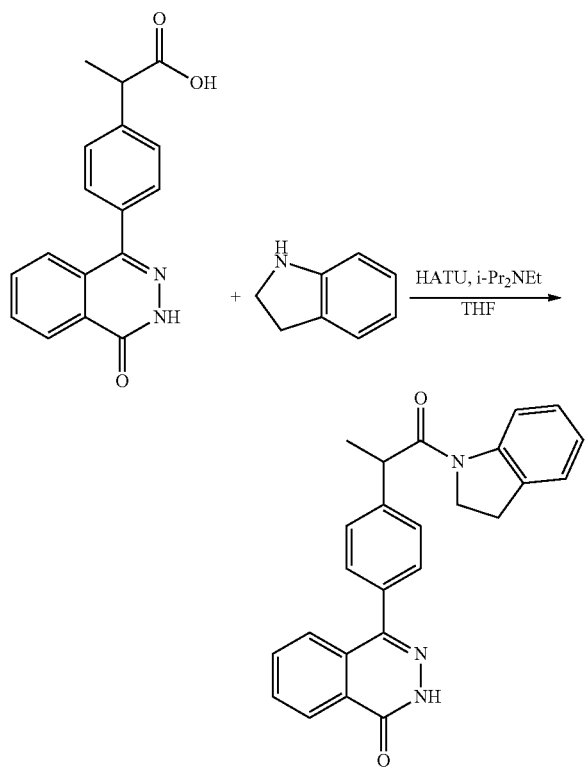

According to the procedure for the preparation of Example 3, coupling of Intermediate 11 (13 mg, 0.044 mmol) and indoline (7.9 mg, 0.066 mmol) using HATU afforded 8.2 mg (46%) of Example 42.

MS (ESI) m/z: 396.15 (M+H)$^+$; $^1$H NMR (500 MHz, DMSO-d$_6$) δ 12.85 (s, 1H), 8.38-8.30 (m, 1H), 8.18 (d, J=8.4 Hz, 1H), 7.92-7.84 (m, 2H), 7.74-7.68 (m, 1H), 7.62-7.55 (m, J=8.4 Hz, 2H), 7.55-7.49 (m, J=8.4 Hz, 2H), 7.20 (d, J=7.4 Hz, 1H), 7.16 (t, J=7.7 Hz, 1H), 7.02-6.94 (m, 1H), 4.37 (td, J=10.4, 6.4 Hz, 1H), 4.23 (q, J=6.4 Hz, 1H), 3.91-3.75 (m, 1H), 3.16-3.00 (m, 2H), 1.46 (d, J=6.4 Hz, 3H); HPLC RT=1.77 min (Method E), 1.75 min (Method F).

EXAMPLE 43

4-(4-(1-(isoindolin-2-yl)-1-oxopropan-2-yl)phenyl)phthalazin-1(2H)-one

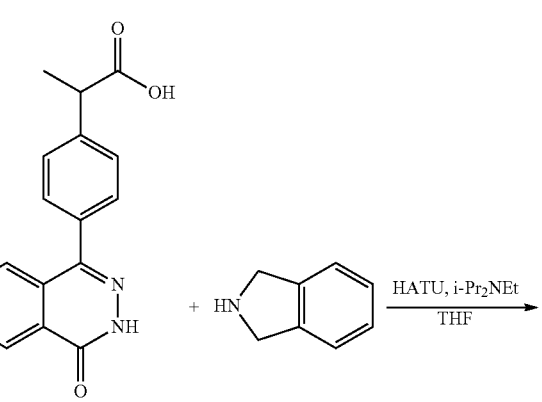

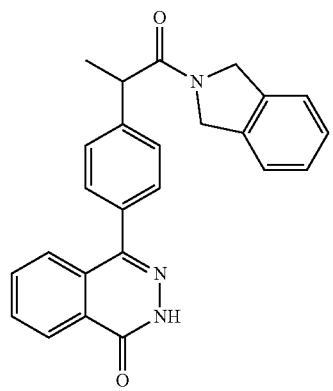

According to the procedure for the preparation of Example 3, coupling of Intermediate 11 (13 mg, 0.044 mmol) and isoindoline (7.9 mg, 0.066 mmol) using HATU afforded 9.0 mg (52%) of Example 43.

MS (ESI) m/z: 396.15 (M+H)$^+$; $^1$H NMR (500 MHz, 1:1 CD$_3$OD/CDCl$_3$) δ 8.49-8.43 (m, 1H), 7.90-7.83 (m, 2H), 7.83-7.78 (m, 1H), 7.61-7.58 (m, 2H), 7.57-7.52 (m, 2H), 7.35-7.23 (m, 4H), 5.04 (d, J=13.9 Hz, 1H), 4.92-4.85 (m, 1H), 4.83-4.77 (m, 1H), 4.66 (d, J=13.9 Hz, 1H), 4.09 (q, J=6.9 Hz, 1H), 1.58 (d, J=6.9 Hz, 3H).

EXAMPLE 44

N-(4-(4-oxo-3,4-dihydrophthalazin-1-yl)phenyl)-2,3-dihydro-1H-indene-2-carboxamide

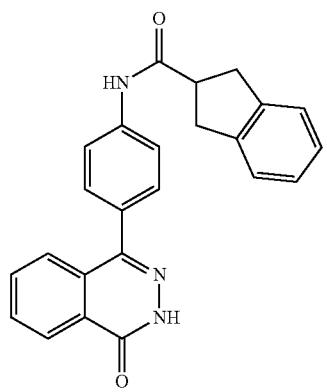 [SMILES: O=C(Nc1ccc(-c2n[nH]c(=O)c3ccccc23)cc1)C1Cc2ccccc2C1]

EXAMPLE 44A

N-(4-bromophenyl)-2,3-dihydro-1H-indene-2-carboxamide

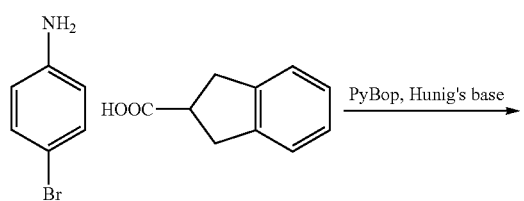

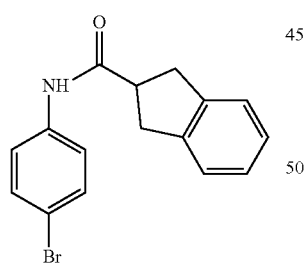

To a solution of 2,3-dihydro-1H-indene-2-carboxylic acid (141 mg, 0.872 mmol) in DMF (3 mL), were added 4-bromoaniline (150 mg, 0.872 mmol), PyBOP (499 mg, 0.959 mmol), and DIEA (0.457 mL, 2.62 mmol). The mixture was stirred at rt for 16 h. The reaction mixture was concentrated and the residue was dissolved in EtOAc, washed with 10% LiCl, 1N HCl and brine. The crude product was purified via flash chromatography to afford 90 mg (33%) of Example 44A.

MS (ESI) m/z: 316.0 (M+H)$^+$.

EXAMPLE 44B

N-(4-(4,4,5,5-tetramethyl-1,3,2-dioxaborolan-2-yl)phenyl)-2,3-dihydro-1H-indene-2-carboxamide

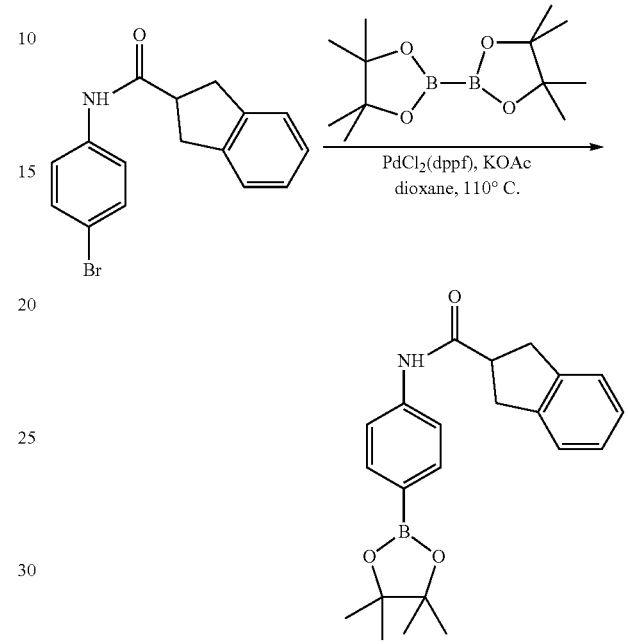

A mixture of Example 44A (62 mg, 0.20 mmol), bis(pinacolato)diboron (74.7 mg, 0.294 mmol), and potassium acetate (57.7 mg, 0.588 mmol) in dioxane (3 mL) was degassed (3× vacuum/Ar). PdCl$_2$(dppf) CH$_2$Cl$_2$ adduct (4.3 mg, 5.9 µmol) was added. The reaction mixture was degassed again (3× vacuum/Ar), sealed in a vial and heated at 110° C. for 2 h. The reaction mixture was filtered and concentrated to afford 40 mg (56%) of Example 44B, which was used as is in the following step.

MS (ESI) m/z: 364.2 (M+H)$^+$.

EXAMPLE 44

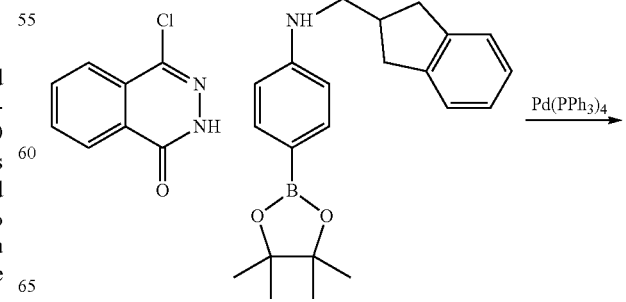

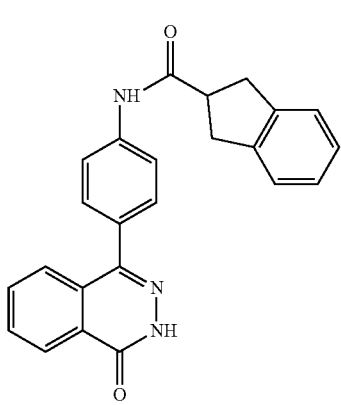

To 4-chlorophthalazin-1(2H)-one (28.3 mg, 0.157 mmol), Example 44B (40 mg, 0.11 mmol) and potassium phosphate (76 mg, 0.36 mmol), were added dioxane (3 mL) and water (0.5 mL). The mixture was degassed (evacuated and flushed with Ar (5×)). Pd(PPh$_3$)$_4$ (8.2 mg, 7.1 μmol) was added, then the mixture was degassed (2×). The reaction vial was sealed and heated in a microwave reactor at 150° C. for 25 min. The reaction mixture was concentrated, then was purified by preparative HPLC to yield 17.1 mg (24%) of Example 44.

MS (ESI) m/z: 382.1 (M+H)$^+$; $^1$H NMR (500 MHz, DMSO-d$_6$) δ 12.79 (s, 1H), 10.26 (s, 1H), 8.38-8.31 (m, 1H), 7.93-7.85 (m, 2H), 7.84-7.79 (m, J=8.5 Hz, 2H), 7.76-7.69 (m, 1H), 7.59-7.50 (m, J=8.5 Hz, 2H), 7.24 (dd, J=5.1, 3.4 Hz, 2H), 7.15 (dd, J=5.4, 3.2 Hz, 2H), 3.46 (t, J=8.5 Hz, 1H), 3.21 (dd, J=8.4, 3.2 Hz, 4H); HPLC RT=1.67 min (Method E), 1.66 min (Method F).

EXAMPLE 45

N-(4-(4-oxo-3,4-dihydrophthalazin-1-yl)phenyl)-2-(pyridin-4-yl)thiazole-4-carboxamide

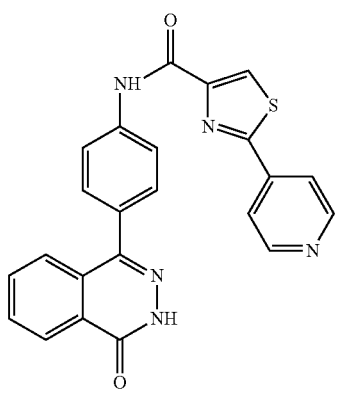

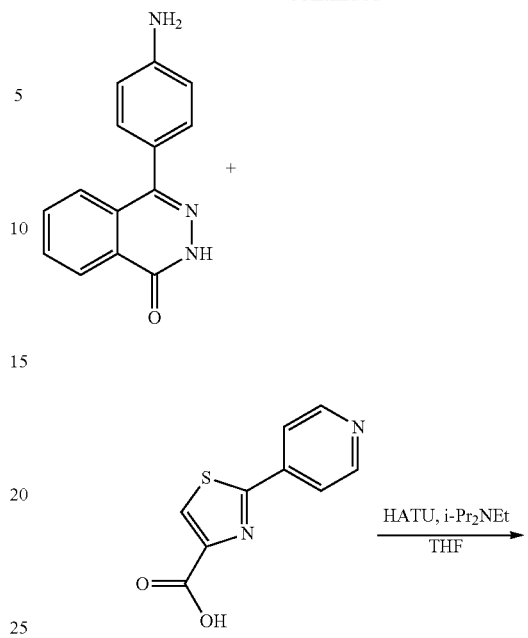

To a mixture of Intermediate 3 (25 mg, 0.105 mmol), 2-(pyridin-4-yl)thiazole-4-carboxylic acid (44 mg, 0.21 mmol), and HATU (60 mg, 0.16 mmol) in THF (1 mL), were added DIEA (0.046 mL, 0.26 mmol) and DMF (1 mL). The mixture was stirred at rt for 2 h, then was concentrated. The crude product was purified via preparative HPLC to afford 25 mg (36%) of Example 45.

MS (ESI) m/z: 426.0 (M+H)$^+$; $^1$H NMR (500 MHz, DMSO-d$_6$) δ 12.84 (s, 1H), 10.53 (s, 1H), 8.86 (d, J=4.1 Hz, 2H), 8.73 (s, 1H), 8.44-8.32 (m, 1H), 8.25 (d, J=6.1 Hz, 2H), 8.12-8.02 (m, 2H), 7.97-7.86 (m, 2H), 7.82-7.76 (m, 1H), 7.68-7.60 (m, 2H); HPLC RT=5.13 min (Method A), 5.69 min (Method B).

The following examples in Table 2 were made by using the same procedure as shown in Example 45. Intermediate 3 was coupled with the appropriate carboxylic acid. Various coupling reagents could be used other than the one described in Example 45, such as BOP, PyBop, EDC/HOBt or T3P.

TABLE 2
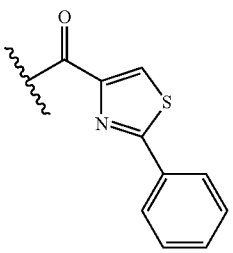 [SMILES: *C(=O)c1csc(-c2ccccc2)n1]
| Example | R | LCMS (M + H)⁺ | HPLC Method, RT (min.) | ¹H NMR |
|---|---|---|---|---|
| 46 | 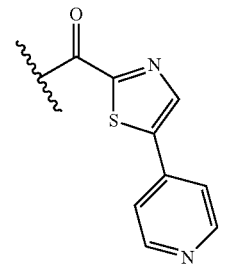 [SMILES: *C(=O)c1ncc(-c2ccncc2)s1] | 425.1 | E: 1.83<br>F: 1.88 | (500 MHz, DMSO-d₆) δ 12.83 (br. s., 1H), 10.44 (br. s., 1H), 8.58-8.51 (m, 1H), 8.35 (dd, J = 7.6, 1.2 Hz, 1H), 8.18 (dd, J = 7.6, 2.1 Hz, 2H), 8.11-8.04 (m, J = 8.5 Hz, 2H), 8.00-7.86 (m, 2H), 7.78 (d, J = 7.4 Hz, 1H), 7.66-7.61 (m, J = 8.5 Hz, 2H), 7.61-7.55 (m, 3H) |
| 47 | 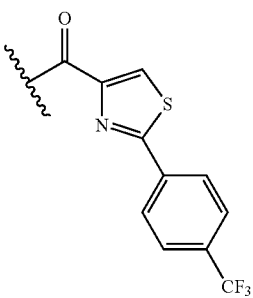 [SMILES: *C(=O)c1csc(-c2ccc(C(F)(F)F)cc2)n1] | 426.0 | E: 1.11<br>F: 1.52 | (500 MHz, DMSO-d₆) δ 12.85 (s, 1H), 10.91 (s, 1H), 8.96 (s, 1H), 8.82 (d, J = 5.8 Hz, 2H), 8.40-8.33 (m, 1H), 8.30 (d, J = 5.8 Hz, 2H), 8.09-8.01 (m, J = 8.5 Hz, 2H), 7.96-7.87 (m, 2H), 7.77 (d, J = 7.4 Hz, 1H), 7.71-7.63 (m, J = 8.5 Hz, 2H) |
| 48 | 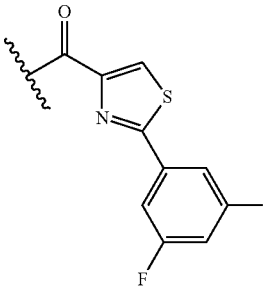 | 493.2 | E: 1.98<br>F: 1.99 | (500 MHz, DMSO-d₆) δ 12.83 (s, 1H), 10.52 (s, 1H), 8.64 (s, 1H), 8.41 (d, J = 8.3 Hz, 2H), 8.38-8.32 (m, 1H), 8.10-8.03 (m, J = 8.5 Hz, 2H), 7.98-7.86 (m, 4H), 7.81-7.74 (m, 1H), 7.67-7.56 (m, J = 8.5 Hz, 2H) |
| 49 |  | 461.2 | E: 1.87<br>F: 1.88 | 1H NMR (500 MHz, DMSO-d₆) δ 12.83 (s, 1H), 10.51 (s, 1H), 8.77-8.68 (m, 1H), 8.63 (s, 1H), 8.35 (dd, J = 7.6, 1.2 Hz, 1H), 8.13-8.02 (m, J = 8.5 Hz, 2H), 7.98-7.85 (m, 2H), 7.81-7.74 (m, 1H), 7.65-7.61 (m, J = 8.5 Hz, 2H), 7.58 (ddd, J = 11.6, 9.2, 2.3 Hz, 1H), 7.45-7.34 (m, 1H) |

TABLE 2-continued

[Structure: 4-(4-(R-amino)phenyl)phthalazin-1(2H)-one core with HN-R substituent]

| Example | R | LCMS (M + H)+ | HPLC Method, RT (min.) | 1H NMR |
|---------|---|---------------|------------------------|--------|
| 50 | [2-acyl-4-methylthiazole] | 363.2 | E: 1.46<br>F: 1.47 | (500 MHz, DMSO-d$_6$) δ 12.82 (s, 1H), 10.91 (s, 1H), 8.34 (dd, J = 7.6, 1.5 Hz, 1H), 8.10-8.00 (m, J = 8.8 Hz, 2H), 7.91 (td, J = 7.4, 1.4 Hz, 2H), 7.78-7.70 (m, 2H), 7.63-7.53 (m, J = 8.5 Hz, 1H), 2.53 (s, 3H) |
| 51 | [2-acyl-5-methyl-4,5,6,7-tetrahydrothiazolo[5,4-c]pyridine] | 418.2 | E: 0.98<br>F: 1.31 | (500 MHz, DMSO-d$_6$) δ 12.82 (s, 1H), 10.92 (s, 1H), 8.34 (d, J = 7.2 Hz, 1H), 8.08-8.00 (m, J = 8.5 Hz, 2H), 7.96-7.84 (m, 2H), 7.74 (d, J = 7.7 Hz, 1H), 7.63-7.54 (m, J = 8.5 Hz, 2H), 3.72 (s, 2H), 2.97-2.92 (m, 2H), 2.83-2.76 (m, 2H), 2.42 (s, 3H) |
| 52 | [2-acyl-1-methylimidazole] | 346.2 | E: 1.03<br>F: 1.26 | (500 MHz, DMSO-d$_6$) δ 12.81 (s, 1H), 10.55 (s, 1H), 8.38-8.29 (m, 1H), 8.06-7.98 (m, J = 8.5 Hz, 2H), 7.94-7.86 (m, 2H), 7.75 (d, J = 7.4 Hz, 1H), 7.62-7.53 (m, J = 8.5 Hz, 2H), 7.47 (s, 1H), 7.11 (s, 1H), 4.02 (s, 3H) |
| 53 | [2-acyl-4,5,6,7-tetrahydrobenzothiazole] | 403.15 | E: 1.70<br>F: 1.71 | (500 MHz, DMSO-d$_6$) δ 12.82 (s, 1H), 10.85 (s, 1H), 8.34 (dd, J = 7.6, 1.2 Hz, 1H), 8.07-8.01 (m, J = 8.5 Hz, 2H), 7.96-7.85 (m, 2H), 7.74 (d, J = 7.4 Hz, 1H), 7.63-7.53 (m, J = 8.5 Hz, 2H), 2.87 (dt, J = 15.7, 5.8 Hz, 4H), 1.91-1.77 (m, 4H) |
| 54 | [4-acyl-1-(4-nitrophenyl)piperidine] | 470.25 | E: 1.61<br>F: 1.62 | (500 MHz, DMSO-d$_6$) δ 12.78 (s, 1H), 10.05 (s, 1H), 8.35-8.31 (m, 1H), 7.89 (td, J = 4.6, 1.8 Hz, 2H), 7.79-7.75 (m, J = 8.5 Hz, 2H), 7.75-7.68 (m, 1H), 7.55-7.47 (m, J = 8.5 Hz, 2H), 7.37-7.29 (m, 4H), 7.27-7.20 (m, 1H), 3.48 (s, 2H), 2.96-2.84 (m, 2H), 2.41-2.29 (m, 1H), 1.98 (t, J = 11.1 Hz, 2H), 1.84-1.75 (m, 2H), 1.75-1.64 (m, 2H) |
| 55 | [4-acyl-1-acetylpiperidine] | 391.2 | E: 1.06<br>F: 1.07 | (500 MHz, DMSO-d$_6$) δ 12.78 (s, 1H), 10.13 (s, 1H), 8.35-8.30 (m, 1H), 7.96-7.86 (m, 2H), 7.82-7.75 (m, J = 8.5 Hz, 2H), 7.72 (d, J = 8.5 Hz, 1H), 7.56-7.47 (m, J = 8.5 Hz, 2H), 4.42 (d, J = 13.2 Hz, 1H), 3.89 (d, J = 12.1 Hz, 1H), 3.09 (t, J = 12.0 Hz, 1H), 2.66-2.58 (m, 2H), 1.84 (t, J = 13.1 Hz, 2H), 1.69-1.57 (m, 1H), 1.53-1.39 (m, 1H) |

TABLE 2-continued

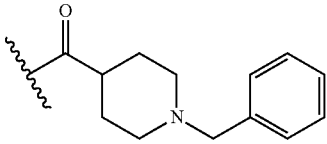 [SMILES: *C(=O)C1CCN(Cc2ccccc2)CC1]

| Example | R | LCMS (M + H)+ | HPLC Method, RT (min.) | $^1$H NMR |
|---|---|---|---|---|
| 56 | 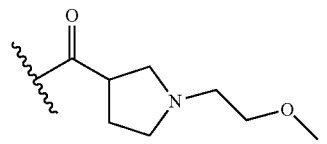 [SMILES: *C(=O)C1CCN(CCOC)C1] | 439.3 | E: 1.05<br>F: 1.15 | (500 MHz, DMSO-d$_6$) δ 12.78 (s, 1H), 10.05 (s, 1H), 8.35-8.31 (m, 1H), 7.89 (td, J = 4.6, 1.8 Hz, 2H), 7.79-7.75 (m, J = 8.5 Hz, 2H), 7.75-7.68 (m, 1H), 7.55-7.47 (m, J = 8.5 Hz, 2H), 7.37-7.29 (m, 4H), 7.27-7.20 (m, 1H), 3.48 (s, 2H), 2.96-2.84 (m, 2H), 2.41-2.29 (m, 1H), 1.98 (t, J = 11.1 Hz, 2H), 1.84-1.75 (m, 2H), 1.75-1.64 (m, 2H) |
| 57 | 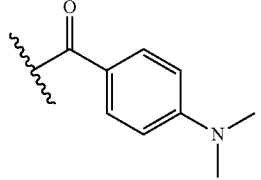 [SMILES: *C(=O)c1ccc(N(C)C)cc1] | 393.2 | E: 1.01<br>F: 0.99 | (500 MHz, DMSO-d$_6$) δ 10.14 (br. s., 1H), 8.33 (d, J = 7.4 Hz, 1H), 7.94-7.86 (m, 2H), 7.80-7.74 (m, J = 8.3 Hz, 2H), 7.72 (d, J = 7.2 Hz, 1H), 7.57-7.46 (m, J = 8.3 Hz, 2H), 3.45 (t, J = 5.5 Hz, 3H), 3.26 (s, 3H), 3.12-3.03 (m, 1H), 2.96 (br. s., 1H), 2.73 (br. s., 1H), 2.63 (br. s., 3H), 2.01 (d, J = 6.9 Hz, 2H) |
| 58 | 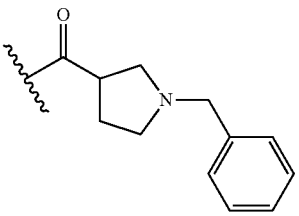 [SMILES: *C(=O)C1CCN(Cc2ccccc2)C1] | 385.3 | E: 1.38<br>F: 1.59 | (500 MHz, DMSO-d$_6$) δ 12.80 (s, 1H), 10.07 (s, 1H), 8.34 (d, J = 8.0 Hz, 1H), 7.97-7.86 (m, 6H), 7.76 (d, J = 7.7 Hz, 1H), 7.55 (d, J = 8.3 Hz, 2H), 6.78 (d, J = 8.8 Hz, 2H), 3.01 (s, 6H) |
| 59 | 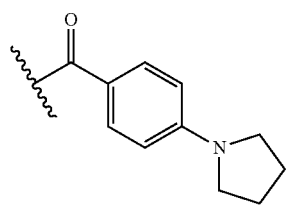 [SMILES: *C(=O)c1ccc(N2CCCC2)cc1] | 425.25 | E: 1.16<br>F: 1.26 | (500 MHz, DMSO-d$_6$) δ 12.79 (s, 1H), 10.11 (br. s., 1H), 8.39-8.29 (m, 1H), 7.93-7.86 (m, 2H), 7.79-7.73 (m, J = 8.5 Hz, 2H), 7.72-7.67 (m, 1H), 7.54-7.48 (m, J = 8.5 Hz, 2H), 7.40-7.31 (m, 4H), 7.28 (br. s., 1H), 3.67 (br. s., 2H), 3.14 (br. s., 1H), 2.96 (br. s., 1H), 2.82-2.69 (m, 2H), 2.59 (br. s., 1H), 2.07 (br. s., 2H) |
| 60 | | 411.2 | E: 1.76<br>F: 1.74 | (500 MHz, DMSO-d$_6$) δ 12.80 (s, 1H), 10.03 (s, 1H), 8.34 (d, J = 7.7 Hz, 1H), 7.97 (s, 2H), 7.93-7.86 (m, 4H), 7.77 (d, J = 7.7 Hz, 1H), 7.55 (d, J = 8.3 Hz, 2H), 6.62 (d, J = 8.5 Hz, 2H), 1.99 (br. s., 4H) |

TABLE 2-continued

| Example | R | LCMS (M + H)+ | HPLC Method, RT (min.) | ¹H NMR |
|---|---|---|---|---|
| 61 | 4-(piperidin-1-yl)benzoyl | 425.25 | E: 1.23<br>F: 1.83 | (500 MHz, DMSO-d₆) δ 10.11 (s, 1H), 8.34 (d, J = 7.7 Hz, 1H), 7.99-7.86 (m, 6H), 7.76 (d, J = 7.4 Hz, 1H), 7.56 (d, J = 8.3 Hz, 2H), 7.01 (d, J = 8.8 Hz, 2H), 3.34 (br. s., 4H), 1.60 (br. s., 6H) |
| 62 | 3-(pyrrolidin-1-yl)benzoyl | 411.2 | E: 1.55<br>F: 1.80 | ¹H NMR (500 MHz, DMSO-d₆) δ 12.81 (s, 1H), 10.31 (s, 1H), 8.38-8.32 (m, 1H), 7.97 (d, J = 8.5 Hz, 2H), 7.94-7.85 (m, 2H), 7.76 (d, J = 8.3 Hz, 1H), 7.58 (d, J = 8.5 Hz, 2H), 7.36-7.27 (m, 1H), 7.19 (d, J = 7.4 Hz, 1H), 7.07 (s, 1H), 6.75 (dd, J = 8.0, 1.7 Hz, 1H), 3.31 (br. s., 4H), 1.99 (t, J = 6.2 Hz, 4H) |
| 63 | 4-(morpholin-4-yl)benzoyl | 427.25 | E: 1.42<br>F: 1.46 | (500 MHz, DMSO-d₆) δ 12.81 (br. s., 1H), 10.18 (s, 1H), 8.34 (d, J = 7.7 Hz, 1H), 8.06-7.86 (m, 6H), 7.80-7.73 (m, 1H), 7.56 (d, J = 8.5 Hz, 2H), 7.05 (d, J = 8.8 Hz, 2H), 3.82-3.71 (m, 4H), 3.29-3.22 (m, 4H) |
| 64 | 4-(4-methylpiperazin-1-yl)benzoyl | 440.25 | E: 1.06<br>F: 1.18 | ¹H NMR (500 MHz, DMSO-d₆) δ 12.80 (s, 1H), 10.14 (s, 1H), 8.34 (d, J = 7.4 Hz, 1H), 7.96 (d, J = 8.3 Hz, 2H), 7.94-7.86 (m, 4H), 7.76 (d, J = 7.7 Hz, 1H), 7.56 (d, J = 8.0 Hz, 2H), 7.04 (d, J = 8.3 Hz, 2H), 2.46 (br. s., 4H), 2.23 (s, 3H) |
| 65 | 4-(1H-imidazol-1-yl)benzoyl | 408.2 | E: 1.05<br>F: 1.29 | ¹H NMR (500 MHz, DMSO-d₆) δ 12.83 (s, 1H), 10.55 (s, 1H), 8.38 (s, 1H), 8.35 (d, J = 8.0 Hz, 1H), 8.22 (s, 1H), 8.00-7.86 (m, 7H), 7.76 (d, J = 7.7 Hz, 1H), 7.71 (t, J = 8.0 Hz, 1H), 7.62 (d, J = 8.5 Hz, 2H), 7.17 (s, 1H) |

TABLE 2-continued

| Example | R | LCMS (M + H)+ | HPLC Method, RT (min.) | 1H NMR |
|---|---|---|---|---|
| 66 | 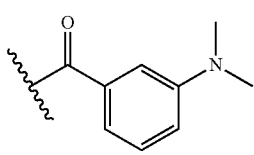 [SMILES: *C(=O)c1cccc(N(C)C)c1] | 385.1 | E: 1.16 F: 1.64 | (500 MHz, DMSO-d6) δ 12.84 (br. s., 1H), 10.35 (s, 1H), 8.40-8.31 (m, 1H), 8.00-7.86 (m, 4H), 7.76 (d, J = 7.4 Hz, 1H), 7.59 (d, J = 8.4 Hz, 2H), 7.38-7.32 (m, 1H), 7.28-7.23 (m, 2H), 6.95 (dd, J = 8.2, 2.2 Hz, 1H), 2.98 (s, 6H) |
| 67 | 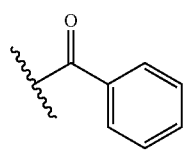 [SMILES: *C(=O)c1ccccc1] | 342.2 | E: 1.47 F: 1.47 | (500 MHz, DMSO-d6) δ 12.84 (s, 1H), 10.48 (s, 1H), 8.35 (dd, J = 7.7, 1.2 Hz, 1H), 8.04-7.96 (m, 4H), 7.95-7.88 (m, 2H), 7.80-7.73 (m, 1H), 7.65-7.52 (m, 5H) |

EXAMPLE 68

4-(4-oxo-3,4-dihydrophthalazin-1-yl)phenyl isoindoline-2-carboxylate

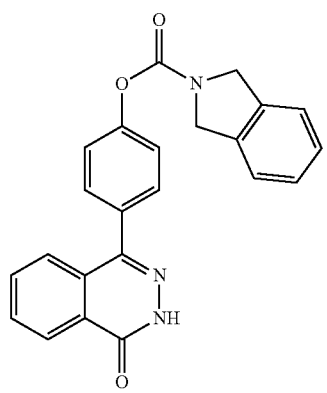 [SMILES: O=C(Oc1ccc(-c2n[nH]c(=O)c3ccccc23)cc1)N1Cc2ccccc2C1]

EXAMPLE 68A 4-bromophenyl isoindoline-2-carboxylate

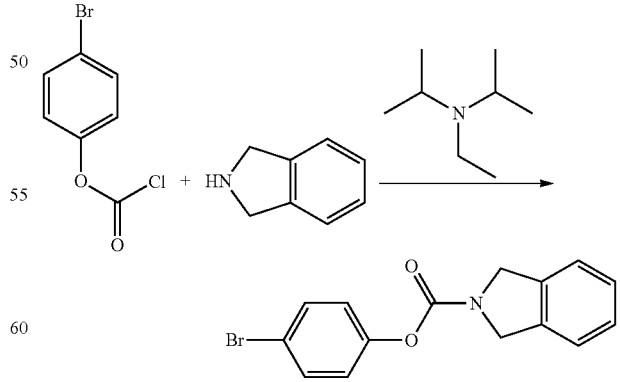

To a solution of isoindoline (167 mg, 1.401 mmol) and DIEA (0.445 mL, 2.55 mmol) in CH$_2$Cl$_2$ (3 mL), was added 4-bromophenyl carbonochloridate (300 mg, 1.274 mmol). The mixture was stirred at rt for 1h, then was quenched with water. The mixture was diluted with EtOAc (100 mL), then was washed with 1N HCl, sat Na$_2$CO$_3$ and brine, dried over Na$_2$SO$_4$, and concentrated. The crude product was purified via flash chromatography to afford 310 mg (76%) of Example 68A.

MS (ESI) m/z: 318.0 (M+H)$^+$; $^1$H NMR (500 MHz, CDCl$_3$) δ 7.53-7.48 (m, 2H), 7.36-7.29 (m, 4H), 7.13-7.07 (m, 2H), 4.94 (s, 2H), 4.84 (s, 2H)

EXAMPLE 68B (4-((isoindoline-2-carbonyl)oxy)phenyl)boronic acid

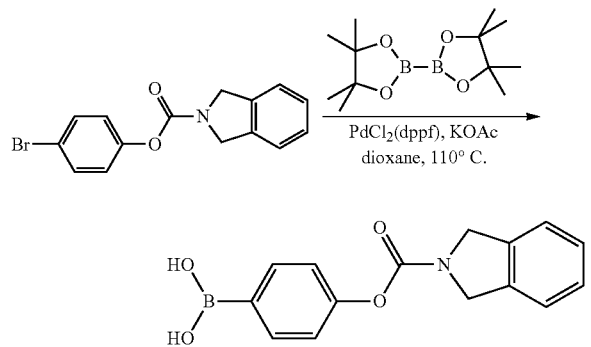

A mixture of Example 68A (100 mg, 0.314 mmol), bis(pinacolato)diboron (104 mg, 0.409 mmol), and potassium acetate (93 mg, 0.943 mmol) in dioxane (3 mL) was degassed (3× vacuum/Ar). PdCl$_2$(dppf) CH$_2$Cl$_2$ adduct (6.90 mg, 9.43 μmol) was added, then the reaction mixture was degassed again (3× vacuum/Ar), sealed in a vial and heated at 110° C. for 2 h. The reaction was concentrated and purified via preparative HPLC to afford 75 mg (84%) of Example 68B.

MS (ESI) m/z: 284.1 (M+H)$^+$; $^1$H NMR (400 MHz, CD$_3$OD) δ 7.83-7.76 (m, 1H), 7.68 (d, J=8.1 Hz, 1H), 7.40-7.28 (m, 4H), 7.24-7.10 (m, 2H), 4.95 (s, 2H), 4.78 (s, 2H).

EXAMPLE 68

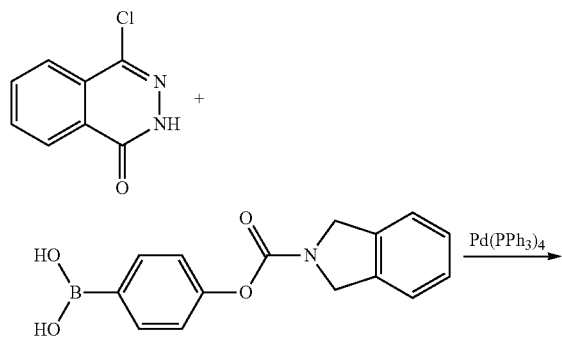

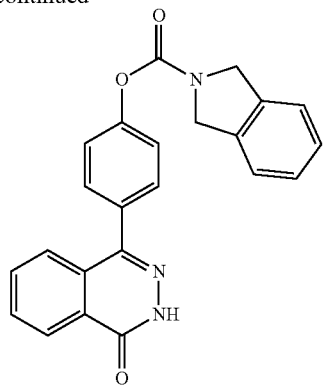

To 4-chlorophthalazin-1(2H)-one (18.24 mg, 0.101 mmol), Example 68B (26 mg, 0.092 mmol) and potassium phosphate (48.7 mg, 0.230 mmol), were added dioxane (3 mL) and water (0.5 mL). The mixture was degassed (evacuated and flushed with Ar (5×)). Pd(PPh$_3$)$_4$ (5.31 mg, 4.59 μmol) was added, then the mixture was degassed (2×). The reaction vial was sealed and heated in a microwave reactor at 150° C. for 25 min. The crude product was purified by preparative HPLC to afford 9 mg (20%) of Example 68.

MS (ESI) m/z: 384.2 (M+H)$^+$; $^1$H NMR (500 MHz, DMSO-d$_6$) δ 12.86 (s, 1H), 8.45-8.29 (m, 1H), 7.92 (qd, J=7.3, 5.8 Hz, 2H), 7.75-7.69 (m, 1H), 7.67-7.59 (m, 2H), 7.46-7.37 (m, 4H), 7.36-7.28 (m, 2H), 4.96 (s, 2H), 4.76 (s, 2H); HPLC RT=1.77 min (Method E), 1.78 min (Method F).

EXAMPLE 69

4-(4-oxo-3,4-dihydrophthalazin-1-yl)phenyl 3-phenylpyrrolidine-1-carboxylate

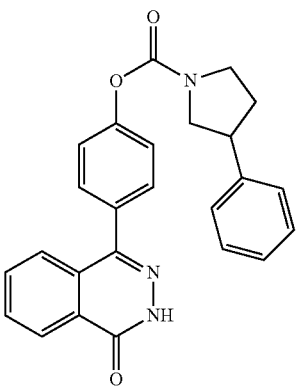 [SMILES: O=C(Oc1ccc(-c2n[nH]c(=O)c3ccccc23)cc1)N1CCC(c2ccccc2)C1]

EXAMPLE 69A 4-bromophenyl 3-phenylpyrrolidine-1-carboxylate

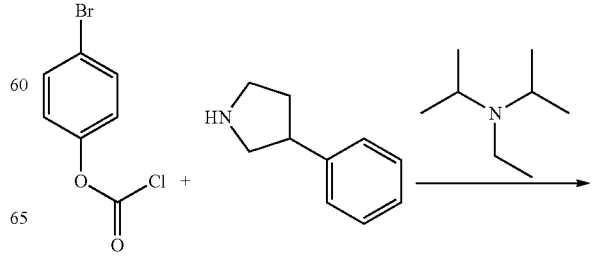

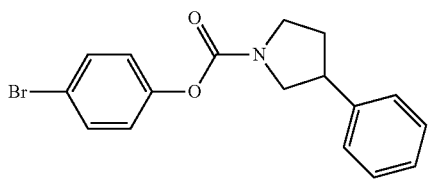

To a mixture of 3-phenylpyrrolidine (141 mg, 0.956 mmol) and DIEA (0.223 mL, 1.274 mmol) in $CH_2Cl_2$ (3 mL) at 0° C., was added 4-bromophenyl carbonochloridate (150 mg, 0.637 mmol). The mixture was stirred at rt for 1h. The reaction mixture was quenched with water and EtOAc (100 mL) was added. The organic phase was washed with 1N HCl, sat $Na_2CO_3$ and brine, dried over $Na_2SO_4$, concentrated and purified flash chromatography to afford 210 mg (95%) of Example 69A.

MS (ESI) m/z: 345.9 (M+H)+; $^1$H NMR (500 MHz, $CDCl_3$) δ 7.56-7.44 (m, 2H), 7.40-7.34 (m, 2H), 7.31-7.26 (m, 3H), 7.09-6.99 (m, 2H), 4.12-3.94 (m, 1H), 3.89-3.73 (m, 1H), 3.64 (td, J=10.2, 6.7 Hz, 1H), 3.60-3.40 (m, 3H), 2.36 (ddtd, J=18.5, 12.4, 6.3, 2.6 Hz, 1H), 2.18-2.01 (m, 1H).

EXAMPLE 69B 4-(4,4,5,5-tetramethyl-1,3,2-dioxaborolan-2-yl)phenyl 3-phenylpyrrolidine-1-carboxylate

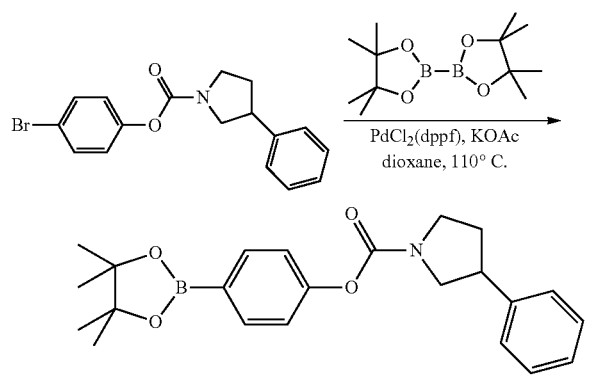

To a mixture of Example 69A (210 mg, 0.607 mmol), bis(pinacolato)diboron (185 mg, 0.728 mmol), and potassium acetate (179 mg, 1.820 mmol) in dioxane (5 mL), was added $PdCl_2$(dppf) $CH_2Cl_2$ adduct (13.31 mg, 0.018 mmol). The reaction mixture was degassed (3× vacuum/Ar), sealed in a vial and heated at 110° C. for 2 h. The reaction mixture was diluted with water and extracted with EtOAc. The organic phase was concentrated, then purified via flash chromatography (EtOAc/hexanes) to afford 220 mg (92%) of Example 69B.

MS (ESI) m/z: 394.2 (M+H)+; $^1$H NMR (500 MHz, $CDCl_3$) δ 7.86 (dd, J=7.8, 3.7 Hz, 2H), 7.42-7.35 (m, 2H), 7.33-7.26 (m, 3H), 7.22 (t, J=7.0 Hz, 2H), 4.13-3.99 (m, 1H), 3.92-3.77 (m, 1H), 3.72-3.41 (m, 3H), 2.38 (t, J=13.1 Hz, 1H), 2.19-2.07 (m, 1H), 1.37 (s, 12H).

EXAMPLE 69

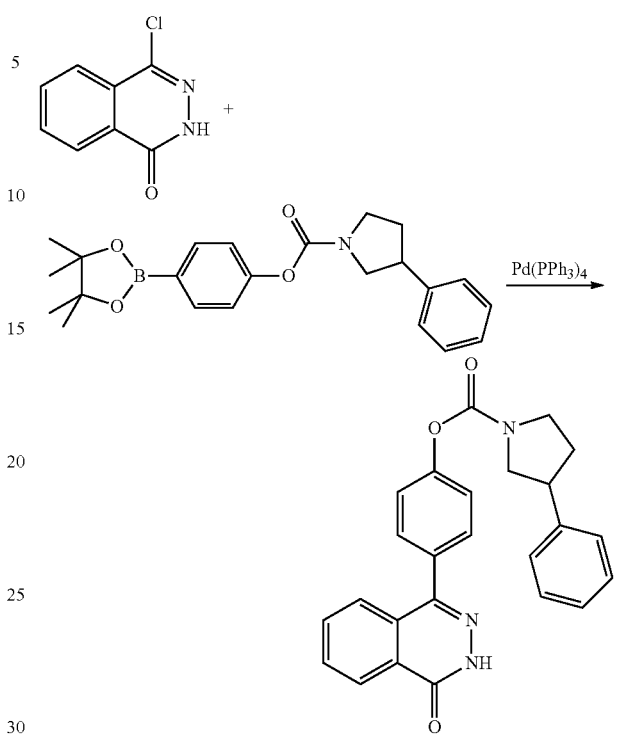

To 4-chlorophthalazin-1(2H)-one (28 mg, 0.16 mmol), Example 69B (79 mg, 0.20 mmol) and potassium phosphate (82 mg, 0.39 mmol), were added dioxane (3 mL) and water (0.33 mL). The mixture was degassed (evacuated and flushed with Ar (5×)). $Pd(PPh_3)_4$ (9.0 mg, 7.8 μmol) was added, then the mixture was degassed (2×). The reaction vial was sealed and heated in a microwave reactor at 150° C. for 35 min. The reaction mixture was concentrated, then was purified by preparative HPLC to afford 8.2 mg (10%) of the Example 69.

MS (ESI) m/z: 412.2 (M+H)+; $^1$H NMR (500 MHz, DMSO-$d_6$) δ 12.85 (s, 1H), 8.35 (d, J=7.4 Hz, 1H), 7.99-7.86 (m, 2H), 7.70 (d, J=7.4 Hz, 1H), 7.62 (dd, J=8.5, 3.9 Hz, 2H), 7.44-7.30 (m, 6H), 7.29-7.19 (m, 1H), 4.13-3.97 (m, 1H), 3.97-3.76 (m, 1H), 3.72-3.59 (m, 1H), 3.55-3.42 (m, 2H), 2.42-2.26 (m, 1H), 2.17-1.99 (m, 1H); HPLC RT=1.73 min (Method E), 1.74 min (Method F).

EXAMPLE 70

4-(4-oxo-3,4-dihydrophthalazin-1-yl)phenyl 5-methoxyisoindoline-2-carboxylate

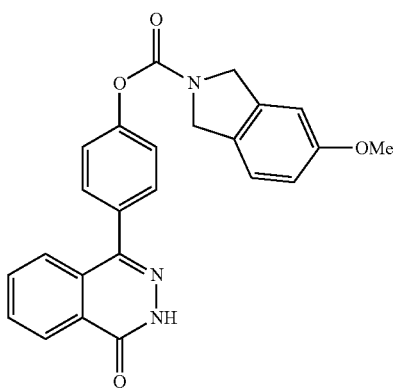 [SMILES: COc1ccc2c(c1)CN(C(=O)Oc1ccc(-c3n[nH]c(=O)c4ccccc34)cc1)C2]

EXAMPLE 70A 4-bromophenyl 5-methoxyisoindoline-2-carboxylate

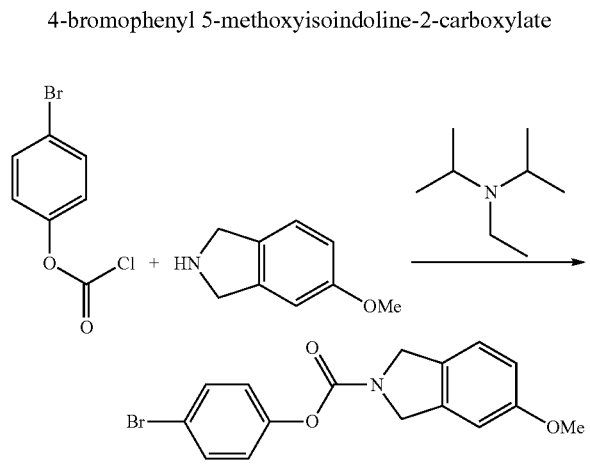

To a solution of 5-methoxyisoindoline (80 mg, 0.54 mmol) and DIEA (0.18 mL, 1.02 mmol) in $CH_2Cl_2$ (3 mL) at 0° C., was added 4-bromophenyl carbonochloridate (120 mg, 0.51 mmol). The reaction mixture was stirred rt for 1h, then was quenched with water. The mixture was diluted with EtOAc (100 mL). The organic phase was washed with 1N HCl, sat. $Na_2CO_3$ and brine, dried over $Na_2SO_4$, and concentrated. The crude product was purified via flash chromatography to afford 112 mg (63%) of Example 70A.

MS (ESI) m/z: 348.0 (M+H)+; $^1$H NMR (500 MHz, $CDCl_3$) δ 7.55-7.45 (m, 2H), 7.19 (dd, J=12.2, 8.4 Hz, 1H), 7.13-7.03 (m, 2H), 6.88 (dd, J=8.4, 2.3 Hz, 1H), 6.82 (dd, J=10.5, 1.9 Hz, 1H), 4.87 (d, J=16.2 Hz, 2H), 4.78 (d, J=17.1 Hz, 2H), 3.83 (s, 3H).

EXAMPLE 70B 4-(4,4,5,5-tetramethyl-1,3,2-dioxaborolan-2-yl)phenyl 5-methoxyisoindoline-2-carboxylate

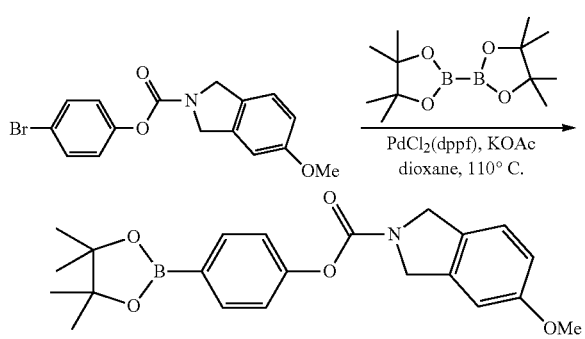

To a mixture of Example 70A (112 mg, 0.322 mmol), bis(pinacolato)diboron (98 mg, 0.39 mmol), and potassium acetate (95 mg, 0.97 mmol) in dioxane (10 mL), was added $PdCl_2$(dppf) $CH_2Cl_2$ adduct (7.1 mg, 9.7 μmol). The reaction mixture was degassed (3× vacuum/Ar), sealed in a vial and heated at 110° C. for 2 h. The reaction was diluted with water and extracted with EtOAc. The organic phase was concentrated and the residue was purified via flash chromatography to afford 100 mg (79%) of Example 70B.

MS (ESI) m/z: 396.2 (M+H)+; $^1$H NMR (500 MHz, $CDCl_3$) δ 7.85 (d, J=8.3 Hz, 2H), 7.25-7.15 (m, 3H), 6.92-6.80 (m, 2H), 4.89 (d, J=16.5 Hz, 2H), 4.79 (d, J=18.2 Hz, 2H), 3.83 (s, 3H), 1.44-1.32 (m, 12H).

EXAMPLE 70

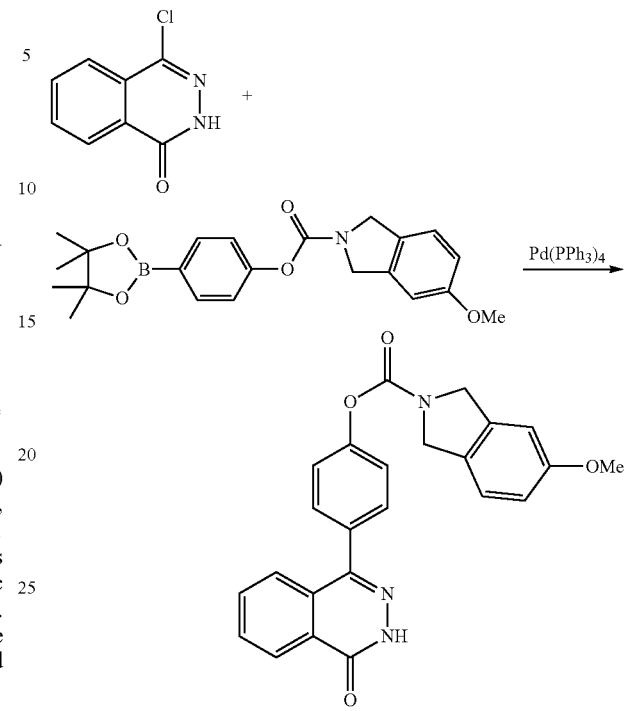

To 4-chlorophthalazin-1(2H)-one (13 mg, 0.072 mmol), Example 70B (29.9 mg, 0.076 mmol) and potassium phosphate (38.2 mg, 0.180 mmol), were added dioxane (3 mL) and water (0.33 mL). The mixture was degassed (evacuated and flushed with Ar (5×)). Pd(PPh$_3$)$_4$ (4.2 mg, 3.6 μmol) was added, then the mixture was degassed (2×). The reaction vial was sealed and heated in a microwave reactor at 150° C. for 25 min. The reaction mixture was concentrated, then was purified via preparative HPLC to afford 9 mg (23%) of Example 70.

MS (ESI) m/z: 414.1 (M+H)+; $^1$H NMR (500 MHz, DMSO-d$_6$) δ 12.86 (s, 1H), 8.35 (dd, J=7.6, 1.2 Hz, 1H), 7.98-7.88 (m, 2H), 7.76-7.70 (m, 1H), 7.68-7.61 (m, J=8.5 Hz, 2H), 7.43-7.36 (m, J=8.5 Hz, 2H), 7.30 (d, J=8.3 Hz, 1H), 6.99 (br. s., 1H), 6.91 (d, J=8.3 Hz, 1H), 4.92 (s, 1H), 4.87 (s, 1H), 4.72 (s, 1H), 4.68 (s, 1H), 3.81-3.72 (m, 3H); HPLC RT=9.48 min (Method A), 8.98 min (Method B).

EXAMPLE 71

4-(4-oxo-3,4-dihydrophthalazin-1-yl)phenyl 5-fluoroisoindoline-2-carboxylate

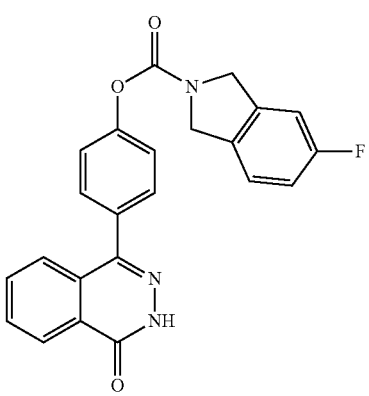 [SMILES: O=C(Oc1ccc(-c2n[nH]c(=O)c3ccccc23)cc1)N1Cc2ccc(F)cc2C1]

EXAMPLE 71A 4-bromophenyl 5-fluoroisoindoline-2-carboxylate

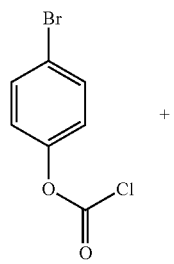

To a mixture of 5-fluoroisoindoline (141 mg, 1.03 mmol) and DIEA (0.326 mL, 1.87 mmol) in CH$_2$Cl$_2$ (3 mL) at 0° C., was added 4-bromophenyl carbonochloridate (220 mg, 0.934 mmol). The mixture was stirred at rt for 1h, then was quenched with water. The mixture was diluted with EtOAc (100 mL), then was washed with 1N HCl, sat Na$_2$CO$_3$ and brine, dried over Na$_2$SO$_4$, and concentrated. The crude product was purified via flash chromatography (EtOAc/hexanes) to afford 190 mg (61%) of Example 71A.

MS (ESI) m/z: 414.1 (M+H)$^+$; $^1$H NMR (500 MHz, CDCl$_3$) δ 7.56-7.46 (m, 2H), 7.34-7.21 (m, 1H), 7.16-7.07 (m, 2H), 7.05-6.97 (m, 2H), 4.92 (d, J=14.0 Hz, 2H), 4.82 (d, J=14.0 Hz, 2H).

EXAMPLE 71B 4-(4,4,5,5-tetramethyl-1,3,2-dioxaborolan-2-yl)phenyl 5-fluoroisoindoline-2-carboxylate

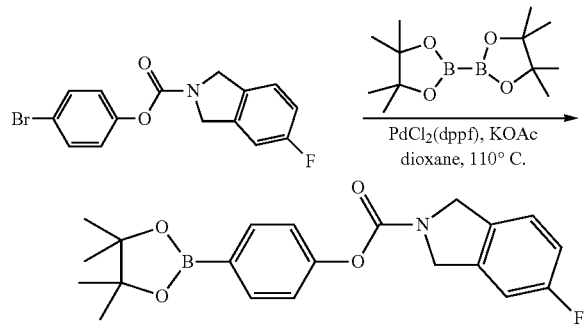

To a mixture of Example 71A (182 mg, 0.541 mmol), bis(pinacolato)diboron (165 mg, 0.65 mmol), and potassium acetate (159 mg, 1.62 mmol) in dioxane (4 mL), was added PdCl$_2$(dppf) CH$_2$Cl$_2$ adduct (11.9 mg, 0.016 mmol). The reaction mixture was degassed (3× vacuum/Ar), sealed in a vial and heated at 110° C. for 2 h. The reaction mixture was partitioned between EtOAc and H$_2$O. The organic phase was concentrated and the residue was purified via flash chromatography to afford 150 mg (72%) of Example 71B.

MS (ESI) m/z: 384.2 (M+H)$^+$; $^1$H NMR (500 MHz, CDCl$_3$) δ 7.88-7.83 (m, 2H), 7.28-7.19 (m, 3H), 7.09-6.95 (m, 2H), 4.93 (d, J=14.3 Hz, 2H), 4.82 (d, J=14.0 Hz, 2H), 1.43-1.34 (m, 12H).

EXAMPLE 71

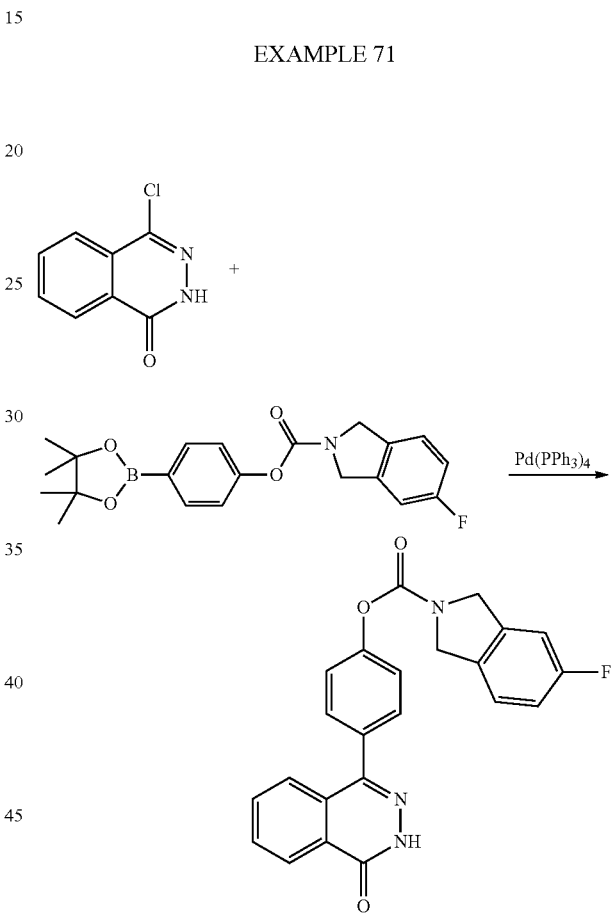

To 4-chlorophthalazin-1(2H)-one (20 mg, 0.11 mmol), Example 71B (44.6 mg, 0.116 mmol) and potassium phosphate (58.8 mg, 0.277 mmol), were added dioxane (3 mL) and water (0.33 mL). The mixture was degassed (evacuated and flushed with Ar (5×)). Pd(PPh$_3$)$_4$ (6.4 mg, 5.5 µmol) was added, then the mixture was degassed (2×). The reaction vial was sealed and heated in a microwave reactor at 150° C. for 25 min. The reaction mixture was concentrated and the residue purified via preparative HPLC to afford 5 mg (8%) of Example 71.

MS (ESI) m/z: 402.1 (M+H)$^+$; $^1$H NMR (500 MHz, DMSO-d$_6$) δ 12.86 (s, 1H), 8.39-8.32 (m, 1H), 7.95-7.89 (m, 2H), 7.75-7.69 (m, 1H), 7.66-7.60 (m, 2H), 7.44-7.35 (m, 4H), 7.29-7.15 (m, 4H), 4.94 (d, J=17.3 Hz, 2H), 4.74 (d, J=17.1 Hz, 2H); HPLC RT=9.62 min (Method A), 9.15 min (Method B).

EXAMPLE 72

4-(4-oxo-3,4-dihydrophthalazin-1-yl)phenyl 5-((4-methylpiperazin-1-yl)methyl)isoindoline-2-carboxylate, 2 TFA

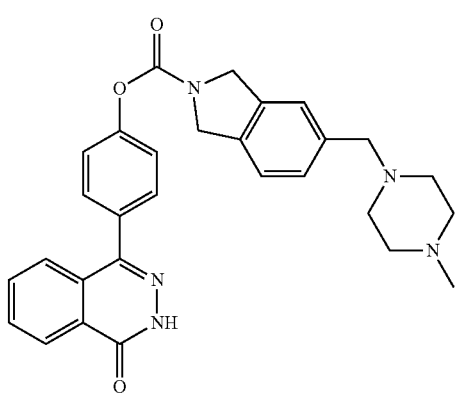 [SMILES: CN1CCN(Cc2ccc3c(c2)CN(C(=O)Oc2ccc(-c4n[nH]c(=O)c5ccccc45)cc2)C3)CC1]

EXAMPLE 72A 4-bromophenyl 5-((4-methylpiperazin-1-yl)methyl)isoindoline-2-carboxylate, 2 TFA

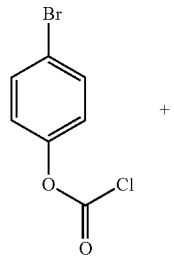

+

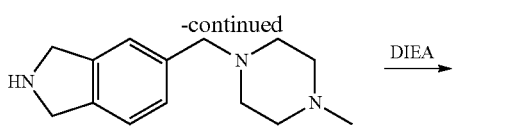

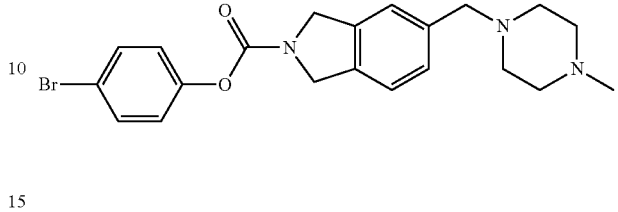

To a solution of Intermediate 2 (196 mg, 0.849 mmol) and DIEA (0.297 mL, 1.70 mmol) in CH$_2$Cl$_2$ (3 mL) at 0° C., was added 4-bromophenyl carbonochloridate (200 mg, 0.849 mmol). The mixture was stirred at rt for 1h. The reaction mixture was quenched with water and diluted with EtOAc (100 mL). The organic phase was washed with 1N HCl, sat Na$_2$CO$_3$ and brine, dried over Na$_2$SO$_4$ and concentrated. The crude product was purified by flash chromatography, followed by preparative HPLC to afford 280 mg (50%) of Example 72A.

MS (ESI) m/z: 430.1 (M+H)$^+$; $^1$H NMR (500 MHz, CD$_3$OD) δ 7.60-7.51 (m, 2H), 7.49-7.38 (m, 3H), 7.21-7.10 (m, 2H), 4.96 (s, 2H), 4.79 (s, 2H), 4.15 (s, 2H), 3.49 (br. s., 4H), 3.30-3.19 (m, 4H), 2.94 (s, 3H).

EXAMPLE 72B 4-(4,4,5,5-tetramethyl-1,3,2-dioxaborolan-2-yl)phenyl 5-((4-methylpiperazin-1-yl)methyl)isoindoline-2-carboxylate

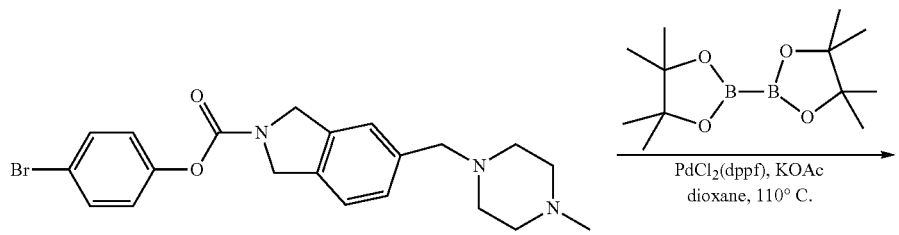

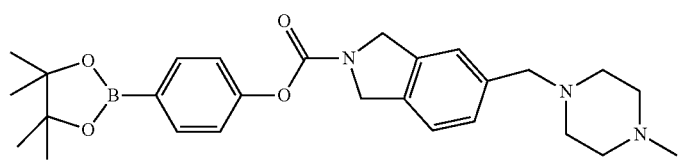

To a mixture of Example 72A (70 mg, 0.106 mmol), bis(pinacolato)diboron (32.4 mg, 0.128 mmol), and potassium acetate (31.3 mg, 0.319 mmol) in dioxane (10 mL), was added PdCl$_2$(dppf) CH$_2$Cl$_2$ adduct (2.3 mg, 3.2 μmol). The reaction mixture was degassed (3× vacuum/Ar), sealed in a vial and heated at 110° C. for 2 h. The reaction was quenched with water, then extracted with EtOAc. The organic phase was concentrated to afford 80 mg of Example 72B, which was used as is in the following step without further purification.

MS (ESI) m/z: 478.4 (M+H)$^+$

EXAMPLE 72

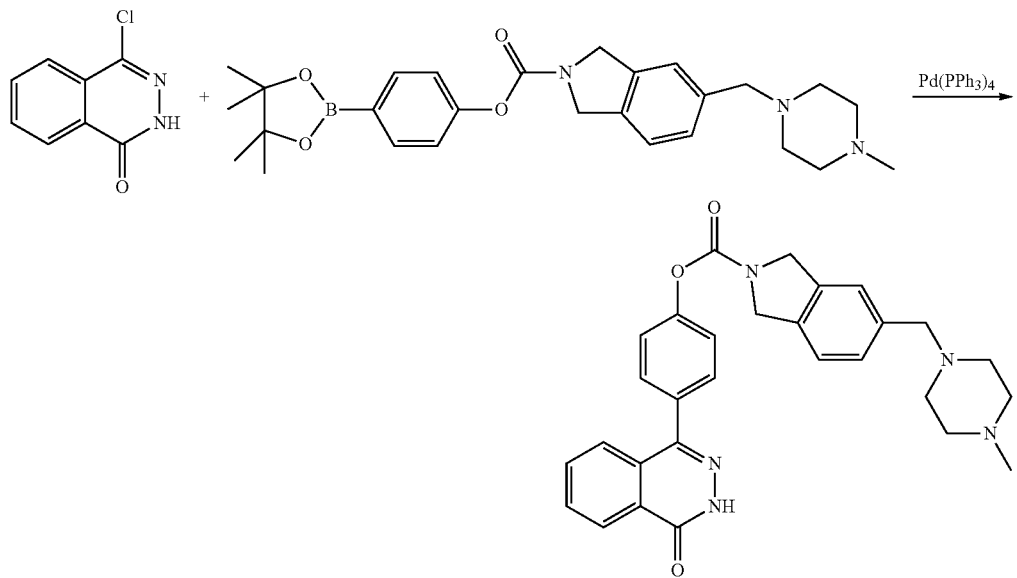

To a vial containing 4-chlorophthalazin-1(2H)-one (22 mg, 0.12 mmol), Example 72B (80 mg, 0.106 mmol) and potassium phosphate (64.6 mg, 0.305 mmol), were added dioxane (3 mL) and water (0.33 mL). The mixture was degassed (evacuated and flushed with Ar (5×)). Pd(PPh$_3$)$_4$ (7.0 mg, 6.1 μmol) was added, then the mixture was degassed (2×). The reaction vial was sealed and heated in a microwave reactor at 150° C. for 25 min. The reaction mixture was concentrated and purified via preparative HPLC to afford 22 mg (25%) of Example 72.

MS (ESI) m/z: 496.2 (M+H)$^+$; $^1$H NMR (500 MHz, DMSO-d$_6$) δ 12.86 (s, 1H), 8.43-8.31 (m, 1H), 8.02-7.86 (m, 2H), 7.71 (d, J=7.7 Hz, 1H), 7.65 (d, J=8.8 Hz, 2H), 7.47-7.34 (m, 4H), 7.30 (d, J=7.4 Hz, 1H), 4.95 (s, 2H), 4.76 (br. s., 2H), 3.65 (br. s., 2H), 2.99 (br. s., 4H), 2.77 (br. s., 3H), 2.36 (br. s., 2H); HPLC RT=4.32 min (Method A), 5.17 min (Method B).

EXAMPLE 73

4-(4-((5-phenyloxazol-2-yl)amino)phenyl)phthalazin-1(2H)-one

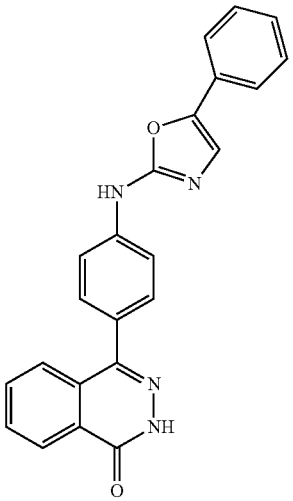 [SMILES: O=c1[nH]nc(-c2ccc(Nc3ncc(-c4ccccc4)o3)cc2)c2ccccc12]

EXAMPLE 73A

N-(4-bromophenyl)-5-phenyloxazol-2-amine

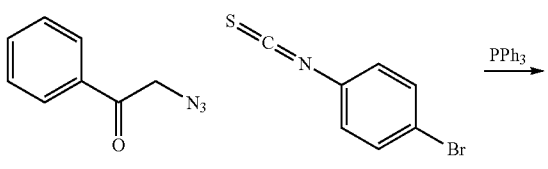

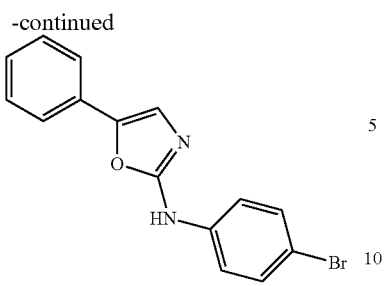

To a solution of 2-azido-1-phenylethanone (*Angew. Chem. Int. Ed.* 2007, 46, 4489-4491) (126 mg, 0.782 mmol) and 1-bromo-4-isothiocyanatobenzene (167 mg, 0.782 mmol) in dioxane (4 mL) at 80° C., was added triphenylphosphine (205 mg, 0.782 mmol). The mixture was stirred at 85° C. for 30 min, then was cooled to rt. The reaction mixture was concentrated. The solid was recrystallized from hot $CH_3Cl$ (~5 mL). The precipitate was suspended in EtOAc (~3 mL), filtered and collected to afford 134 mg (54%) of Example 73A as a white solid.

MS (ESI) m/z: 315.0 $(M+H)^+$; $^1H$ NMR (400 MHz, $CD_3OD$) δ 7.62-7.57 (m, 2H), 7.51-7.46 (m, 2H), 7.46-7.41 (m, 2H), 7.39 (t, J=7.7 Hz, 2H), 7.26 (dt, J=7.4, 1.3 Hz, 1H), 7.24 (s, 1H).

EXAMPLE 73B 5-phenyl-N-(4-(4,4,5,5-tetramethyl-1,3,2-dioxaborolan-2-yl)phenyl)oxazol-2-amine

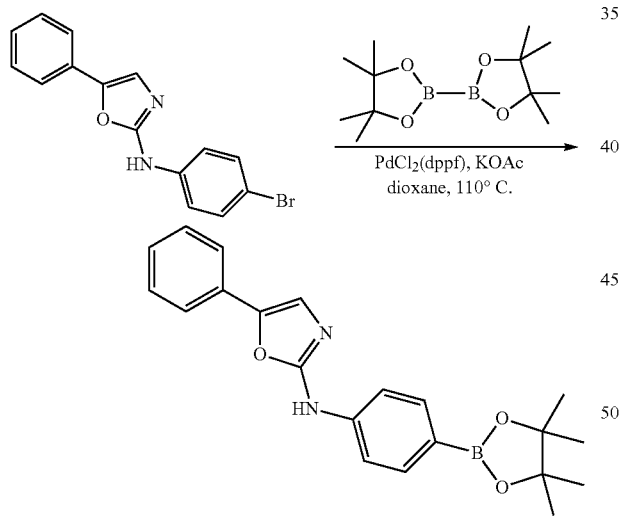

To a vial containing Example 73A (136 mg, 0.432 mmol), bis(pinacolato)diboron (164 mg, 0.647 mmol) and potassium acetate (127 mg, 1.30 mmol), was added dioxane (2 mL). The mixture was degassed (evacuated and flushed with Ar (3×)). $PdCl_2(dppf)$-$CH_2Cl_2$ adduct (17.6 mg, 0.022 mmol) was added, then the mixture was degassed (2×), then was sealed. The mixture was stirred at 110° C. for 2 h. The reaction mixture was diluted with EtOAc. The organic phase was washed with $H_2O$ and brine, dried ($Na_2SO_4$) and concentrated. The crude product was purified by flash chromatography (gradient from 0 to 50% ethyl acetate/hexanes) to afford 122 mg (78%) of Example 73B as a white solid.

MS (ESI) m/z: 363.1 $(M+H)^+$; $^1H$ NMR (400 MHz, $CDCl_3$) δ 7.81 (d, J=8.8 Hz, 2H), 7.55 (dd, J=8.3, 1.2 Hz, 2H), 7.49 (d, J=8.8 Hz, 2H), 7.43 (s, 1H), 7.42-7.36 (m, 2H), 7.29-7.23 (m, 1H), 7.18 (s, 1H), 1.35 (s, 12H)

EXAMPLE 73

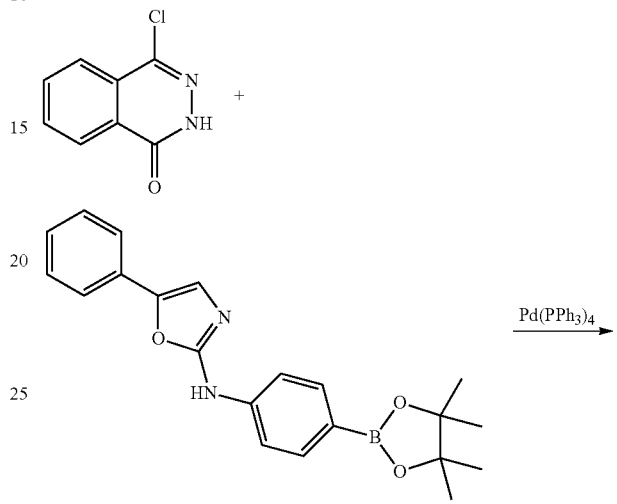

To 4-chlorophthalazin-1(2H)-one (36.7 mg, 0.203 mmol), Example 73B (67 mg, 0.185 mmol) and potassium phosphate (98 mg, 0.46 mmol) in dioxane (3 mL) and water (0.5 mL), was added $Pd(PPh_3)_4$ (10.7 mg, 9.25 μmol). The mixture was degassed (3×), then the reaction vial was sealed and heated in a microwave reactor at 150° C. for 25 min. The crude product was purified by preparative HPLC to afford 9.7 mg (11%) of Example 73.

MS (ESI) m/z: 381.1 $(M+H)^+$; $^1H$ NMR (500 MHz, DMSO-$d_6$) δ 12.78 (s, 1H), 10.60 (s, 1H), 8.40-8.30 (m, 1H), 7.96-7.87 (m, 2H), 7.84-7.73 (m, 3H), 7.62 (d, J=7.7 Hz, 2H), 7.57 (d, J=8.5 Hz, 2H), 7.51 (s, 1H), 7.45 (t, J=7.7 Hz, 2H), 7.33-7.24 (m, 1H); HPLC RT=8.99 min (Method A), 8.46 min (Method B).

EXAMPLE 74

4-(4-((4-phenylthiazol-2-yl)amino)phenyl)phthalazin-1(2H)-one

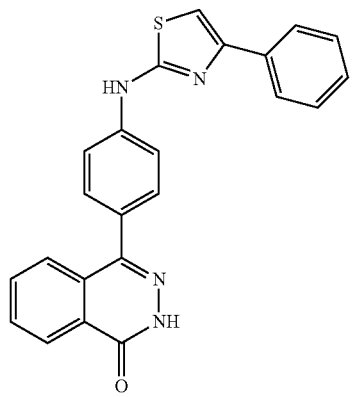 [SMILES: O=c1[nH]nc(-c2ccc(Nc3nc(-c4ccccc4)cs3)cc2)c2ccccc12]

EXAMPLE 74A

N-(4-bromophenyl)-4-phenylthiazol-2-amine

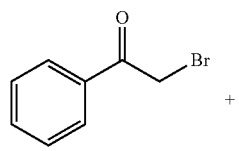

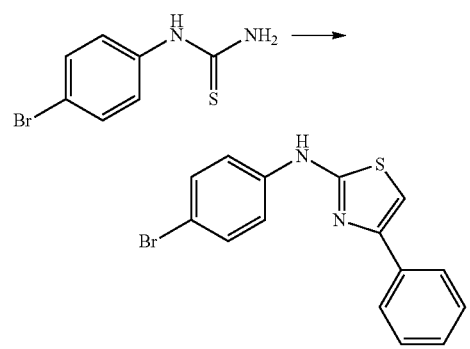

2-bromo-1-phenylethanone (105 mg, 0.528 mmol) and 1-(4-bromophenyl)thiourea (122 mg, 0.528 mmol) were mixed in glycerol (5 mL) and stirred at 90° C. for 2 h. The reaction mixture was partitioned between EtOAc and water. The organic phase was concentrated and purified via flash chromatography (EtOAc/hexanes) to afford 165 mg (94%) of Example 74A.

MS (ESI) m/z: 331.0 (M+H)$^+$; $^1$H NMR (500 MHz, CDCl$_3$) δ 7.87-7.82 (m, 2H), 7.44-7.38 (m, 4H), 7.36-7.31 (m, 1H), 7.29-7.22 (m, 2H), 6.84 (s, 1H)

EXAMPLE 74B 4-phenyl-N-(4-(4,4,5,5-tetramethyl-1,3,2-dioxaborolan-2-yl)phenyl)thiazol-2-amine

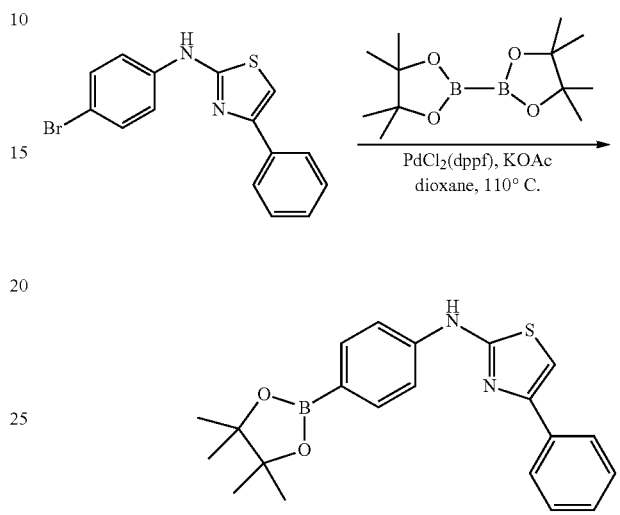

To a mixture of Example 74A (160 mg, 0.483 mmol), bis(pinacolato)diboron (147 mg, 0.580 mmol), and potassium acetate (142 mg, 1.45 mmol) in dioxane (10 mL), was added PdCl$_2$(dppf) CH$_2$Cl$_2$ adduct (10.6 mg, 0.014 mmol). The reaction mixture was degassed (3× vacuum/Ar), sealed in a vial and heated at 110° C. for 2 h. The reaction was diluted with water and extracted with EtOAc. The organic phase was concentrated and the product purified via flash chromatography to afford 130 mg (71%) of Example 74B.

MS (ESI) m/z: 379.0 (M+H)$^+$.

EXAMPLE 74

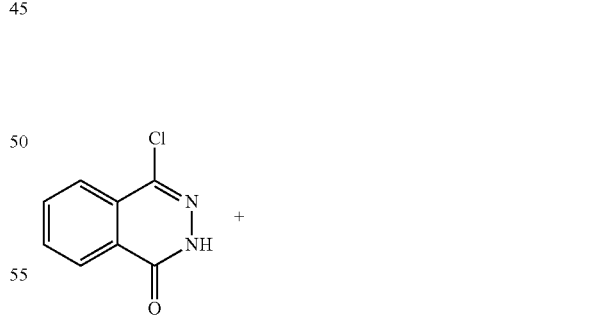

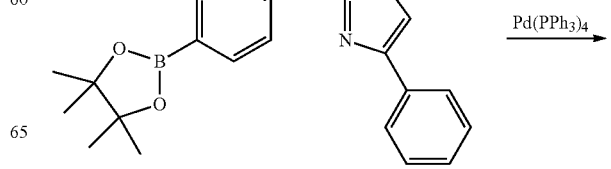

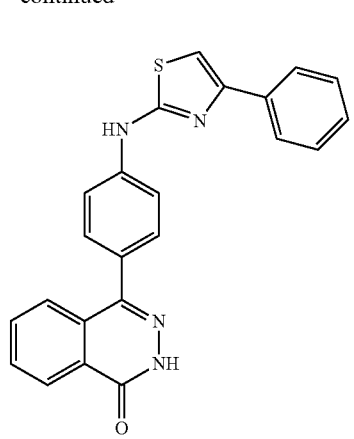

To 4-chlorophthalazin-1(2H)-one (18 mg, 0.10 mmol), Example 74B (45.2 mg, 0.120 mmol) and potassium phosphate (53 mg, 0.25 mmol), were added dioxane (3 mL) and water (0.33 mL). The mixture was degassed (evacuated and flushed with Ar (5×)). Pd(PPh$_3$)$_4$ (5.8 mg, 5.0 μmol) was added, then the mixture was degassed (2×). The reaction vial was sealed and heated in a microwave reactor at 150° C. for 35 min. The reaction mixture was concentrated, then was purified by preparative HPLC to afford 2.0 mg (3.9%) of Example 74.

MS (ESI) m/z: 397.0 (M+H)$^+$; $^1$H NMR (500 MHz, DMSO-d$_6$) δ 12.78 (s, 1H), 10.53 (s, 1H), 8.39-8.31 (m, 1H), 8.01-7.86 (m, 6H), 7.81 (d, J=7.4 Hz, 1H), 7.59 (d, J=8.5 Hz, 2H), 7.48-7.38 (m, 3H), 7.37-7.30 (m, 1H); HPLC RT=1.85 min (Method E), 1.90 min (Method F).

EXAMPLE 75

4-(4-(benzo[d]oxazol-2-ylamino)phenyl)phthalazin-1(2H)-one

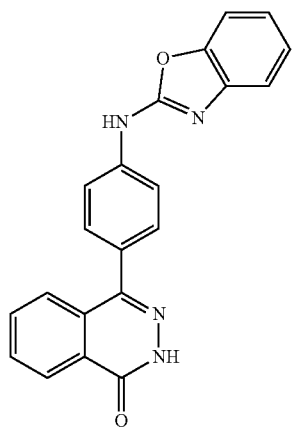

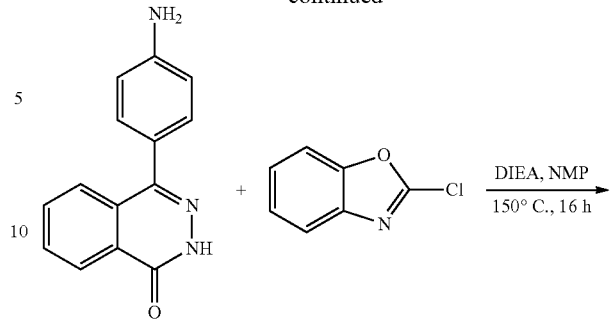

Intermediate 3 (35 mg, 0.100 mmol), 2-chlorobenzo[d]oxazole (0.015 mL, 0.130 mmol), and DIEA (0.087 mL, 0.498 mmol) were dissolved in NMP (1 mL) and the reaction mixture was heated in a capped vial at 150° C. for 18 h. The reaction mixture was purified by preparative HPLC to afford 5.0 mg (14%) of Example 75.

MS (ESI) m/z: 355.05 (M+H)$^+$; $^1$H NMR (500 MHz, DMSO-d$_6$) δ 12.83 (s, 1H), 10.90 (br. s., 1H), 8.39-8.30 (m, 1H), 7.94 (d, J=8.4 Hz, 2H), 7.93-7.87 (m, 2H), 7.80-7.76 (m, 1H), 7.63 (d, J=8.4 Hz, 2H), 7.51 (dd, J=16.6, 7.7 Hz, 2H), 7.28-7.22 (m, 1H), 7.19-7.14 (m, 1H); HPLC RT=1.58 min (Method E), 1.64 min (Method F).

EXAMPLE 76

N-(4-(4-oxo-3,4-dihydrophthalazin-1-yl)phenyl)indoline-1-carboxamide

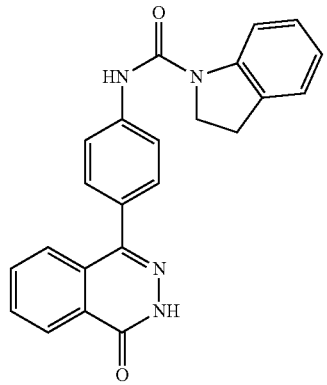

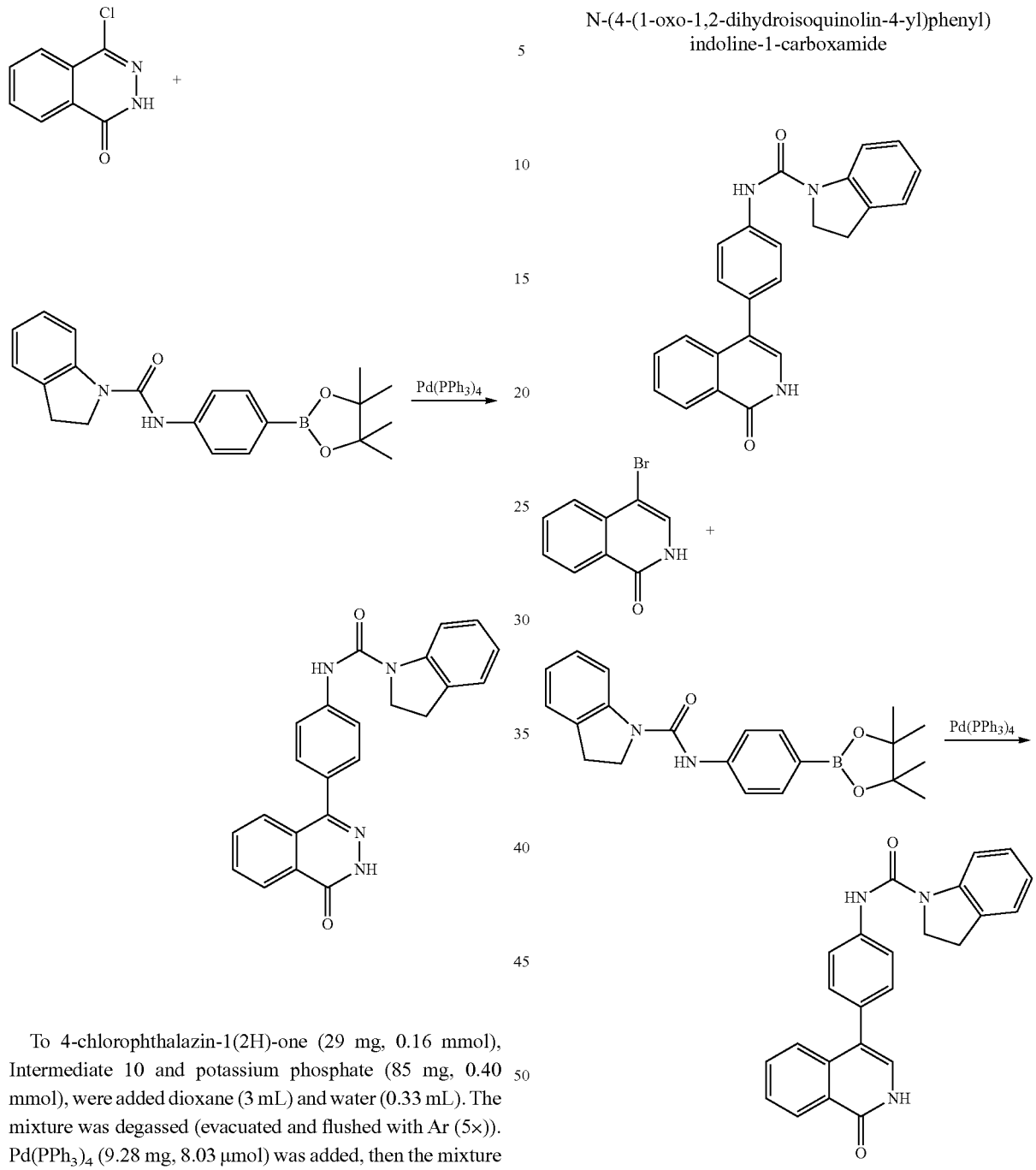

EXAMPLE 77

N-(4-(1-oxo-1,2-dihydroisoquinolin-4-yl)phenyl)indoline-1-carboxamide

To 4-chlorophthalazin-1(2H)-one (29 mg, 0.16 mmol), Intermediate 10 and potassium phosphate (85 mg, 0.40 mmol), were added dioxane (3 mL) and water (0.33 mL). The mixture was degassed (evacuated and flushed with Ar (5×)). Pd(PPh$_3$)$_4$ (9.28 mg, 8.03 μmol) was added, then the mixture was degassed (2×). The reaction vial was sealed and heated in a microwave reactor at 150° C. for 30 min. The reaction mixture was concentrated and purified via preparative HPLC to afford 6.1 mg (9.4%) of Example 76.

MS (ESI) m/z: 383.1 (M+H)$^+$; $^1$H NMR (500 MHz, DMSO-d$_6$) δ 12.81 (s, 1H), 8.74 (s, 1H), 8.34 (dd, J=7.7, 1.2 Hz, 1H), 8.00-7.85 (m, 3H), 7.76 (d, J=8.9 Hz, 3H), 7.53 (d, J=8.4 Hz, 2H), 7.22 (d, J=7.4 Hz, 1H), 7.14 (t, J=7.7 Hz, 1H), 6.92 (t, J=7.4 Hz, 1H), 4.18 (t, J=8.7 Hz, 2H), 3.20 (t, J=8.7 Hz, 2H); HPLC RT=1.65 min (Method E), 1.66 min (Method F).

According to the procedure for the preparation of Example 76, coupling of Intermediate 6 (28 mg, 0.125 mmol) and Intermediate 10 (54.6 mg, 0.150 mmol) afforded 7.5 mg (16%) of Example 77.

MS (ESI) m/z: 382.1 (M+H)$^+$; $^1$H NMR (500 MHz, DMSO-d$_6$) δ 11.41 (br. s., 1H), 8.63 (s, 1H), 8.30 (d, J=8.0 Hz, 1H), 7.89 (d, J=8.3 Hz, 1H), 7.75-7.66 (m, 3H), 7.59-7.51 (m, 2H), 7.35 (d, J=8.3 Hz, 2H), 7.21 (d, J=7.4 Hz, 1H), 7.13 (t, J=7.7 Hz, 1H), 7.07 (s, 1H), 6.91 (t, J=7.3 Hz, 1H), 4.17 (t, J=8.5 Hz, 2H), 3.20 (t, J=8.3 Hz, 2H); HPLC RT=1.77 min (Method E), 1.73 min (Method F).

What is claimed is:

1. A compound of Formula (I):

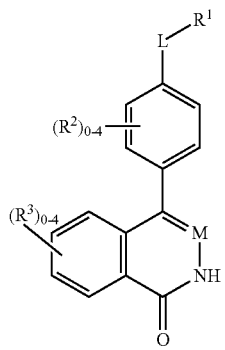

or a stereoisomer, a tautomer, or a pharmaceutically acceptable salt thereof, wherein:

M is N;

L is selected from —CR$^4$R$^4$C(O)—, —OC(O)—, and —NR$^6$—;

R$^1$ is selected from OC$_{1-4}$ alkyl, NR$^5$R$^5$, C$_{3-10}$ carbocycle and 4- to 12-membered heterocycle comprising carbon atoms and 1-4 heteroatoms selected from N, NR$^8$, O, and S(O)$_p$;

wherein said alkyl, carbocycle, and heterocycle are substituted with 1-4 R$^7$;

R$^2$, at each occurrence, is independently selected from halogen, C$_{1-6}$ alkyl, C$_{1-4}$ alkoxy, C$_{1-4}$ alkylthio, C$_{1-4}$ haloalkyl, —OH, —CH$_2$OH, —OCH$_2$F, —OCHF$_2$, —OCF$_3$, CN, —NH$_2$, —NH(C$_{1-4}$ alkyl), —N(C$_{1-4}$ alkyl)$_2$, —CO$_2$H, —CH$_2$CO$_2$H, —CO$_2$(C$_{1-4}$ alkyl), —CO(C$_{1-4}$ alkyl), —CH$_2$NH$_2$, —CONH$_2$, —CONH(C$_{1-4}$ alkyl), —CON(C$_{1-4}$ alkyl)$_2$, —OCH$_2$CO$_2$H, —NHCO(C$_{1-4}$ alkyl), —NHCO$_2$(C$_{1-4}$ alkyl), —NHSO$_2$(C$_{1-4}$ alkyl), —SO$_2$NH$_2$, —C(=NH)NH$_2$, carbocycle, and heterocycle, wherein said alkyl, alkoxy, alkylthio, haloalkyl, carbocycle, and heterocycle are substituted with 0-4 R$^9$;

R$^3$, at each occurrence, is independently selected from halogen, C$_{1-6}$ alkyl, C$_{1-4}$ alkoxy, C$_{1-4}$ alkylthio, C$_{1-4}$ haloalkyl, —CH$_2$OH, —OCH$_2$F, —OCHF$_2$, —OCF$_3$, CN, —NH$_2$, —NH(C$_{1-4}$ alkyl), —N(C$_{1-4}$ alkyl)$_2$, —CO$_2$H, —CH$_2$CO$_2$H, —CO$_2$(C$_{1-4}$ alkyl), —CO(C$_{1-4}$ alkyl), —CH$_2$NH$_2$, —CONH$_2$, —CONH(C$_{1-4}$ alkyl), —CON(C$_{1-4}$ alkyl)$_2$, —OCH$_2$CO$_2$H, —NHCO(C$_{1-4}$ alkyl), —NHCO$_2$(C$_{1-4}$ alkyl), —NHSO$_2$(C$_{1-4}$ alkyl), —SO$_2$NH$_2$, —C(=NH)NH$_2$, carbocycle, and heterocycle, wherein said alkyl, alkoxy, alkylthio, haloalkyl, carbocycle, and heterocycle are substituted with 0-4 R$^9$;

R$^4$, at each occurrence, is independently selected from H, halogen, OH, NH$_2$, CH$_2$NH$_2$, C$_{1-4}$ haloalkyl, OCH$_2$F, OCHF$_2$, OCF$_3$, —NH(C$_{1-4}$ alkyl), —N(C$_{1-4}$ alkyl)$_2$, C$_{1-4}$ alkoxy, CH$_2$OH, CH$_2$O(C$_{1-4}$ alkyl), CH$_2$CO$_2$H, CH$_2$CO$_2$(C$_{1-4}$ alkyl), C$_{1-4}$ alkyl, carbocycle, and heterocycle, wherein said alkyl, alkoxy, haloalkyl, carbocycle, and heterocycle are substituted with 0-4 R$^9$;

R$^5$, at each occurrence, is independently selected from H, C$_{1-4}$ alkyl, —(CR$^6$R$^6$)$_n$—C$_{3-10}$ carbocycle and —(CR$^6$R$^6$)$_n$-4-10 membered heterocycle comprising carbon atoms and 1-4 heteroatoms selected from N, NR$^8$, O, and S(O)$_p$, wherein said alkyl, carbocycle and heterocycle are substituted with 1-4 R$^7$;

alternatively, R$^5$ and R$^5$ are taken together with the nitrogen atom to which they are attached to form 4- to 10-membered heterocycle substituted with 1-4 R$^7$;

R$^6$, at each occurrence, is independently selected from H and C$_{1-4}$ alkyl;

R$^7$, at each occurrence, is independently selected from H, =O, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NH-COCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NH$_2$, —NHC(O)NH(C$_{1-4}$ alkyl), —NHC(O)N(C$_{1-4}$ alkyl)$_2$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —CONH$_2$, —CONH(C$_{1-4}$ alkyl), —CON(C$_{1-4}$ alkyl)$_2$, —CH$_2$CONH$_2$, —(CH$_2$)$_n$-carbocycle, —O(CH$_2$)$_n$-carbocycle, —O(CH$_2$)$_n$-heterocycle, and —(CH$_2$)$_n$-heterocycle comprising carbon atoms and 1-4 heteroatoms selected from N, NR$^8$, O, and S(O)$_p$, wherein said alkyl, alkoxyl, carbocycle, and heterocycle are substituted with 0-4 R$^9$;

R$^8$, at each occurrence, is independently selected from H, C$_{1-4}$ alkyl, C(O)C$_{1-4}$alkyl, C(O)carbocycle, C(O)heterocycle, C(O)NR$^5$R$^5$, C(O)O-alkyl, C(O)O-carbocycle, C(O)O-heterocycle, SO$_2$alkyl, SO$_2$carbocycle, SO$_2$heterocycle, SO$_2$NR$^5$R$^5$, —(CH$_2$)$_n$-carbocycle, and —(CH$_2$)$_n$-heterocycle, wherein said alkyl, carbocycle, and heterocycle are substituted with 0-4 R$^9$;

alternatively, R$^8$ and R$^8$ are taken together with the nitrogen atom to which they are attached to form a 4- to 10-membered heterocycle substituted with 0-4 R$^9$;

R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —O(CH$_2$)$_n$heterocycle, —O(CH$_2$)$_{(2-4)}$NR$^a$R$^a$, —(CR$^{10}$R$^{10}$)$_n$-4-10 membered heterocycle, wherein said alkyl, alkoxyl, carbocycle, and heterocycle are substituted with 0-4 R$^b$;

R$^{10}$ is selected from H and C$_{1-4}$ alkyl;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form 4- to 10-membered heterocycle, wherein said alkyl, alkylene, and heterocycle are substituted with 0-4 R$^b$;

R$^b$, at each occurrence, is independently selected from =O, halo, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N(C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

$R^d$, at each occurrence, is independently selected from =O, halo, —OH, $C_{1-4}$ alkyl, $NH_2$, $NH(C_{1-4}$ alkyl), $N(C_{1-4}$ alkyl)$_2$, $C_{1-4}$ alkoxy, and —NHCO($C_{1-4}$ alkyl), and heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4;

p, at each occurrence, is independently selected from 0, 1, and 2;

provided (1) when L is NH, $R^1$ is other than

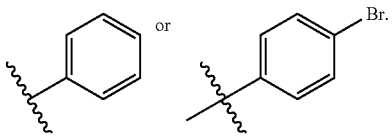 [SMILES: *c1ccccc1 ; *c1ccc(Br)cc1]

2. The compound of claim 1, wherein:

L is selected from —$CR^4R^4C(O)$—, —OC(O)—, and —$NR^6$—;

$R^4$, at each occurrence, is independently selected from H and $C_{1-4}$ alkyl; and $R^7$, at each occurrence, is independently selected from H, =O, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —NH-$COCF_3$, —$NHCO_2(C_{1-4}$ alkyl), —$NHCO_2(CH_2)_2OH$, —$NHC(O)NH_2$, —$NHC(O)NH(C_{1-4}$ alkyl), —NHC(O)N($C_{1-4}$ alkyl)$_2$, —$NHSO_2(C_{1-4}$ alkyl), —$SO_2NH_2$, —$SO_2NH(C_{1-4}$ alkyl), —$SO_2N(C_{1-4}$ alkyl)$_2$, —$CONH_2$, —$CONH(C_{1-4}$ alkyl), —$CON(C_{1-4}$ alkyl)$_2$, —$CH_2CONH_2$, —$(CH_2)_n$-carbocycle, —$O(CH_2)_n$-carbocycle, —$O(CH_2)_n$-heterocycle, and —$(CH_2)_n$-heterocycle comprising carbon atoms and 1-4 heteroatoms selected from N, $NR^8$, O, and $S(O)_p$ wherein said alkyl, alkoxyl, carbocycle, and heterocycle are substituted with 0-4 $R^9$.

3. The compound of claim 2, having Formula (II):

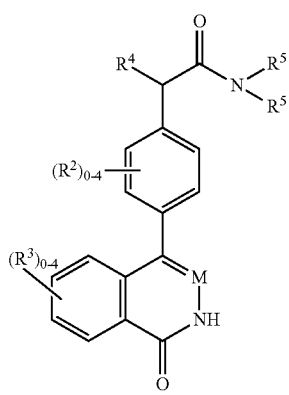

or a stereoisomer, a tautomer, or a pharmaceutically acceptable salt thereof, wherein:

M is N;

$R^5$, at each occurrence, is independently selected from H, $C_{1-4}$ alkyl, —$(CR^6R^6)_n$—$C_{3-10}$ carbocycle, and —$(CR^6R^6)_n$-4-10 membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form 4- to 10-membered heterocycle substituted with 1-4 $R^7$;

$R^7$, at each occurrence, is independently selected from H, =O, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —NH-$COCF_3$, —$NHCO_2(C_{1-4}$ alkyl), —$NHC(O)NH_2$, —$NHC(O)NH(C_{1-4}$ alkyl), —$NHC(O)N(C_{1-4}$ alkyl)$_2$, —$NHSO_2(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$CONH_2$, —CONH ($C_{1-4}$ alkyl), —$CON(C_{1-4}$ alkyl)$_2$, —$CH_2CONH_2$, —$(CH_2)_n$-carbocycle, —$O(CH_2)_n$-carbocycle, —$O(CH_2)_n$-heterocycle, and —$(CH_2)_n$-heterocycle comprising carbon atoms and 1-4 heteroatoms selected from N, $NR^8$, O, and $S(O)_p$, wherein said alkyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, C(O)carbocycle, C(O)heterocycle, $C(O)NR^5R^5$, C(O)O-alkyl, C(O)O-carbocycle, C(O)O-heterocycle, $SO_2$alkyl, $SO_2$carbocycle, $SO_2$heterocycle, $SO_2NR^5R^5$, —$(CH_2)_n$-carbocycle, and —$(CH_2)_n$-heterocycle, wherein said alkyl, carbocycle, and heterocycle are substituted with 0-4 $R^9$;

$R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, —$(CH_2)_n$$NR^aR^a$, —$(CH_2)_nCONR^aR^a$, —$O(CH_2)_n$heterocycle, —$O(CH_2)_{(2-4)}NR^aR^a$, —$(CR^{10}R^{10})_n$-4-10 membered heterocycle, wherein said alkyl, alkoxyl, carbocycle, and heterocycle are substituted with 0-4 $R^b$;

$R^{10}$ is selected from H and $C_{1-4}$ alkyl;

$R^a$, at each occurrence, is independently selected from H, $C_{1-4}$ alkyl, —$(CH_2)_n$OH, $CO(C_{1-4}$ alkyl), $COCF_3$, $CO_2$ ($C_{1-4}$ alkyl), —$CONH_2$, —CONH—$C_{1-4}$ alkylene-$CO_2$ ($C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form 4- to 10-membered heterocycle, wherein said alkyl, alkylene, and heterocycle are substituted with 0-4 $R^b$;

$R^b$, at each occurrence, is independently selected from =O, halo, $C_{1-4}$ alkyl, $C_{1-4}$ alkoxy, $OCF_3$, $NH_2$, $NO_2$, $N(C_{1-4}$alkyl)$_2$, $CO(C_{1-4}$alkyl), $CO(C_{1-4}$haloalkyl), $CO_2$ ($C_{1-4}$ alkyl), $CONH_2$, —$CONH(C_{1-4}$ alkyl), —CON ($C_{1-4}$ alkyl)$_2$, —CONH—$C_{1-4}$ alkylene-$O(C_{1-4}$ alkyl), —CONH—$C_{1-4}$ alkylene-$N(C_{1-4}$ alkyl)$_2$, —CONH—$C_{1-4}$ alkylene-$N(C_{1-4}$ alkyl)$_2$, —$C_{1-4}$ alkylene-O—P(O) $(OH)_2$, —$NHCO_2(C_{1-4}$alkyl), —$R^c$, $COR^c$, $CO_2R^c$, and $CONHR^c$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halo, —OH, $C_{1-4}$ alkyl, $NH_2$, $NH(C_{1-4}$ alkyl), $N(C_{1-4}$ alkyl)$_2$, $C_{1-4}$ alkoxy, and —NHCO($C_{1-4}$ alkyl), and heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4; and p, at each occurrence, is independently selected from 0, 1, and 2.

4. The compound of claim 3, wherein:

$R^5$ is selected from H, $C_{1-4}$ alkyl, —$(CH_2)_n$—$C_{3-6}$ cycloalkyl, —$(CH_2)_n$-aryl, or —$(CH_2)_n$-4-10 membered heterocycle selected from

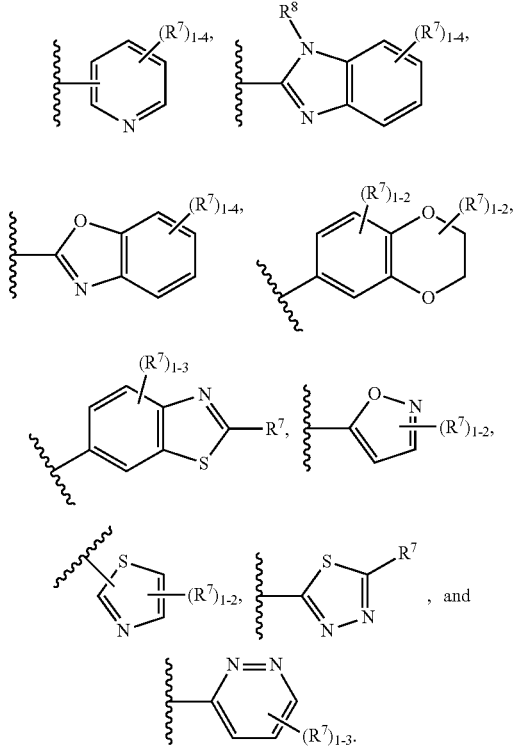

5. The compound of claim 3, wherein:

$R^5$ and $R^5$ are taken together with the nitrogen atom to which they are attached to form a heterocycle selected from

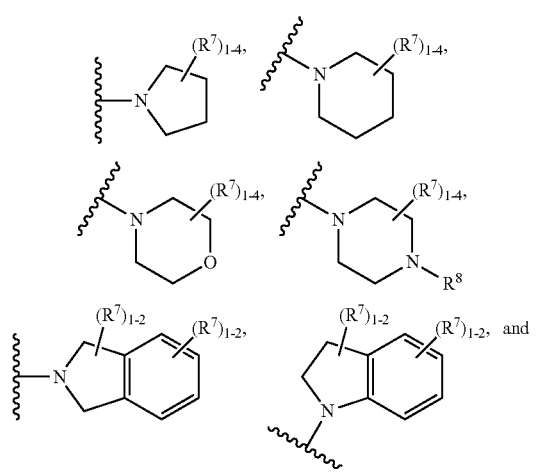

6. The compound of claim 2, having Formula (III):

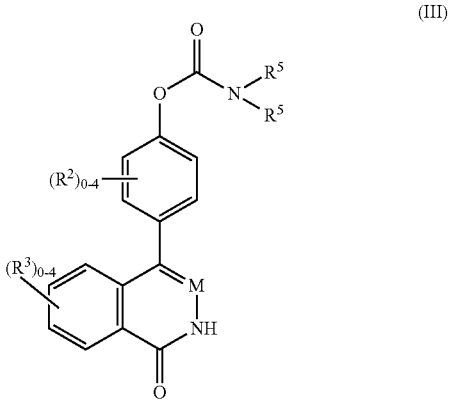

(III)

or a stereoisomer, a tautomer, or a pharmaceutically acceptable salt thereof, wherein:

M is N;

$R^5$, at each occurrence, is independently selected from H, $C_{1-4}$ alkyl, —$(CR^6R^6)_n$—$C_{3-10}$ carbocycle, and —$(CR^6R^6)_n$-4-10 membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form 4- to 10-membered heterocycle substituted with 1-4 $R^7$;

$R^6$, at each occurrence, is independently selected from H and $C_{1-4}$ alkyl;

$R^7$, at each occurrence, is independently selected from H, =O, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —NHCO($C_{1-4}$ alkyl), —NH-COCF$_3$, —NHCO$_2$($C_{1-4}$ alkyl), —NHC(O)NH$_2$, —NHC(O)NH($C_{1-4}$ alkyl), —NHC(O)N($C_{1-4}$ alkyl)$_2$, —NHSO$_2$($C_{1-4}$ alkyl), —SO$_2$NH$_2$, —SO$_2$NH($C_{1-4}$ alkyl), —SO$_2$N($C_{1-4}$ alkyl)$_2$, —SO$_2$NH(CH$_2$)$_2$OH, —SO$_2$NH(CH$_2$)$_2$O($C_{1-4}$ alkyl), —CONH$_2$, —CONH ($C_{1-4}$ alkyl), —CON($C_{1-4}$ alkyl)$_2$, —CH$_2$CONH$_2$, —$(CH_2)_n$-carbocycle, —O$(CH_2)_n$-carbocycle, —O$(CH_2)_n$-heterocycle, and —$(CH_2)_n$-heterocycle, wherein said alkyl, alkoxyl, carbocycle, and heterocycle are substituted with 0-4 $R^9$;

$R^8$, at each occurrence, is independently selected from H, $C_{1-4}$ alkyl, C(O)$C_{1-4}$alkyl, C(O)carbocycle, C(O)heterocycle, C(O)NR$^5$R$^5$, C(O)O-alkyl, C(O)O-carbocycle, C(O)O-heterocycle, SO$_2$alkyl, SO$_2$carbocycle, SO$_2$heterocycle, SO$_2$NR$^5$R$^5$, —$(CH_2)_n$-carbocycle, and —$(CH_2)_n$-heterocycle, wherein said alkyl, carbocycle, and heterocycle are substituted with 0-4 $R^9$;

$R^9$, at each occurrence, is independently selected from halogen, OH, NO$_2$, CHF$_2$, CF$_3$, $C_{1-4}$ alkyl, $C_{1-4}$ alkoxy, CH$_2$OH, CO$_2$H, CO$_2$($C_{1-4}$ alkyl), CONH$_2$, —$(CH_2)_n$ NR$^a$R$^a$, —(CH$_2$)$_n$CONR$^a$R$^a$, —O(CH$_2$)$_n$heterocycle, —O(CH$_2$)$_{(2-4)}$NR$^a$R$^a$, —(CR$^{10}$R$^{10}$)$_n$-4-10 membered heterocycle, wherein said alkyl, alkoxyl, carbocycle, and heterocycle are substituted with 0-4 R$^b$;

n, at each occurrence, is independently selected from 0, 1, 2, 3, and 4; and p, at each occurrence, is independently selected from 0, 1, and 2.

7. The compound of claim 2, wherein:

L is —NR$^6$—;

R$^1$ is selected from C$_{3-10}$ carbocycle and 5- to 10-membered heterocycle substituted with 1-4 R$^7$;

R$^5$, at each occurrence, is independently selected from H, C$_{1-4}$ alkyl, —(CR$^6$R$^6$)$_n$—C$_{3-10}$ carbocycle, and —(CR$^6$R$^6$)$_n$-4-10 membered heterocycle comprising carbon atoms and 1-4 heteroatoms selected from N, NR$^8$, O, and S(O)$_p$, wherein said alkyl, carbocycle, and heterocycle are substituted with 1-4 R$^7$;

alternatively, R$^5$ and R$^5$ are taken together with the nitrogen atom to which they are attached to form 4- to 10-membered heterocycle substituted with 1-4 R$^7$;

R$^6$, at each occurrence, is independently selected from H and C$_{1-4}$ alkyl;

R$^7$, at each occurrence, is independently selected from H, =O, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —CH$_2$NH$_2$, —NHCO(C$_{1-4}$ alkyl), —NHCOCF$_3$, —NHCO$_2$(C$_{1-4}$ alkyl), —NHC(O)NH$_2$, —NHC(O)NH(C$_{1-4}$ alkyl), —NHC(O)N(C$_{1-4}$ alkyl)$_2$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —CONH$_2$, —CONH(C$_{1-4}$ alkyl), —CON(C$_{1-4}$ alkyl)$_2$, —CH$_2$CONH$_2$, —(CH$_2$)$_n$-carbocycle, —O(CH$_2$)$_n$-carbocycle, —O(CH$_2$)$_n$-heterocycle, and —(CH$_2$)$_n$-heterocycle, wherein said alkyl, alkoxyl, carbocycle, and heterocycle are substituted with 0-4 R$^9$;

R$^8$, at each occurrence, is independently selected from H, C$_{1-4}$ alkyl, C(O)C$_{1-4}$alkyl, C(O)carbocycle, C(O)heterocycle, C(O)NR$^5$R$^5$, C(O)O-alkyl, C(O)O-carbocycle, C(O)O-heterocycle, SO$_2$alkyl, SO$_2$carbocycle, SO$_2$heterocycle, SO$_2$NR$^5$R$^5$, —(CH$_2$)$_n$-carbocycle, and —(CH$_2$)$_n$-heterocycle, wherein said alkyl, carbocycle, and heterocycle are substituted with 0-4 R$^9$;

R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —O(CH$_2$)$_n$heterocycle, —O(CH$_2$)$_{(2-4)}$NR$^a$R$^a$, —(CR$^{10}$R$^{10}$)$_n$-4-10 membered heterocycle, wherein said alkyl, alkoxyl, carbocycle, and heterocycle are substituted with 0-4 R$^b$;

n, at each occurrence, is independently selected from 0, 1, 2, 3, and 4; and p, at each occurrence, is independently selected from 0, 1, and 2.

8. The compound of claim 7, wherein:

L is —NR$^6$—; and

R$^1$ is selected from

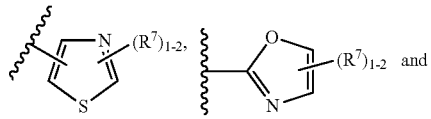

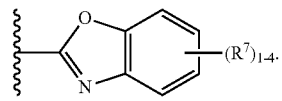

9. The compound of claim 1, selected from

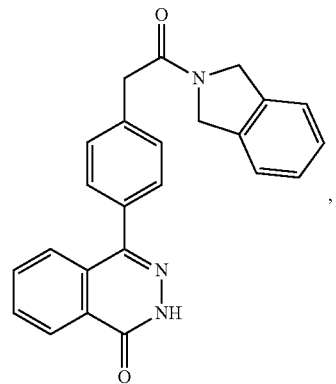

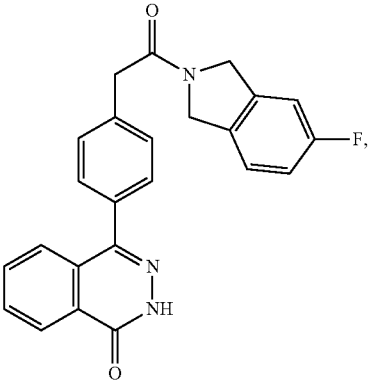

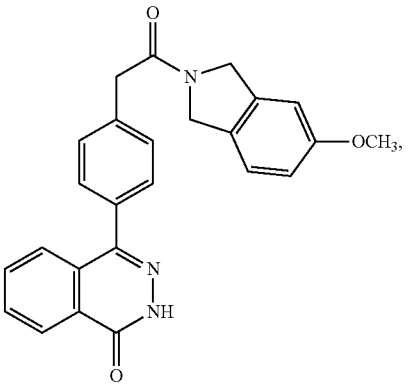

| 131 | 132 |
|---|---|
| -continued | -continued |
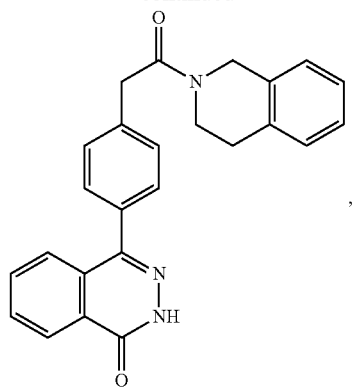
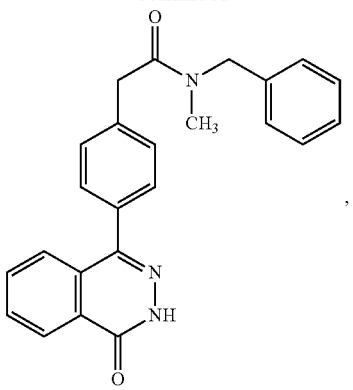

133
-continued
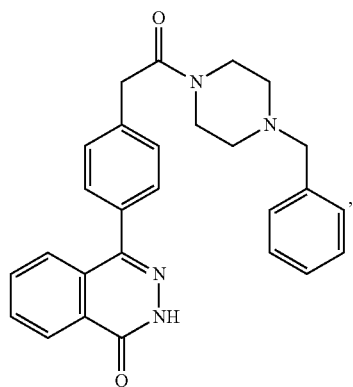
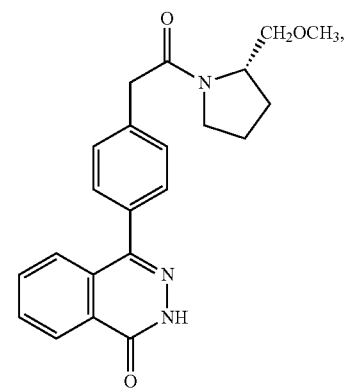
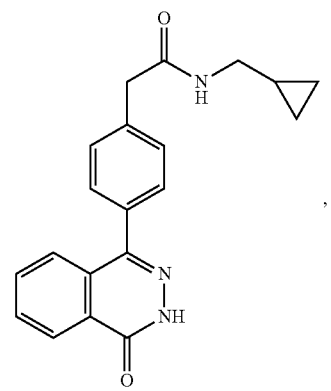
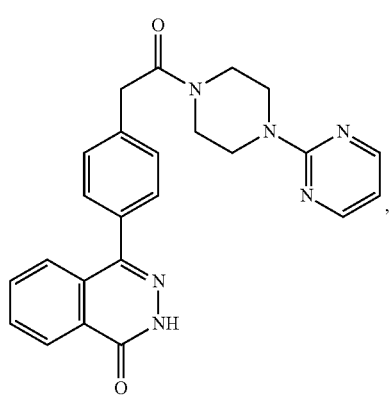
134
-continued
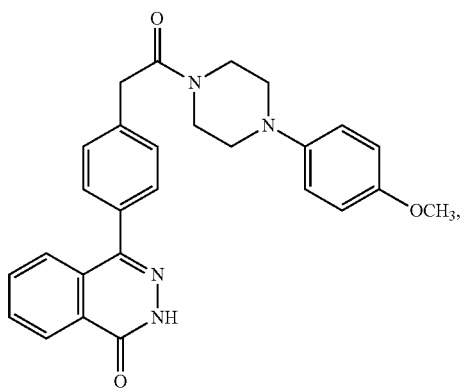
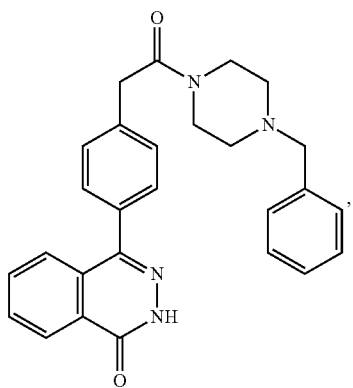
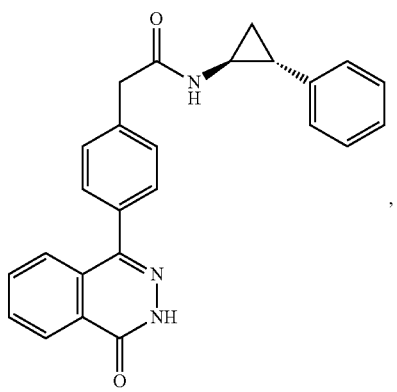
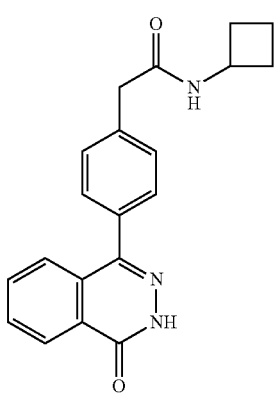

135
-continued
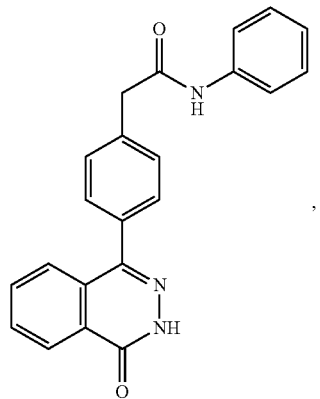
,
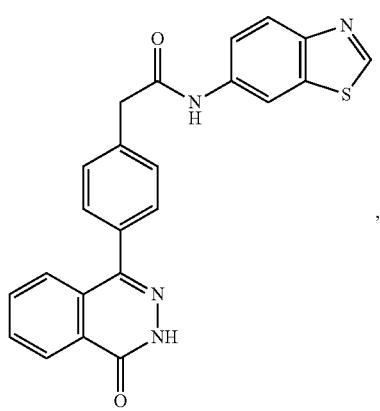
,
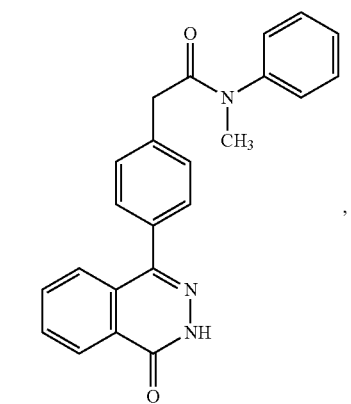
,
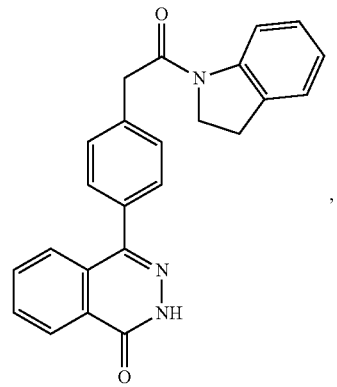
,
136
-continued
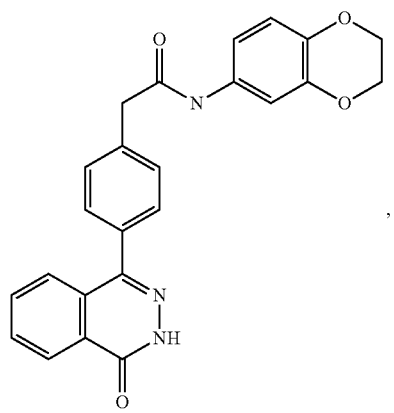
,
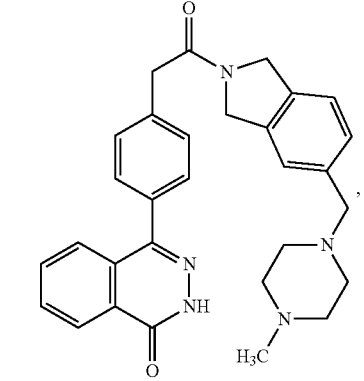
,
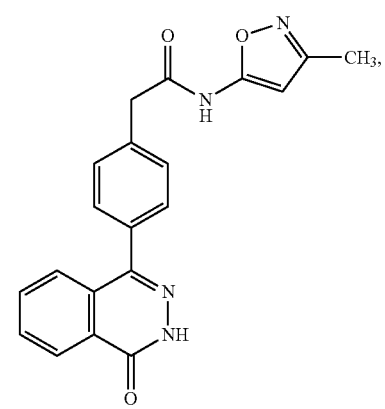
,
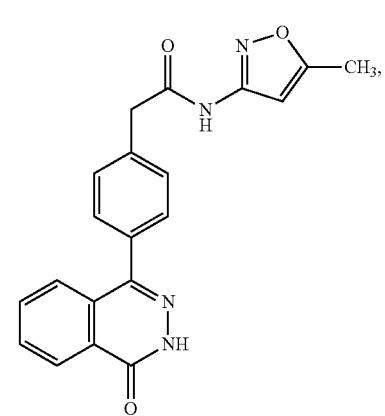

137
-continued
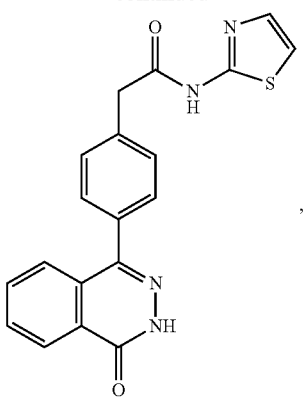
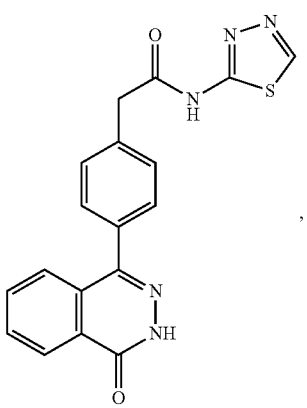
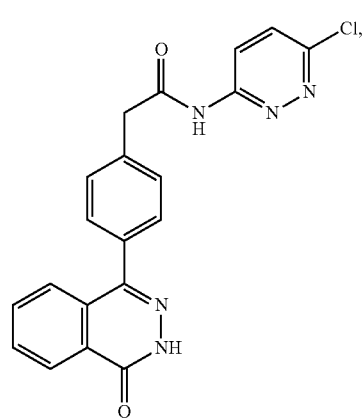
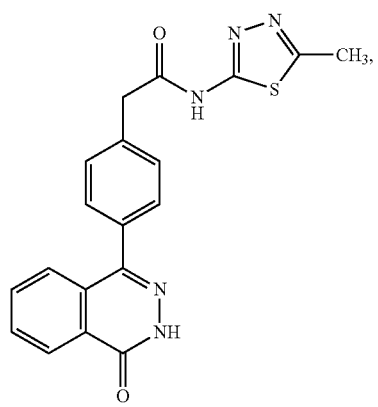
138
-continued
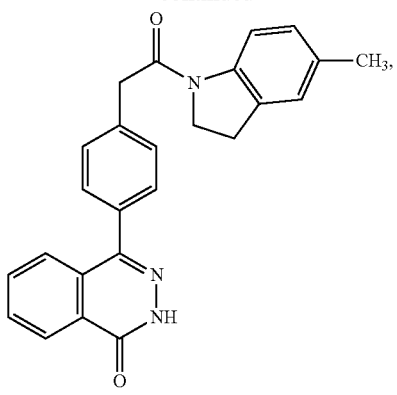
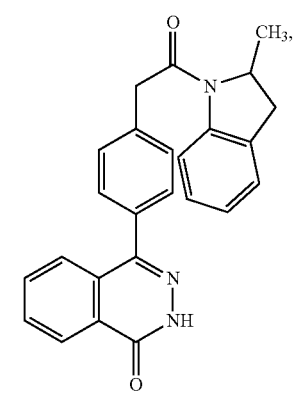
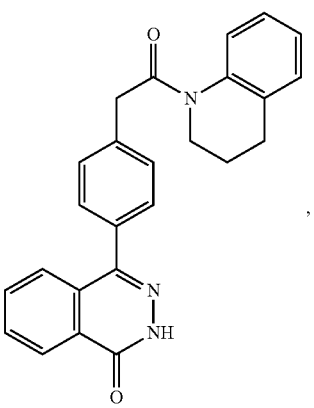
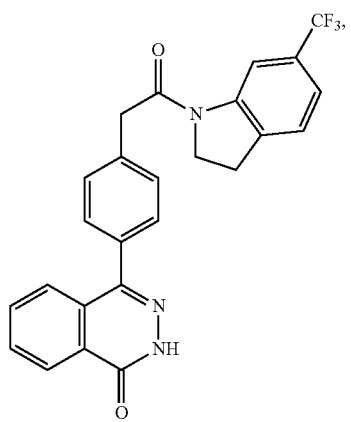

139
-continued
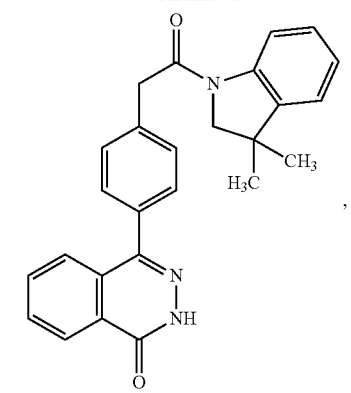
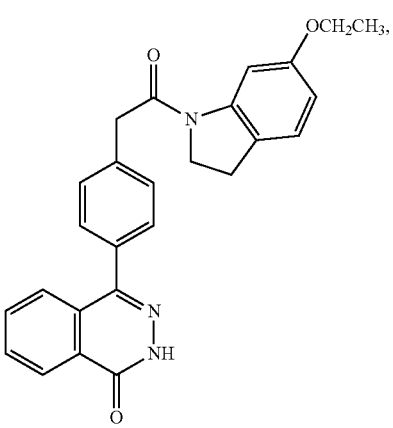
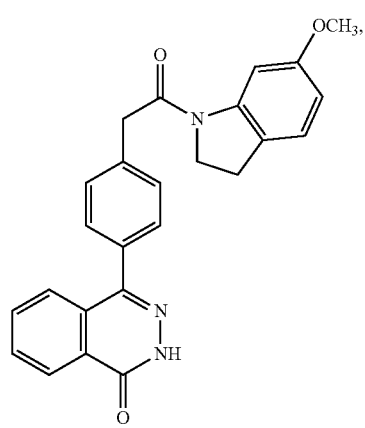
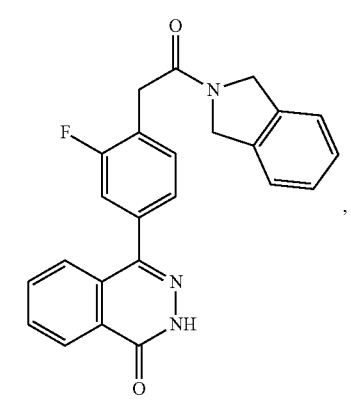
140
-continued
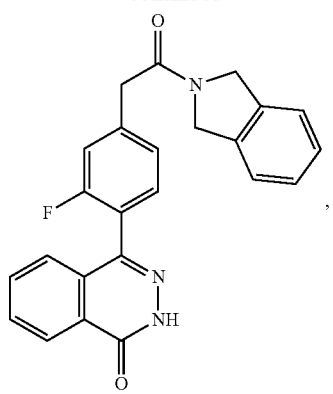
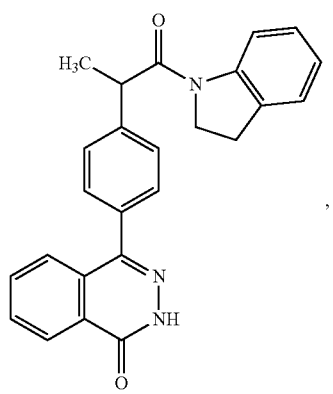
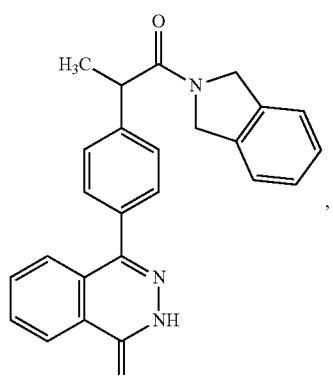
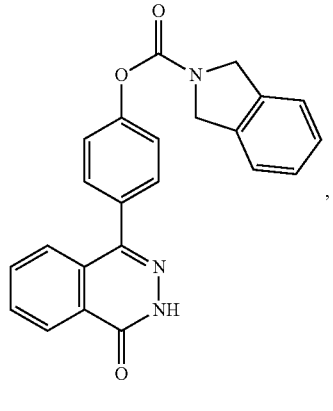

141
-continued
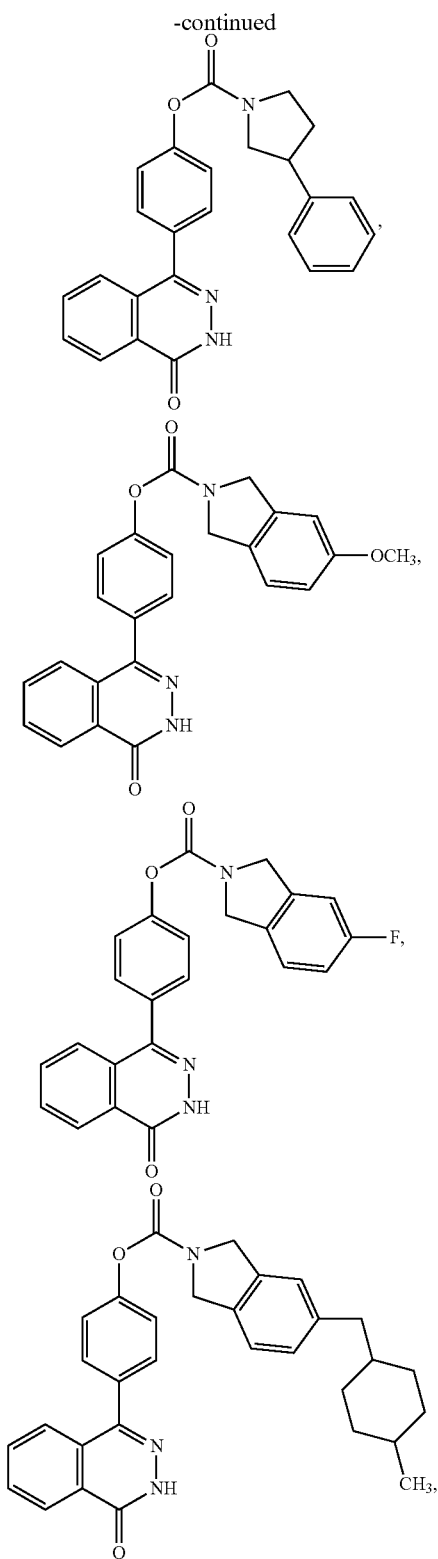
142
-continued
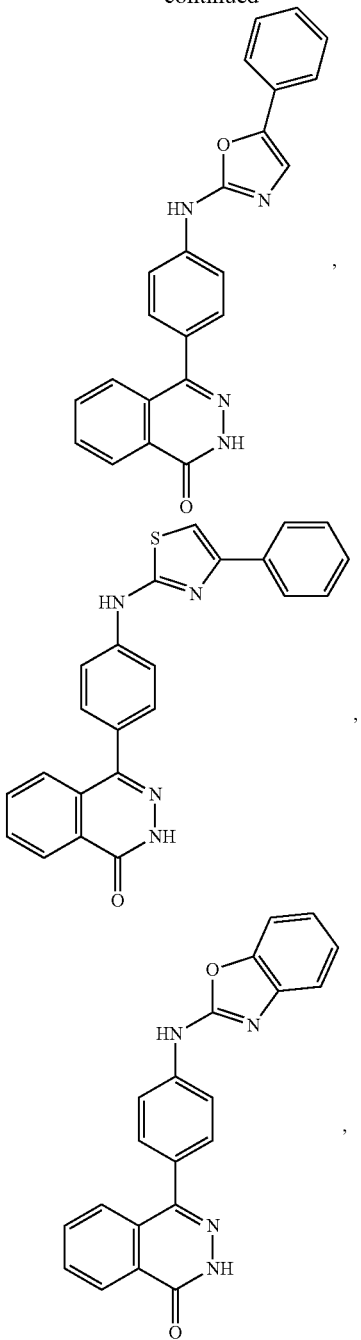
, and
or a stereoisomer, a tautomer or a pharmaceutically acceptable salt thereof.
10. A pharmaceutical composition comprising one or more compounds according to claim 1 and a pharmaceutically acceptable carrier or diluent.
* * * * *